United States Patent
Bou Hamdan et al.

(10) Patent No.: US 11,129,386 B2
(45) Date of Patent: *Sep. 28, 2021

(54) MICROBIOCIDAL QUINOLINE (THIO)CARBOXAMIDE DERIVATIVES

(71) Applicant: SYNGENTA PARTICIPATIONS AG, Basel (CH)

(72) Inventors: Farhan Bou Hamdan, Stein (CH); Laura Quaranta, Stein (CH); Matthias Weiss, Stein (CH)

(73) Assignee: SYNGENTA PARTICIPATIONS AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/645,680

(22) PCT Filed: Sep. 11, 2018

(86) PCT No.: PCT/EP2018/074513
§ 371 (c)(1),
(2) Date: Mar. 9, 2020

(87) PCT Pub. No.: WO2019/053024
PCT Pub. Date: Mar. 21, 2019

(65) Prior Publication Data
US 2020/0260728 A1    Aug. 20, 2020

(30) Foreign Application Priority Data

Sep. 13, 2017  (EP) .................... 17190888

(51) Int. Cl.
*A01N 43/42* (2006.01)
*C07D 215/38* (2006.01)

(52) U.S. Cl.
CPC .......... *A01N 43/42* (2013.01); *C07D 215/38* (2013.01)

(58) Field of Classification Search
None
See application file for complete search history.

(56) References Cited

FOREIGN PATENT DOCUMENTS

WO    2004039783 A1    5/2004

OTHER PUBLICATIONS

Chemical catalog RN 1539625-97-2; Feb. 9, 2014 (Year: 2014).*
Chemical catalog RN 1495743-30-0; Dec. 15, 2013 (Year: 2013).*
Extented European Search Report for EP Application No. 17190888.2 of EPO17190888.2 dated Dec. 18, 2017.
Database Registry (Online) Chemical—Silveton Ave. Suite 209, San Diego CA, A USBSTRACT Service, Columbus, OH, US: Dec. 15, 2013, retrieved from STN Database accession; & Mar. 27, 2017, Aurora Building Blocks, Aurora Fine Chemical LLC, No. 1495743-30-0/RN; & Database Chemcats (Online) Chemical/ On Database accession No. BSTRACTS Services, Columbus, OH; Mar. 27, 2017, retrieved from STN accession No. A.
Database Registry (Online) Chemical Abstracts Serv. Columbus OH, US, Feb. 9, 2014, retrieved from STN Database accession No. 1539625-897-2 & Database Chemcats (Online) Chemical Abstract Service, Columbus, OH, US; retrieved from STN accession No. AX110481787/ON Database accession No. 1892736123; & 21. Sep. 2017, Aldlab Chemicals Building Blocks, Aldlab Chemcials LLC 185 New Boston Street Woburn, MA.
Database Registry (Online) Chemical Abstracts Serv. Columbus, OH, US; Aug. 3, 2012, retrieved from STN Database accession No. 1386199-11-6/ON; & Database Chemcats (Online)Chemical Abstracts Service, OH, US; Mar. 27, 2017, retrieved from STN accession No. A20.375.309/ON Database accesion No. 176740213: & Mar. 27, 2017, Aurora Building Blocks, Aurora Fine Chemicals LLC, 7929 Silverton Ave. Suite 609, San Diego, CA 92126.
Database Chemcats (Online) Chemical Abstracts Service, Columbus OH, US; Sep. 15, 2014, retrieved from STN accession No. AMB16178300/ON Database accession No. 099242030; Sep. 15, 2014, Abinter Stock Screening Collection, Ambinter, c/o Greenpharma S.A.S., 3 Allee du Titane, Orleans 45100 France.
Database Caplus (Online) Chemical Abstracts Service, Columbus, OH, US Takematsu, Tetsuo et al: "Phenoxyisobutyramide heterocyclic derivatives as fungicides", retrieved from STN Database accesion No. 1987:50039; & JP S61126071 A (Hokko Chem Ind Co) Jun. 13, 1986.
Database Caplus (Online) Chemical Abstracts Service, Columbus, OH US; Ito, Hiroyuki et al; "Preparation of 1-aralkylcyclohexane compounds and agrochemical containing them", retrieved from STN Database accession No. 2005:693726 & JP 2005 206517 A (Sankyo Agro KK) Aug. 4, 2005.
International Search Report for International Application No. PCT/EP2018/074513 dated Oct. 8, 2018.

* cited by examiner

*Primary Examiner* — Alton N Pryor
(74) *Attorney, Agent, or Firm* — BakerHostetler; Toni-Junell Herbert

(57) ABSTRACT

Compounds of the formula (I) wherein the substituents are as defined in claim 1. Furthermore, the present invention relates to agrochemical compositions which comprise compounds of formula (I), to preparation of these compositions, and to the use of the compounds or compositions in agriculture or horticulture for combating, preventing or controlling infestation of plants, harvested food crops, seeds or non-living materials by phytopathogenic microorganisms, in particular fungi.

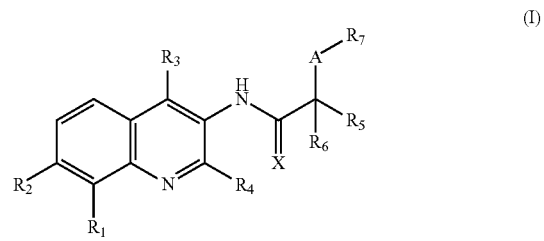

(I)

16 Claims, No Drawings

MICROBIOCIDAL QUINOLINE (THIO)CARBOXAMIDE DERIVATIVES

CROSS-REFERENCE TO RELATED APPLICATIONS

This application is a 371 National Stage application of International Application No. PCT/EP2018/074513 filed Sep. 11, 2018 which claims priority to EP 17190888.2, filed Sep. 13, 2017, the entire contents of which applications are hereby incorporated by reference.

The present invention relates to microbiocidal quinoline (thio)carboxamide derivatives, e.g. as active ingredients, which have microbiocidal activity, in particular fungicidal activity. The invention also relates to preparation of these quinoline (thio)carboxamide derivatives, to intermediates useful in the preparation of these quinoline (thio)carboxamide derivatives, to the preparation of these intermediates, to agrochemical compositions which comprise at least one of the quinoline (thio)carboxamide derivatives, to preparation of these compositions and to the use of the quinoline (thio)carboxamide derivatives or compositions in agriculture or horticulture for controlling or preventing infestation of plants, harvested food crops, seeds or non-living materials by phytopathogenic microorganisms, in particular fungi.

Certain fungicidal quinoline (thio)carboxamide compounds are described in WO04039783.

It has now surprisingly been found that certain novel quinoline (thio)carboxamide derivatives have favourable fungicidal properties.

The present invention therefore provides compounds of formula (I)

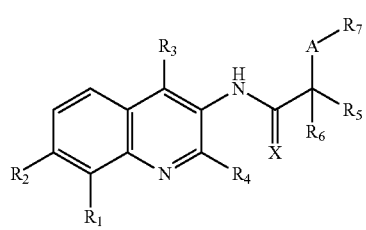

wherein
X is O or S;
$R_1$ is hydrogen, halogen, methyl or cyano;
$R_2$ is hydrogen, methyl or halogen;
$R_3$ and $R_4$ are each independently selected from hydrogen, halogen and methyl;
$R_5$ is $C_1$-$C_5$ alkyl, $C_2$-$C_5$ alkenyl, $C_1$-$C_4$ alkoxy, $C_3$-$C_5$ cycloalkyl($C_1$-$C_2$)alkyl or $C_3$-$C_6$ cycloalkyl, wherein the alkyl, alkenyl and cycloalkyl groups may be optionally substituted with 1 to 3 substituents independently selected from halogen, cyano, $C_1$-$C_3$ alkyl, $C_1$-$C_3$ haloalkyl, $C_1$-$C_3$ alkoxy and $C_1$-$C_3$ alkylthio;
$R_6$ is hydrogen, fluoro, cyano or $C_1$-$C_4$ alkyl, wherein the alkyl may be optionally substituted with 1 to 3 substituents independently selected from halogen and $C_1$-$C_3$ alkoxy;
A is a direct bond or $CR_8R_9$;
$R_7$ is $CF_3$, $C_2$-$C_5$ alkyl, $C_3$-$C_7$ cycloalkyl, $C_2$-$C_5$ alkenyl, $C_4$-$C_7$ cycloalkenyl, wherein the alkyl, cycloalkyl, alkenyl and cycloalkenyl may be optionally substituted with one or more substituents independently selected from halogen, cyano, $C_1$-$C_3$ alkyl, $C_1$-$C_3$ haloalkyl, $C_1$-$C_3$ alkoxy, $C_1$-$C_3$ alkylthio, $C_1$-$C_3$ haloalkoxy, $C_1$-$C_3$ haloalkylthio, $C_3$-$C_7$ cycloalkyl and phenyl (which itself may be optionally substituted with 1 to 3 substituents independently selected from halogen, cyano, $C_1$-$C_3$ alkyl, $C_1$-$C_3$ haloalkyl, $C_1$-$C_3$ alkoxy, $C_1$-$C_3$ alkylthio, $C_1$-$C_3$ haloalkoxy, $C_1$-$C_3$ haloalkylthio and $C_3$-$C_5$ cycloalkyl); and
$R_8$ and $R_9$ are each independently selected from hydrogen, fluoro and methyl; and salts, enantiomers and/or N-oxides thereof, provided the compound is not

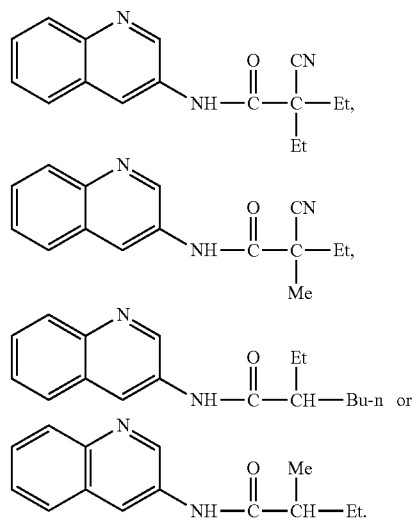

In a second aspect the present invention provides an agrochemical composition comprising a compound of formula (I).

Compounds of formula (I) may be used to control phytopathogenic microorganisms. Thus, in order to control a phytopathogen a compound of formula (I), or a composition comprising a compound of formula (I), according to the invention may be applied directly to the phytopathogen, or to the locus of a phytopathogen, in particular to a plant susceptible to attack by phytopathogens.

Thus, in a third aspect the present invention provides the use of a compound of formula (I), or a composition comprising a compound of formula (I), as described herein to control a phytopathogen.

In a further aspect the present invention provides a method of controlling phytopathogens, comprising applying a compound of formula (I), or a composition comprising a compound of formula (I), as described herein to said phytopathogen, or to the locus of said phytopathogen, in particular to a plant susceptible to attack by a phytopathogen.

Compounds of formula (I) are particularly effective in the control of phytopathogenic fungi.

Thus, in a yet further aspect the present invention provides the use of a compound of formula (I), or a composition comprising a compound of formula (I), as described herein to control phytopathogenic fungi.

In a further aspect the present invention provides a method of controlling phytopathogenic fungi, comprising applying a compound of formula (I), or a composition comprising a compound of formula (I), as described herein to said phytopathogenic fungi, or to the locus of said phytopathogenic fungi, in particular to a plant susceptible to attack by phytopathogenic fungi.

Where substituents are indicated as being optionally substituted, this means that they may or may not carry one or more identical or different substituents, e.g. one to four substituents. Normally not more than three such optional substituents are present at the same time. Preferably not more than two such optional substituents are present at the same time (i.e. the group may be optionally substituted by one or two of the substituents indicated as "optional"). Where the "optional substituent" group is a larger group, such as cycloalkyl or phenyl, it is most preferred that only one such optional substituent is present. Where a group is indicated as being substituted, e.g. alkyl, this includes those groups that are part of other groups, e.g. the alkyl in alkylthio.

The term "halogen" refers to fluorine, chlorine, bromine or iodine, preferably fluorine, chlorine or bromine.

Alkyl substituents (either alone or as part of a larger group, such as alkoxy-, alkylthio-) may be straight-chained or branched. Alkyl on its own or as part of another substituent is, depending upon the number of carbon atoms mentioned, for example, methyl, ethyl, n-propyl, n-butyl, n-pentyl, n-hexyl and the isomers thereof, for example, iso-propyl, iso-butyl, sec-butyl, tert-butyl or iso-amyl.

Alkenyl substituents (either alone or as part of a larger group, eg. alkenyloxy) can be in the form of straight or branched chains, and the alkenyl moieties, where appropriate, can be of either the (E)- or (Z)-configuration. Examples are vinyl and allyl. The alkenyl groups are preferably $C_2$-$C_6$, more preferably $C_2$-$C_4$ and most preferably $C_2$-$C_3$ alkenyl groups.

Alkynyl substituents (either alone or as part of a larger group, eg. alkynyloxy) can be in the form of straight or branched chains. Examples are ethynyl and propargyl. The alkynyl groups are preferably $C_2$-$C_6$, more preferably $C_2$-$C_4$ and most preferably $C_2$-$C_3$ alkynyl groups.

Cycloalkyl substituents may be saturated or partially unsaturated, preferably fully saturated, and are, for example, cyclopropyl, cyclobutyl, cyclopentyl or cyclohexyl.

Haloalkyl groups (either alone or as part of a larger group, eg. haloalkyloxy) may contain one or more identical or different halogen atoms and, for example, may stand for $CH_2Cl$, $CHCl_2$, $CCl_3$, $CH_2F$, $CHF_2$, $CF_3$, $CF_3CH_2$, $CH_3CF_2$, $CF_3CF_2$ or $CCl_3CCl_2$.

Haloalkenyl groups (either alone or as part of a larger group, eg. haloalkenyloxy) are alkenyl groups, respectively, which are substituted with one or more of the same or different halogen atoms and are, for example, 2,2-difluoro-vinyl or 1,2-dichloro-2-fluoro-vinyl.

Haloalkynyl groups (either alone or as part of a larger group, eg. haloalkynyloxy) are alkynyl groups, respectively, which are substituted with one or more of the same or different halogen atoms and are, for example, 1-chloro-prop-2-ynyl.

Alkoxy means a radical —OR, where R is alkyl, e.g. as defined above. Alkoxy groups include, but are not limited to, methoxy, ethoxy, 1-methylethoxy, propoxy, butoxy, 1-methylpropoxy and 2-methylpropoxy.

Cyano means a —CN group.

Amino means an —$NH_2$ group.

Hydroxyl or hydroxy stands for a —OH group.

Aryl groups (either alone or as part of a larger group, such as e.g. aryloxy, aryl-alkyl) are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is preferably substituted by one to four substituents, most preferably by one to three substituents.

Heteroaryl groups (either alone or as part of a larger group, such as e.g. heteroaryloxy, heteroaryl-alkyl) are aromatic ring systems containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl (e.g. [1,2,4]triazolyl), furanyl, thiophenyl, oxazolyl, isoxazolyl, oxadiazolyl, thiazolyl, isothiazolyl and thiadiazolyl. Examples of bicyclic groups include purinyl, quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is preferably substituted by one to four substituents, most preferably by one to three substituents.

Heterocyclyl groups, heterocycles or heterocyclic rings (either alone or as part of a larger group, such as heterocyclyl-alkyl) are non-aromatic ring structures containing up to 10 atoms including one or more (preferably one, two or three) heteroatoms selected from O, S and N. Examples of monocyclic groups include, oxetanyl, 4,5-dihydro-isoxazolyl, thietanyl, pyrrolidinyl, tetrahydrofuranyl, [1,3]dioxolanyl, piperidinyl, piperazinyl, [1,4]dioxanyl, imidazolidinyl, [1,3,5]oxadiazinanyl, hexahydro-pyrimidinyl, [1,3,5]triazinanyl and morpholinyl or their oxidised versions such as 1-oxo-thietanyl and 1,1-dioxo-thietanyl. Examples of bicyclic groups include 2,3-dihydro-benzofuranyl, benzo[1,4]dioxolanyl, benzo[1,3]dioxolanyl, chromenyl, and 2,3-dihydro-benzo[1,4]dioxinyl. Where a heterocyclyl moiety is said to be substituted, the heterocyclyl moiety is preferably substituted by one to four substituents, most preferably by one to three substituents.

The presence of one or more possible asymmetric carbon atoms in a compound of formula (I) means that the compounds may occur in optically isomeric forms, i.e. enantiomeric or diastereomeric forms. Also atropisomers may occur as a result of restricted rotation about a single bond. Formula (I) is intended to include all those possible isomeric forms and mixtures thereof. The present invention includes all those possible isomeric forms and mixtures thereof for a compound of formula (I). Likewise, formula (I) is intended to include all possible tautomers. The present invention includes all possible tautomeric forms for a compound of formula (I).

In each case, the compounds of formula (I) according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

Preferred values of A, X, $R_1$, $R_2$, $R_3$, $R_4$, $R_5$, $R_6$ and $R_7$ are, in any combination thereof, as set out below:

Preferably A is a direct bond or $CH_2$.

Most preferably A is $CH_2$.

Preferably X is O.

Preferably $R_1$ is hydrogen, fluoro, chloro, methyl or cyano.

More preferably $R_1$ is hydrogen, fluoro, chloro or methyl.

Most preferably $R_1$ is fluoro, chloro or methyl.

Preferably $R_2$ is hydrogen, methyl, chloro or fluoro.

More preferably $R_2$ is hydrogen, chloro or fluoro.

Most preferably $R_2$ is hydrogen or fluoro.

Preferably $R_3$ and $R_4$ are each independently selected from hydrogen and methyl.

More preferably $R_3$ is methyl and $R_4$ is hydrogen; or $R_3$ is hydrogen and $R_4$ is methyl; or $R_3$ is hydrogen and $R_4$ is hydrogen.

Most preferably $R_3$ and $R_4$ are both hydrogen

Preferably $R_5$ is $C_1$-$C_5$ alkyl, $C_2$-$C_4$ alkenyl, $C_3$-$C_5$ cycloalkyl-$CH_2$— or $C_3$-$C_5$ cycloalkyl, wherein the alkyl, alkenyl and cycloalkyl groups may be optionally substituted with 1 to 3 substituents independently selected from fluoro, chloro and $C_1$-$C_3$ alkyl.

More preferably $R_5$ is $C_1$-$C_5$ alkyl, $C_2$-$C_4$ alkenyl, $C_3$-$C_4$ cycloalkyl-$CH_2$— or $C_3$-$C_5$ cycloalkyl, wherein the alkyl, alkenyl and cycloalkyl groups may be optionally substituted with 1 to 3 substituents independently selected from fluoro, chloro and methyl.

Most preferably $R_5$ is trifluoroethyl, ethyl, isopropyl, iso-butyl, tert-butyl, neo-pentyl, $C_2$-$C_4$ alkenyl or cyclopropyl-$CH_2$—, wherein the ethyl, isopropyl, iso-butyl, alkenyl and cyclopropyl groups may be optionally substituted with 1 to 3 substituents independently selected from fluoro and chloro and/or one methyl group.

Preferably $R_6$ is hydrogen, fluoro, or $C_1$-$C_3$ alkyl, wherein the alkyl may be optionally substituted with a methoxy group.

More preferably $R_6$ is hydrogen or methyl, wherein the methyl may be optionally substituted with a methoxy group.

Most preferably $R_6$ is methyl.

Preferably $R_7$ is $CF_3$, $C_2$-$C_5$ alkyl, $C_3$-$C_7$ cycloalkyl, $C_2$-$C_5$ alkenyl, $C_4$-$C_7$ cycloalkenyl, wherein the alkyl, cycloalkyl, alkenyl and cycloalkenyl may be optionally substituted with one or more substituents independently selected from fluoro, chloro, cyano, $C_1$-$C_3$ alkyl, $C_1$-$C_3$ haloalkyl, $C_3$-$C_4$ cycloalkyl and phenyl (which itself may be optionally substituted with 1 to 3 substituents independently selected from fluoro, chloro, methyl and trifluoromethyl).

More preferably $R_7$ is $CF_3$, $C_2$-$C_4$ alkyl, $C_3$-$C_6$ cycloalkyl, $C_2$-$C_4$ alkenyl, $C_4$-$C_6$ cycloalkenyl, wherein the alkyl, cycloalkyl, alkenyl and cycloalkenyl may be optionally substituted with 1 to 3 substituents independently selected from fluoro, chloro, methyl, trifluoromethyl and cyclopropyl and/or one phenyl.

Even more preferably $R_7$ is $CF_3$, ethyl, isopropyl, tert-butyl, $C_2$-alkenyl, cyclopropyl, cyclobutyl, cyclopentyl, cyclohexyl, cyclopentenyl or cyclohexenyl, wherein the ethyl, isopropyl, alkenyl cyclopropyl, cyclobutyl, cyclopentyl, cyclohexyl, cyclopentenyl and cyclohexenyl may be optionally substituted with 1 to 3 substituents independently selected from fluoro and chloro and/or one or two methyl groups.

Most preferably $R_7$ is $CF_3$, isopropyl, tert-butyl, $C_2$-alkenyl, cyclopropyl, cyclobutyl, cyclopentyl or cyclohexyl, wherein the ethyl, isopropyl, alkenyl cyclopropyl, cyclobutyl, cyclopentyl and cyclohexyl may be optionally substituted with 1 to 3 substituents independently selected from fluoro and chloro and/or one methyl group.

Embodiments according to the invention are provided as set out below.

Embodiment 1 provides compounds of formula (I), or a salt, enantiomer or N-oxide thereof, as defined above.

Embodiment 2 provides compounds according to embodiment 1, or a salt, enantiomer or N-oxide thereof, wherein $R_1$ is hydrogen, fluoro, chloro, methyl or cyano.

Embodiment 3 provides compounds according to embodiment 1 or 2, or a salt, enantiomer or N-oxide thereof, wherein $R_2$ is hydrogen, methyl, chloro or fluoro.

Embodiment 4 provides compounds according to any one of embodiments 1, 2 or 3, or a salt, enantiomer or N-oxide thereof, wherein $R_3$ and $R_4$ are each independently selected from hydrogen and methyl.

Embodiment 5 provides compounds according to any one of embodiments 1, 2, 3 or 4, or a salt, enantiomer or N-oxide thereof, wherein $R_5$ is $C_1$-$C_5$ alkyl, $C_2$-$C_4$ alkenyl, $C_3$-$C_5$ cycloalkyl-$CH_2$— or $C_3$-$C_5$ cycloalkyl, wherein the alkyl, alkenyl and cycloalkyl groups may be optionally substituted with 1 to 3 substituents independently selected from fluoro, chloro and $C_1$-$C_3$ alkyl.

Embodiment 6 provides compounds according to any one of embodiments 1, 2, 3, 4, or 5, or a salt, enantiomer or N-oxide thereof, wherein $R_6$ is hydrogen, fluoro or $C_1$-$C_3$ alkyl, wherein the alkyl may be optionally substituted with a methoxy group.

Embodiment 7 provides compounds according to any one of embodiments 1, 2, 3, 4, 5, or 6, or a salt, enantiomer or N-oxide thereof, wherein $R_7$ is $CF_3$, $C_2$-$C_5$ alkyl, $C_3$-$C_7$ cycloalkyl, $C_2$-$C_5$ alkenyl, $C_4$-$C_7$ cycloalkenyl, wherein the alkyl, cycloalkyl, alkenyl and cycloalkenyl may be optionally substituted with one or more substituents independently selected from fluoro, chloro, cyano, $C_1$-$C_3$ alkyl, $C_1$-$C_3$ haloalkyl, $C_3$-$C_4$ cycloalkyl and phenyl (which itself may be optionally substituted with 1 to 3 substituents independently selected from fluoro, chloro, methyl and trifluoromethyl).

Embodiment 8 provides compounds according to any one of embodiments 1, 2, 3, 4, 5, 6, or 7, or a salt, enantiomer or N-oxide thereof, wherein $R_1$ is hydrogen, fluoro, chloro or methyl.

Embodiment 9 provides compounds according to any one of embodiments 1, 2, 3, 4, 5, 6, 7, or 8, or a salt, enantiomer or N-oxide thereof, wherein $R_2$ is hydrogen, chloro or fluoro.

Embodiment 10 provides compounds according to any one of embodiments 1, 2, 3, 4, 5, 6, 7, 8, or 9, or a salt, enantiomer or N-oxide thereof, wherein $R_3$ is methyl and $R_4$ is hydrogen; or $R_3$ is hydrogen and $R_4$ is methyl; or $R_3$ is hydrogen and $R_4$ is hydrogen.

Embodiment 11 provides compounds according to any one of embodiments 1, 2, 3, 4, 5, 6, 7, 8, 9 or 10, or a salt, enantiomer or N-oxide thereof, wherein $R_5$ is $C_1$-$C_5$ alkyl, $C_2$-$C_4$ alkenyl, $C_3$-$C_4$ cycloalkyl-$CH_2$— or $C_3$-$C_5$ cycloalkyl, wherein the alkyl, alkenyl and cycloalkyl groups may be optionally substituted with 1 to 3 substituents independently selected from fluoro, chloro and methyl.

Embodiment 12 provides compounds according to any one of embodiments 1, 2, 3, 4, 5, 6, 7, 8, 9, 10 or 11, or a salt, enantiomer or N-oxide thereof, wherein $R_6$ is hydrogen or methyl, wherein the methyl may be optionally substituted with a methoxy group.

Embodiment 13 provides compounds according to any one of embodiments 1, 2, 3, 4, 5, 6, 7, 8, 9, 10, 11 or 12, or a salt, enantiomer or N-oxide thereof, wherein $R_7$ is $CF_3$, $C_2$-$C_4$ alkyl, $C_3$-$C_6$ cycloalkyl, $C_2$-$C_4$ alkenyl, $C_4$-$C_6$ cycloalkenyl, wherein the alkyl, cycloalkyl, alkenyl and cycloalkenyl may be optionally substituted with 1 to 3 substituents independently selected from fluoro, chloro, methyl, trifluoromethyl and cyclopropyl and/or one phenyl.

Embodiment 14 provides compounds according to any one of embodiments 1, 2, 3, 4, 5, 6, 7, 8, 9, 10, 11, 12 or 13, or a salt, enantiomer or N-oxide thereof, wherein $R_1$ is fluoro, chloro or methyl.

Embodiment 15 provides compounds according to any one of embodiments 1, 2, 3, 4, 5, 6, 7, 8, 9, 10, 11, 12, 13 or 14, or a salt, enantiomer or N-oxide thereof, wherein $R_2$ is hydrogen or fluoro.

Embodiment 16 provides compounds according to any one of embodiments 1, 2, 3, 4, 5, 6, 7, 8, 9, 10, 11, 12, 13, 14 or 15, or a salt, enantiomer or N-oxide thereof, wherein $R_3$ and $R_4$ are both hydrogen.

Embodiment 17 provides compounds according to any one of embodiments 1, 2, 3, 4, 5, 6, 7, 8, 9, 10, 11, 12, 13, 14, 15 or 16, or a salt, enantiomer or N-oxide thereof, wherein $R_5$ is trifluoroethyl, ethyl, isopropyl, iso-butyl, tert-butyl, neo-pentyl, $C_2$-$C_4$ alkenyl or cyclopropyl-$CH_2$—, wherein the ethyl, isopropyl, iso-butyl, alkenyl and cyclopropyl groups may be optionally substituted with 1 to 3 substituents independently selected from fluoro and chloro and/or one methyl group.

Embodiment 18 provides compounds according to any one of embodiments 1, 2, 3, 4, 5, 6, 7, 8, 9, 10, 11, 12, 13, 14, 15, 16 or 17, or a salt, enantiomer or N-oxide thereof, wherein $R_6$ is methyl.

Embodiment 19 provides compounds according to any one of embodiments 1, 2, 3, 4, 5, 6, 7, 8, 9, 10, 11, 12, 13, 14, 15, 16, 17 or 18, or a salt, enantiomer or N-oxide thereof, wherein $R_7$ is $CF_3$, ethyl, isopropyl, tert-butyl, $C_2$-alkenyl, cyclopropyl, cyclobutyl, cyclopentyl, cyclohexyl, cyclopentenyl or cyclohexenyl, wherein the ethyl, isopropyl, alkenyl cyclopropyl, cyclobutyl, cyclopentyl, cyclohexyl, cyclopentenyl and cyclohexenyl may be optionally substituted with 1 to 3 substituents independently selected from fluoro and chloro and/or one or two methyl groups.

Embodiment 20 provides compounds according to any one of embodiments 1, 2, 3, 4, 5, 6, 7, 8, 9, 10, 11, 12, 13, 14, 15, 16, 17, 18 or 19, or a salt, enantiomer or N-oxide thereof, wherein $R_7$ is $CF_3$, isopropyl, tert-butyl, $C_2$-alkenyl, cyclopropyl, cyclobutyl, cyclopentyl or cyclohexyl, wherein the ethyl, isopropyl, alkenyl cyclopropyl, cyclobutyl, cyclopentyl and cyclohexyl may be optionally substituted with 1 to 3 substituents independently selected from fluoro and chloro and/or one methyl group.

Embodiment 21 provides compounds according to any one of embodiments 1, 2, 3, 4, 5, 6, 7, 8, 9, 10, 11, 12, 13, 14, 15, 16, 17, 18, 19 or 20, or a salt, enantiomer or N-oxide thereof, wherein A is a direct bond or $CH_2$.

Embodiment 22 provides compounds according to any one of embodiments 1, 2, 3, 4, 5, 6, 7, 8, 9, 10, 11, 12, 13, 14, 15, 16, 17, 18, 19, 20 or 21, or a salt, enantiomer or N-oxide thereof, wherein A is $CH_2$.

Embodiment 23 provides compounds according to any one of embodiments 1, 2, 3, 4, 5, 6, 7, 8, 9, 10, 11, 12, 13, 14, 15, 16, 17, 18, 19, 20, 21 or 22, or a salt, enantiomer or N-oxide thereof, wherein X is O.

Embodiment 24 provides compounds according to any one of embodiments 1, 2, 3, 4, 5, 6, 7, 8, 9, 10, 11, 12, 13, 14, 15, 16, 17, 18, 19, 20, 21 or 22, or a salt, enantiomer or N-oxide thereof, wherein X is S.

One group of compounds according to the invention are those of formula (I'):

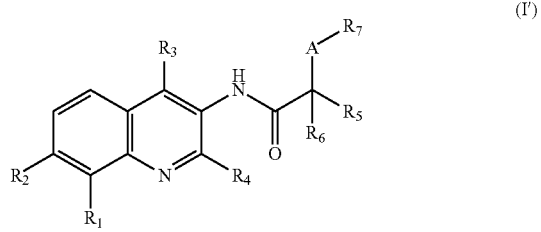

(I')

wherein A, $R_1$, $R_2$, $R_3$, $R_4$, $R_5$, $R_6$ and $R_7$ are as defined for compounds of formula (I), or a salt, enantiomer or N-oxide thereof. Preferred definitions of A, $R_1$, $R_2$, $R_3$, $R_4$, $R_5$, $R_6$ and $R_7$ are as defined for compounds of formula (I).

One group of compounds according to the invention are those of formula (I''):

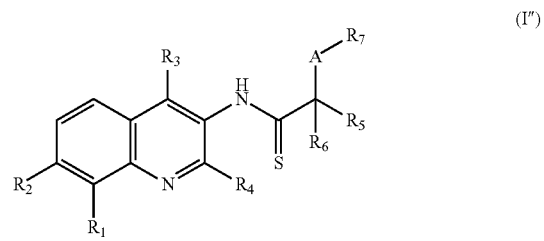

(I'')

wherein A, $R_1$, $R_2$, $R_3$, $R_4$, $R_5$, $R_6$ and $R_7$ are as defined for compounds of formula (I), or a salt, enantiomer or N-oxide thereof. Preferred definitions of A, $R_1$, $R_2$, $R_3$, $R_4$, $R_5$, $R_6$ and $R_7$ are as defined for compounds of formula (I).

A preferred group of compounds according to the invention are those of formula (I-1) which are compounds of formula (I) wherein X is O or S; $R_1$ is hydrogen, fluoro, chloro, methyl or cyano; $R_2$ is hydrogen, methyl, chloro or fluoro; $R_3$ and $R_4$ are each independently selected from hydrogen and methyl; $R_5$ is $C_1$-$C_5$ alkyl, $C_2$-$C_4$ alkenyl, $C_3$-$C_5$ cycloalkyl-$CH_2$— or $C_3$-$C_5$ cycloalkyl, wherein the alkyl, alkenyl and cycloalkyl groups may be optionally substituted with 1 to 3 substituents independently selected from fluoro, chloro and $C_1$-$C_3$ alkyl; $R_6$ is hydrogen, fluoro, or $C_1$-$C_3$ alkyl, wherein the alkyl may be optionally substituted with a methoxy group; A is a direct bond or $CH_2$; $R_7$ is $CF_3$, $C_2$-$C_5$ alkyl, $C_3$-$C_7$ cycloalkyl, $C_2$-$C_5$ alkenyl, $C_4$-$C_7$ cycloalkenyl, wherein the alkyl, cycloalkyl, alkenyl and cycloalkenyl may be optionally substituted with one or more substituents independently selected from fluoro, chloro, cyano, $C_1$-$C_3$ alkyl, $C_1$-$C_3$ haloalkyl, $C_3$-$C_4$ cycloalkyl and phenyl (which itself may be optionally substituted with 1 to 3 substituents independently selected from fluoro, chloro, methyl and trifluoromethyl); or a salt, enantiomer or N-oxide thereof.

One group of compounds according to this embodiment are compounds of formula (I-1a) which are compounds of formula (I-1) wherein X is O.

Another group of compounds according to this embodiment are compounds of formula (I-1 b) which are compounds of formula (I-1) wherein X is S.

A further preferred group of compounds according to the invention are those of formula (I-2) which are compounds of formula (I) wherein X is O or S; $R_1$ is hydrogen, fluoro, chloro or methyl; $R_2$ is hydrogen, chloro or fluoro; $R_3$ is methyl and $R_4$ is hydrogen; or $R_3$ is hydrogen and $R_4$ is methyl; or $R_3$ is hydrogen and $R_4$ is hydrogen; $R_5$ is $C_1$-$C_5$ alkyl, $C_2$-$C_4$ alkenyl, $C_3$-$C_4$ cycloalkyl-$CH_2$— or $C_3$-$C_5$ cycloalkyl, wherein the alkyl, alkenyl and cycloalkyl groups may be optionally substituted with 1 to 3 substituents independently selected from fluoro, chloro and methyl; $R_6$ is hydrogen or methyl, wherein the methyl may be optionally substituted with a methoxy group; A is a direct bond or $CH_2$; $R_7$ is $CF_3$, $C_2$-$C_4$ alkyl, $C_3$-$C_6$ cycloalkyl, $C_2$-$C_4$ alkenyl, $C_4$-$C_6$ cycloalkenyl, wherein the alkyl, cycloalkyl, alkenyl and cycloalkenyl may be optionally substituted with 1 to 3 substituents independently selected from fluoro, chloro, methyl, trifluoromethyl and cyclopropyl and/or one phenyl; or a salt, enantiomer or N-oxide thereof.

One group of compounds according to this embodiment are compounds of formula (I-2a) which are compounds of formula (I-2) wherein X is O.

Another group of compounds according to this embodiment are compounds of formula (I-2b) which are compounds of formula (I-2) wherein X is S.

A further preferred group of compounds according to the invention are those of formula (I-3) which are compounds of formula (I) wherein X is O or S; $R_1$ is fluoro, chloro or methyl; $R_2$ is hydrogen or fluoro; $R_3$ and $R_4$ are both hydrogen; $R_5$ is trifluoroethyl, ethyl, isopropyl, iso-butyl, tert-butyl, neo-pentyl, $C_2$-$C_4$ alkenyl or cyclopropyl-$CH_2$—, wherein the ethyl, isopropyl, iso-butyl, alkenyl and cyclopropyl groups may be optionally substituted with 1 to 3 substituents independently selected from fluoro and chloro and/or one methyl group; $R_6$ is methyl; A is $CH_2$; $R_7$ is $CF_3$, ethyl, isopropyl, tert-butyl, $C_2$-alkenyl, cyclopropyl, cyclobutyl, cyclopentyl, cyclohexyl, cyclopentenyl or cyclohexenyl, wherein the ethyl, isopropyl, alkenyl cyclopropyl, cyclobutyl, cyclopentyl, cyclohexyl, cyclopentenyl and cyclohexenyl may be optionally substituted with 1 to 3 substituents independently selected from fluoro and chloro and/or one or two methyl groups; or a salt, enantiomer or N-oxide thereof.

One group of compounds according to this embodiment are compounds of formula (I-3a) which are compounds of formula (I-3) wherein X is O.

Another group of compounds according to this embodiment are compounds of formula (I-3b) which are compounds of formula (I-3) wherein X is S.

Compounds according to the invention may possess any number of benefits including, inter alia, advantageous levels of biological activity for protecting plants against diseases that are caused by fungi or superior properties for use as agrochemical active ingredients (for example, greater biological activity, an advantageous spectrum of activity, an increased safety profile, improved physico-chemical properties, or increased biodegradability).

Specific examples of compounds of formula (I) are illustrated in the Tables A1 to A8 below: Table A1 provides 545 compounds of formula (I-a)

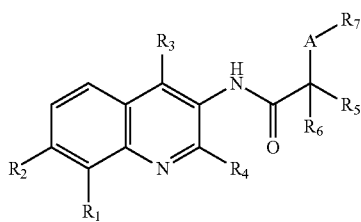

(I-a)

wherein $R_1$, $R_2$, $R_3$ and $R_4$ are all H
and wherein the values of $R_5$, $R_6$, A and $R_7$ are as defined in Table Z below:

TABLE Z

| Entry | $R_5$ | $R_6$ | A | $R_7$ |
|---|---|---|---|---|
| 1 | $CH_2CH(CH_3)_2$ | H | — | $CH_2C(CH_3)=CH_2$ |
| 2 | $CH_2CF_3$ | H | — | $CH_2C(CH_3)=CH_2$ |
| 3 | $CH_2C(CH_3)=CH_2$ | H | — | $CH_2C(CH_3)=CH_2$ |
| 4 | $CH_2$cyclopropyl | H | — | $CH_2C(CH_3)=CH_2$ |
| 5 | $CH_2C(CH_3)_3$ | H | — | $CH_2C(CH_3)=CH_2$ |
| 6 | $CH_2CH(CH_3)_2$ | H | — | $CH_2CH(CH_3)_2$ |
| 7 | $CH_2CF_3$ | H | — | $CH_2CH(CH_3)_2$ |
| 8 | $CH_2C(CH_3)=CH_2$ | H | — | $CH_2CH(CH_3)_2$ |
| 9 | $CH_2$cyclopropyl | H | — | $CH_2CH(CH_3)_2$ |
| 10 | $CH_2C(CH_3)_3$ | H | — | $CH_2CH(CH_3)_2$ |
| 11 | $CH_2CH(CH_3)_2$ | H | — | $CH_2C(CH_3)_3$ |
| 12 | $CH_2CF_3$ | H | — | $CH_2C(CH_3)_3$ |
| 13 | $CH_2C(CH_3)=CH_2$ | H | — | $CH_2C(CH_3)_3$ |
| 14 | $CH_2$cyclopropyl | H | — | $CH_2C(CH_3)_3$ |
| 15 | $CH_2C(CH_3)_3$ | H | — | $CH_2C(CH_3)_3$ |
| 16 | $CH_2CH(CH_3)_2$ | H | — | $CH_2CF_3$ |
| 17 | $CH_2CF_3$ | H | — | $CH_2CF_3$ |
| 18 | $CH_2C(CH_3)=CH_2$ | H | — | $CH_2CF_3$ |
| 19 | $CH_2$cyclopropyl | H | — | $CH_2CF_3$ |
| 20 | $CH_2C(CH_3)_3$ | H | — | $CH_2CF_3$ |
| 21 | $CH_2CH(CH_3)_2$ | H | — | $CH_2$cyclopropyl |
| 22 | $CH_2CF_3$ | H | — | $CH_2$cyclopropyl |
| 23 | $CH_2C(CH_3)=CH_2$ | H | — | $CH_2$cyclopropyl |
| 24 | $CH_2$cyclopropyl | H | — | $CH_2$cyclopropyl |
| 25 | $CH_2C(CH_3)_3$ | H | — | $CH_2$cyclopropyl |
| 26 | $CH_2CH(CH_3)_2$ | H | — | $C(CH_3)=CH(CH_3)$ |
| 27 | $CH_2CF_3$ | H | — | $C(CH_3)=CH(CH_3)$ |
| 28 | $CH_2C(CH_3)=CH_2$ | H | — | $C(CH_3)=CH(CH_3)$ |
| 29 | $CH_2$cyclopropyl | H | — | $C(CH_3)=CH(CH_3)$ |
| 30 | $CH_2C(CH_3)_3$ | H | — | $C(CH_3)=CH(CH_3)$ |
| 31 | $CH_2CH(CH_3)_2$ | F | — | $CH_2C(CH_3)=CH_2$ |
| 32 | $CH_2CF_3$ | F | — | $CH_2C(CH_3)=CH_2$ |
| 33 | $CH_2C(CH_3)=CH_2$ | F | — | $CH_2C(CH_3)=CH_2$ |
| 34 | $CH_2$cyclopropyl | F | — | $CH_2C(CH_3)=CH_2$ |
| 35 | $CH_2C(CH_3)_3$ | F | — | $CH_2C(CH_3)=CH_2$ |
| 36 | $CH_2CH(CH_3)_2$ | F | — | $CH_2CH(CH_3)_2$ |
| 37 | $CH_2CF_3$ | F | — | $CH_2CH(CH_3)_2$ |
| 38 | $CH_2C(CH_3)=CH_2$ | F | — | $CH_2CH(CH_3)_2$ |
| 39 | $CH_2$cyclopropyl | F | — | $CH_2CH(CH_3)_2$ |
| 40 | $CH_2C(CH_3)_3$ | F | — | $CH_2CH(CH_3)_2$ |
| 41 | $CH_2CH(CH_3)_2$ | F | — | $CH_2C(CH_3)_3$ |
| 42 | $CH_2CF_3$ | F | — | $CH_2C(CH_3)_3$ |
| 43 | $CH_2C(CH_3)=CH_2$ | F | — | $CH_2C(CH_3)_3$ |
| 44 | $CH_2$cyclopropyl | F | — | $CH_2C(CH_3)_3$ |
| 45 | $CH_2C(CH_3)_3$ | F | — | $CH_2C(CH_3)_3$ |
| 46 | $CH_2CH(CH_3)_2$ | F | — | $CH_2CF_3$ |
| 47 | $CH_2CF_3$ | F | — | $CH_2CF_3$ |
| 48 | $CH_2C(CH_3)=CH_2$ | F | — | $CH_2CF_3$ |
| 49 | $CH_2$cyclopropyl | F | — | $CH_2CF_3$ |
| 50 | $CH_2C(CH_3)_3$ | F | — | $CH_2CF_3$ |
| 51 | $CH_2CH(CH_3)_2$ | F | — | $CH_2$cyclopropyl |
| 52 | $CH_2CF_3$ | F | — | $CH_2$cyclopropyl |
| 53 | $CH_2C(CH_3)=CH_2$ | F | — | $CH_2$cyclopropyl |
| 54 | $CH_2$cyclopropyl | F | — | $CH_2$cyclopropyl |
| 55 | $CH_2C(CH_3)_3$ | F | — | $CH_2$cyclopropyl |
| 56 | $CH_2CH(CH_3)_2$ | F | — | $C(CH_3)=CH(CH_3)$ |
| 57 | $CH_2CF_3$ | F | — | $C(CH_3)=CH(CH_3)$ |
| 58 | $CH_2C(CH_3)=CH_2$ | F | — | $C(CH_3)=CH(CH_3)$ |
| 59 | $CH_2$cyclopropyl | F | — | $C(CH_3)=CH(CH_3)$ |
| 60 | $CH_2C(CH_3)_3$ | F | — | $C(CH_3)=CH(CH_3)$ |
| 61 | $CH_2CH_3$ | $CH_3$ | — | $CH(CH_3)_2$ |
| 62 | $CH(CH_3)_2$ | $CH_3$ | — | $CH(CH_3)_2$ |
| 63 | $C(CH_3)_3$ | $CH_3$ | — | $CH(CH_3)_2$ |
| 64 | $CH_2C(CH_3)=CH_2$ | $CH_3$ | — | $CH(CH_3)_2$ |
| 65 | $CH_2C(F)=CH_2$ | $CH_3$ | — | $CH(CH_3)_2$ |
| 66 | $CH_2CH=CH_2$ | $CH_3$ | — | $CH(CH_3)_2$ |
| 67 | $CH_2$(1-fluorocyclopropyl) | $CH_3$ | — | $CH(CH_3)_2$ |
| 68 | $CH_2CF(CH_3)_2$ | $CH_3$ | — | $CH(CH_3)_2$ |
| 69 | $CH_2CF_2CH_3$ | $CH_3$ | — | $CH(CH_3)_2$ |
| 70 | $CH_2CH_3$ | $CH_3$ | — | $C(CH_3)_3$ |
| 71 | $CH(CH_3)_2$ | $CH_3$ | — | $C(CH_3)_3$ |
| 72 | $C(CH_3)_3$ | $CH_3$ | — | $C(CH_3)_3$ |
| 73 | $CH_2C(F)=CH_2$ | $CH_3$ | — | $C(CH_3)_3$ |
| 74 | $CH_2CH=CH_2$ | $CH_3$ | — | $C(CH_3)_3$ |
| 75 | $CH_2$(1-fluorocyclopropyl) | $CH_3$ | — | $C(CH_3)_3$ |
| 76 | $CH_2CF(CH_3)_2$ | $CH_3$ | — | $C(CH_3)_3$ |
| 77 | $CH_2CF_2CH_3$ | $CH_3$ | — | $C(CH_3)_3$ |
| 78 | $CH_2CH_3$ | $CH_3$ | — | $C(CH_3)=CH_2$ |
| 79 | $CH(CH_3)_2$ | $CH_3$ | — | $C(CH_3)=CH_2$ |
| 80 | $C(CH_3)_3$ | $CH_3$ | — | $C(CH_3)=CH_2$ |
| 81 | $CH_2CF_3$ | $CH_3$ | — | $C(CH_3)=CH_2$ |
| 82 | $CH_2CH(CH_3)_2$ | $CH_3$ | — | $C(CH_3)=CH_2$ |

TABLE Z-continued

| Entry | R$_5$ | R$_6$ | A | R$_7$ |
|---|---|---|---|---|
| 83 | CH$_2$C(CH$_3$)=CH$_2$ | CH$_3$ | — | C(CH$_3$)=CH$_2$ |
| 84 | CH$_2$C(Cl)=CH$_2$ | CH$_3$ | — | C(CH$_3$)=CH$_2$ |
| 85 | CH$_2$C(F)=CH$_2$ | CH$_3$ | — | C(CH$_3$)=CH$_2$ |
| 86 | CH$_2$C(CH$_3$)$_3$ | CH$_3$ | — | C(CH$_3$)=CH$_2$ |
| 87 | CH$_2$CH=OH$_2$ | CH$_3$ | — | C(CH$_3$)=CH$_2$ |
| 88 | CH$_2$cyclopropyl | CH$_3$ | — | C(CH$_3$)=CH$_2$ |
| 89 | CH$_2$(1-methylcyclopropyl) | CH$_3$ | — | C(CH$_3$)=CH$_2$ |
| 90 | CH$_2$(1-fluorocyclopropyl) | CH$_3$ | — | C(CH$_3$)=CH$_2$ |
| 91 | CH$_2$CF(CH$_3$)$_2$ | CH$_3$ | — | C(CH$_3$)=CH$_2$ |
| 92 | CH$_2$CF$_2$CH$_3$ | CH$_3$ | — | C(CH$_3$)=CH$_2$ |
| 93 | CH$_2$CH$_3$ | CH$_3$ | — | C(Cl)=CH$_2$ |
| 94 | CH(CH$_3$)$_2$ | CH$_3$ | — | C(Cl)=CH$_2$ |
| 95 | C(CH$_3$)$_3$ | CH$_3$ | — | C(Cl)=CH$_2$ |
| 96 | CH$_2$CF$_3$ | CH$_3$ | — | C(Cl)=CH$_2$ |
| 97 | CH$_2$CH(CH$_3$)$_2$ | CH$_3$ | — | C(Cl)=CH$_2$ |
| 98 | CH$_2$C(CH$_3$)=CH$_2$ | CH$_3$ | — | C(Cl)=CH$_2$ |
| 99 | CH$_2$C(Cl)=CH$_2$ | CH$_3$ | — | C(Cl)=CH$_2$ |
| 100 | CH$_2$C(F)=CH$_2$ | CH$_3$ | — | C(Cl)=CH$_2$ |
| 101 | CH$_2$C(CH$_3$)$_3$ | CH$_3$ | — | C(Cl)=CH$_2$ |
| 102 | CH$_2$CH=CH$_2$ | CH$_3$ | — | C(Cl)=CH$_2$ |
| 103 | CH$_2$cyclopropyl | CH$_3$ | — | C(Cl)=CH$_2$ |
| 104 | CH$_2$(1-methylcyclopropyl) | CH$_3$ | — | C(Cl)=CH$_2$ |
| 105 | CH$_2$(1-fluorocyclopropyl) | CH$_3$ | — | C(Cl)=CH$_2$ |
| 106 | CH$_2$CF(CH$_3$)$_2$ | CH$_3$ | — | C(Cl)=CH$_2$ |
| 107 | CH$_2$CF$_2$CH$_3$ | CH$_3$ | — | C(Cl)=CH$_2$ |
| 108 | CH$_2$CH$_3$ | CH$_3$ | — | C(CH$_3$)=CH(CH$_3$) |
| 109 | CH(CH$_3$)$_2$ | CH$_3$ | — | C(CH$_3$)=CH(CH$_3$) |
| 110 | C(CH$_3$)$_3$ | CH$_3$ | — | C(CH$_3$)=CH(CH$_3$) |
| 111 | CH$_2$CF$_3$ | CH$_3$ | — | C(CH$_3$)=CH(CH$_3$) |
| 112 | CH$_2$CH(CH$_3$)$_2$ | CH$_3$ | — | C(CH$_3$)=CH(CH$_3$) |
| 113 | CH$_2$C(CH$_3$)=CH$_2$ | CH$_3$ | — | C(CH$_3$)=CH(CH$_3$) |
| 114 | CH$_2$C(Cl)=CH$_2$ | CH$_3$ | — | C(CH$_3$)=CH(CH$_3$) |
| 115 | CH$_2$C(F)=CH$_2$ | CH$_3$ | — | C(CH$_3$)=CH(CH$_3$) |
| 116 | CH$_2$C(CH$_3$)$_3$ | CH$_3$ | — | C(CH$_3$)=CH(CH$_3$) |
| 117 | CH$_2$CH=CH$_2$ | CH$_3$ | — | C(CH$_3$)=CH(CH$_3$) |
| 118 | CH$_2$cyclopropyl | CH$_3$ | — | C(CH$_3$)=CH(CH$_3$) |
| 119 | CH$_2$(1-methylcyclopropyl) | CH$_3$ | — | C(CH$_3$)=CH(CH$_3$) |
| 120 | CH$_2$(1-fluorocyclopropyl) | CH$_3$ | — | C(CH$_3$)=CH(CH$_3$) |
| 121 | CH$_2$CF(CH$_3$)$_2$ | CH$_3$ | — | C(CH$_3$)=CH(CH$_3$) |
| 122 | CH$_2$CF$_2$CH$_3$ | CH$_3$ | — | C(CH$_3$)=CH(CH$_3$) |
| 123 | CH$_2$CH$_3$ | CH$_3$ | — | C(F)=C(CH$_3$)$_2$ |
| 124 | CH(CH$_3$)$_2$ | CH$_3$ | — | C(F)=C(CH$_3$)$_2$ |
| 125 | C(CH$_3$)$_3$ | CH$_3$ | — | C(F)=C(CH$_3$)$_2$ |
| 126 | CH$_2$CF$_3$ | CH$_3$ | — | C(F)=C(CH$_3$)$_2$ |
| 127 | CH$_2$CH(CH$_3$)$_2$ | CH$_3$ | — | C(F)=C(CH$_3$)$_2$ |
| 128 | CH$_2$C(CH$_3$)=CH$_2$ | CH$_3$ | — | C(F)=C(CH$_3$)$_2$ |
| 129 | CH$_2$C(Cl)=CH$_2$ | CH$_3$ | — | C(F)=C(CH$_3$)$_2$ |
| 130 | CH$_2$C(F)=CH$_2$ | CH$_3$ | — | C(F)=C(CH$_3$)$_2$ |
| 131 | CH$_2$C(CH$_3$)$_3$ | CH$_3$ | — | C(F)=C(CH$_3$)$_2$ |
| 132 | CH$_2$CH=CH$_2$ | CH$_3$ | — | C(F)=C(CH$_3$)$_2$ |
| 133 | CH$_2$cyclopropyl | CH$_3$ | — | C(F)=C(CH$_3$)$_2$ |
| 134 | CH$_2$(1-methylcyclopropyl) | CH$_3$ | — | C(F)=C(CH$_3$)$_2$ |
| 135 | CH$_2$(1-fluorocyclopropyl) | CH$_3$ | — | C(F)=C(CH$_3$)$_2$ |
| 136 | CH$_2$CF(CH$_3$)$_2$ | CH$_3$ | — | C(F)=C(CH$_3$)$_2$ |
| 137 | CH$_2$CF$_2$CH$_3$ | CH$_3$ | — | C(F)=C(CH$_3$)$_2$ |
| 138 | CH$_2$CH$_3$ | CH$_3$ | — | CH=C(CH$_3$)$_2$ |
| 139 | CH(CH$_3$)$_2$ | CH$_3$ | — | CH=C(CH$_3$)$_2$ |
| 140 | C(CH$_3$)$_3$ | CH$_3$ | — | CH=C(CH$_3$)$_2$ |
| 141 | CH$_2$CF$_3$ | CH$_3$ | — | CH=C(CH$_3$)$_2$ |
| 142 | CH$_2$CH(CH$_3$)$_2$ | CH$_3$ | — | CH=C(CH$_3$)$_2$ |
| 143 | CH$_2$C(CH$_3$)=CH$_2$ | CH$_3$ | — | CH=C(CH$_3$)$_2$ |
| 144 | CH$_2$C(Cl)=CH$_2$ | CH$_3$ | — | CH=C(CH$_3$)$_2$ |
| 145 | CH$_2$C(F)=CH$_2$ | CH$_3$ | — | CH=C(CH$_3$)$_2$ |
| 146 | CH$_2$C(CH$_3$)$_3$ | CH$_3$ | — | CH=C(CH$_3$)$_2$ |
| 147 | CH$_2$CH=CH$_2$ | CH$_3$ | — | CH=C(CH$_3$)$_2$ |
| 148 | CH$_2$cyclopropyl | CH$_3$ | — | CH=C(CH$_3$)$_2$ |
| 149 | CH$_2$(1-methylcyclopropyl) | CH$_3$ | — | CH=C(CH$_3$)$_2$ |
| 150 | CH$_2$(1-fluorocyclopropyl) | CH$_3$ | — | CH=C(CH$_3$)$_2$ |
| 151 | CH$_2$CF(CH$_3$)$_2$ | CH$_3$ | — | CH=C(CH$_3$)$_2$ |
| 152 | CH$_2$CF$_2$CH$_3$ | CH$_3$ | — | CH=C(CH$_3$)$_2$ |
| 153 | CH$_2$CH$_3$ | CH$_3$ | — | C(CH$_3$)=C(CH$_3$)$_2$ |
| 154 | CH(CH$_3$)$_2$ | CH$_3$ | — | C(CH$_3$)=C(CH$_3$)$_2$ |
| 155 | C(CH$_3$)$_3$ | CH$_3$ | — | C(CH$_3$)=C(CH$_3$)$_2$ |
| 156 | CH$_2$CF$_3$ | CH$_3$ | — | C(CH$_3$)=C(CH$_3$)$_2$ |
| 157 | CH$_2$CH(CH$_3$)$_2$ | CH$_3$ | — | C(CH$_3$)=C(CH$_3$)$_2$ |
| 158 | CH$_2$C(CH$_3$)=CH$_2$ | CH$_3$ | — | C(CH$_3$)=C(CH$_3$)$_2$ |
| 159 | CH$_2$C(Cl)=CH$_2$ | CH$_3$ | — | C(CH$_3$)=C(CH$_3$)$_2$ |
| 160 | CH$_2$C(F)=CH$_2$ | CH$_3$ | — | C(CH$_3$)=C(CH$_3$)$_2$ |
| 161 | CH$_2$C(CH$_3$)$_3$ | CH$_3$ | — | C(CH$_3$)=C(CH$_3$)$_2$ |
| 162 | CH$_2$CH=CH$_2$ | CH$_3$ | — | C(CH$_3$)=C(CH$_3$)$_2$ |
| 163 | CH$_2$cyclopropyl | CH$_3$ | — | C(CH$_3$)=C(CH$_3$)$_2$ |
| 164 | CH$_2$(1-methylcyclopropyl) | CH$_3$ | — | C(CH$_3$)=C(CH$_3$)$_2$ |
| 165 | CH$_2$(1-fluorocyclopropyl) | CH$_3$ | — | C(CH$_3$)=C(CH$_3$)$_2$ |
| 166 | CH$_2$CF(CH$_3$)$_2$ | CH$_3$ | — | C(CH$_3$)=C(CH$_3$)$_2$ |
| 167 | CH$_2$CF$_2$CH$_3$ | CH$_3$ | — | C(CH$_3$)=C(CH$_3$)$_2$ |
| 168 | CH$_2$CH$_3$ | CH$_3$ | — | CF$_3$ |
| 169 | CH(CH$_3$)$_2$ | CH$_3$ | — | CF$_3$ |
| 170 | C(CH$_3$)$_3$ | CH$_3$ | — | CF$_3$ |
| 171 | CH$_2$CF$_3$ | CH$_3$ | — | CF$_3$ |
| 172 | CH$_2$CH(CH$_3$)$_2$ | CH$_3$ | — | CF$_3$ |
| 173 | CH$_2$C(CH$_3$)=CH$_2$ | CH$_3$ | — | CF$_3$ |
| 174 | CH$_2$C(Cl)=CH$_2$ | CH$_3$ | — | CF$_3$ |
| 175 | CH$_2$C(F)=CH$_2$ | CH$_3$ | — | CF$_3$ |
| 176 | CH$_2$C(CH$_3$)$_3$ | CH$_3$ | — | CF$_3$ |
| 177 | CH$_2$CH=CH$_2$ | CH$_3$ | — | CF$_3$ |
| 178 | CH$_2$cyclopropyl | CH$_3$ | — | CF$_3$ |
| 179 | CH$_2$(1-methylcyclopropyl) | CH$_3$ | — | CF$_3$ |
| 180 | CH$_2$(1-fluorocyclopropyl) | CH$_3$ | — | CF$_3$ |
| 181 | CH$_2$CF(CH$_3$)$_2$ | CH$_3$ | — | CF$_3$ |
| 182 | CH$_2$CF$_2$CH$_3$ | CH$_3$ | — | CF$_3$ |
| 183 | CH$_3$ | CH$_3$ | — | cyclopropyl |
| 184 | CH$_2$CH$_3$ | CH$_3$ | — | cyclopropyl |
| 185 | CH(CH$_3$)$_2$ | CH$_3$ | — | cyclopropyl |
| 186 | C(CH$_3$)$_3$ | CH$_3$ | — | cyclopropyl |
| 187 | CH$_2$CF$_3$ | CH$_3$ | — | cyclopropyl |
| 188 | CH$_2$CH(CH$_3$)$_2$ | CH$_3$ | — | cyclopropyl |
| 189 | CH$_2$C(CH$_3$)=CH$_2$ | CH$_3$ | — | cyclopropyl |
| 190 | CH$_2$C(Cl)=CH$_2$ | CH$_3$ | — | cyclopropyl |
| 191 | CH$_2$C(F)=CH$_2$ | CH$_3$ | — | cyclopropyl |
| 192 | CH$_2$C(CH$_3$)$_3$ | CH$_3$ | — | cyclopropyl |
| 193 | CH$_2$CH=CH$_2$ | CH$_3$ | — | cyclopropyl |
| 194 | CH$_2$cyclopropyl | CH$_3$ | — | cyclopropyl |
| 195 | CH$_2$(1-methylcyclopropyl) | CH$_3$ | — | cyclopropyl |
| 196 | CH$_2$(1-fluorocyclopropyl) | CH$_3$ | — | cyclopropyl |
| 197 | CH$_2$CF(CH$_3$)$_2$ | CH$_3$ | — | cyclopropyl |
| 198 | CH$_2$CF$_2$CH$_3$ | CH$_3$ | — | cyclopropyl |
| 199 | CH$_3$ | CH$_3$ | — | 1-methylcyclopropyl |
| 200 | CH$_2$CH$_3$ | CH$_3$ | — | 1-methylcyclopropyl |
| 201 | CH(CH$_3$)$_2$ | CH$_3$ | — | 1-methylcyclopropyl |
| 202 | C(CH$_3$)$_3$ | CH$_3$ | — | 1-methylcyclopropyl |
| 203 | CH$_2$CF$_3$ | CH$_3$ | — | 1-methylcyclopropyl |
| 204 | CH$_2$CH(CH$_3$)$_2$ | CH$_3$ | — | 1-methylcyclopropyl |
| 205 | CH$_2$C(CH$_3$)=CH$_2$ | CH$_3$ | — | 1-methylcyclopropyl |
| 206 | CH$_2$C(Cl)=CH$_2$ | CH$_3$ | — | 1-methylcyclopropyl |
| 207 | CH$_2$C(F)=CH$_2$ | CH$_3$ | — | 1-methylcyclopropyl |
| 208 | CH$_2$C(CH$_3$)$_3$ | CH$_3$ | — | 1-methylcyclopropyl |
| 209 | CH$_2$CH=CH$_2$ | CH$_3$ | — | 1-methylcyclopropyl |
| 210 | CH$_2$cyclopropyl | CH$_3$ | — | 1-methylcyclopropyl |
| 211 | CH$_2$(1-methylcyclopropyl) | CH$_3$ | — | 1-methylcyclopropyl |
| 212 | CH$_2$(1-fluorocyclopropyl) | CH$_3$ | — | 1-methylcyclopropyl |
| 213 | CH$_2$CF(CH$_3$)$_2$ | CH$_3$ | — | 1-methylcyclopropyl |
| 214 | CH$_2$CF$_2$CH$_3$ | CH$_3$ | — | 1-methylcyclopropyl |
| 215 | CH$_3$ | CH$_3$ | — | cyclobutyl |
| 216 | CH$_2$CH$_3$ | CH$_3$ | — | cyclobutyl |
| 217 | CH(CH$_3$)$_2$ | CH$_3$ | — | cyclobutyl |
| 218 | C(CH$_3$)$_3$ | CH$_3$ | — | cyclobutyl |
| 219 | CH$_2$CF$_3$ | CH$_3$ | — | cyclobutyl |
| 220 | CH$_2$CH(CH$_3$)$_2$ | CH$_3$ | — | cyclobutyl |
| 221 | CH$_2$C(CH$_3$)=CH$_2$ | CH$_3$ | — | cyclobutyl |
| 222 | CH$_2$C(Cl)=CH$_2$ | CH$_3$ | — | cyclobutyl |
| 223 | CH$_2$C(F)=CH$_2$ | CH$_3$ | — | cyclobutyl |
| 224 | CH$_2$C(CH$_3$)$_3$ | CH$_3$ | — | cyclobutyl |
| 225 | CH$_2$CH=CH$_2$ | CH$_3$ | — | cyclobutyl |
| 226 | CH$_2$cyclopropyl | CH$_3$ | — | cyclobutyl |
| 227 | CH$_2$(1-methylcyclopropyl) | CH$_3$ | — | cyclobutyl |
| 228 | CH$_2$(1-fluorocyclopropyl) | CH$_3$ | — | cyclobutyl |
| 229 | CH$_2$CF(CH$_3$)$_2$ | CH$_3$ | — | cyclobutyl |
| 230 | CH$_2$CF$_2$CH$_3$ | CH$_3$ | — | cyclobutyl |
| 231 | CH$_3$ | CH$_3$ | — | cyclopentyl |
| 232 | CH$_2$CH$_3$ | CH$_3$ | — | cyclopentyl |
| 233 | CH(CH$_3$)$_2$ | CH$_3$ | — | cyclopentyl |
| 234 | C(CH$_3$)$_3$ | CH$_3$ | — | cyclopentyl |
| 235 | CH$_2$CF$_3$ | CH$_3$ | — | cyclopentyl |
| 236 | CH$_2$CH(CH$_3$)$_2$ | CH$_3$ | — | cyclopentyl |
| 237 | CH$_2$C(CH$_3$)=CH$_2$ | CH$_3$ | — | cyclopentyl |
| 238 | CH$_2$C(Cl)=CH$_2$ | CH$_3$ | — | cyclopentyl |

TABLE Z-continued

| Entry | R₅ | R₆ | A | R₇ |
|---|---|---|---|---|
| 239 | CH₂C(F)=CH₂ | CH₃ | — | cyclopentyl |
| 240 | CH₂C(CH₃)₃ | CH₃ | — | cyclopentyl |
| 241 | CH₂CH=CH₂ | CH₃ | — | cyclopentyl |
| 242 | CH₂cyclopropyl | CH₃ | — | cyclopentyl |
| 243 | CH₂(1-methylcyclopropyl) | CH₃ | — | cyclopentyl |
| 244 | CH₂(1-fluorocyclopropyl) | CH₃ | — | cyclopentyl |
| 245 | CH₂CF(CH₃)₂ | CH₃ | — | cyclopentyl |
| 246 | CH₂CF₂CH₃ | CH₃ | — | cyclopentyl |
| 247 | CH₃ | CH₃ | — | cyclohexyl |
| 248 | CH₂CH₃ | CH₃ | — | cyclohexyl |
| 249 | CH(CH₃)₂ | CH₃ | — | cyclohexyl |
| 250 | C(CH₃)₃ | CH₃ | — | cyclohexyl |
| 251 | CH₂CF₃ | CH₃ | — | cyclohexyl |
| 252 | CH₂CH(CH₃)₂ | CH₃ | — | cyclohexyl |
| 253 | CH₂C(CH₃)=CH₂ | CH₃ | — | cyclohexyl |
| 254 | CH₂C(Cl)=CH₂ | CH₃ | — | cyclohexyl |
| 255 | CH₂C(F)=CH₂ | CH₃ | — | cyclohexyl |
| 256 | CH₂C(CH₃)₃ | CH₃ | — | cyclohexyl |
| 257 | CH₂CH=CH₂ | CH₃ | — | cyclohexyl |
| 258 | CH₂cyclopropyl | CH₃ | — | cyclohexyl |
| 259 | CH₂(1-methylcyclopropyl) | CH₃ | — | cyclohexyl |
| 260 | CH₂(1-fluorocyclopropyl) | CH₃ | — | cyclohexyl |
| 261 | CH₂CF(CH₃)₂ | CH₃ | — | cyclohexyl |
| 262 | CH₂CF₂CH₃ | CH₃ | — | cyclohexyl |
| 263 | CH₂CH₃ | CH₃ | CH₂ | CH(CH₃)₂ |
| 264 | CH(CH₃)₂ | CH₃ | CH₂ | CH(CH₃)₂ |
| 265 | C(CH₃)₃ | CH₃ | CH₂ | CH(CH₃)₂ |
| 266 | CH₂CF₃ | CH₃ | CH₂ | CH(CH₃)₂ |
| 267 | CH₂CH(CH₃)₂ | CH₃ | CH₂ | CH(CH₃)₂ |
| 268 | CH₂C(CH₃)=CH₂ | CH₃ | CH₂ | CH(CH₃)₂ |
| 269 | CH₂C(Cl)=CH₂ | CH₃ | CH₂ | CH(CH₃)₂ |
| 270 | CH₂C(F)=CH₂ | CH₃ | CH₂ | CH(CH₃)₂ |
| 271 | CH₂C(CH₃)₃ | CH₃ | CH₂ | CH(CH₃)₂ |
| 272 | CH₂CH=CH₂ | CH₃ | CH₂ | CH(CH₃)₂ |
| 273 | CH₂cyclopropyl | CH₃ | CH₂ | CH(CH₃)₂ |
| 274 | CH₂(1-methylcyclopropyl) | CH₃ | CH₂ | CH(CH₃)₂ |
| 275 | CH₂(1-fluorocyclopropyl) | CH₃ | CH₂ | CH(CH₃)₂ |
| 276 | CH₂CF(CH₃)₂ | CH₃ | CH₂ | CH(CH₃)₂ |
| 277 | CH₂CF₂CH₃ | CH₃ | CH₂ | CH(CH₃)₂ |
| 278 | CH₂CH₃ | CH₃ | CH₂ | C(CH₃)₃ |
| 279 | CH(CH₃)₂ | CH₃ | CH₂ | C(CH₃)₃ |
| 280 | C(CH₃)₃ | CH₃ | CH₂ | C(CH₃)₃ |
| 281 | CH₂CF₃ | CH₃ | CH₂ | C(CH₃)₃ |
| 282 | CH₂C(CH₃)=CH₂ | CH₃ | CH₂ | C(CH₃)₃ |
| 283 | CH₂C(Cl)=CH₂ | CH₃ | CH₂ | C(CH₃)₃ |
| 284 | CH₂C(F)=CH₂ | CH₃ | CH₂ | C(CH₃)₃ |
| 285 | CH₂C(CH₃)₃ | CH₃ | CH₂ | C(CH₃)₃ |
| 286 | CH₂CH=CH₂ | CH₃ | CH₂ | C(CH₃)₃ |
| 287 | CH₂cyclopropyl | CH₃ | CH₂ | C(CH₃)₃ |
| 288 | CH₂(1-methylcyclopropyl) | CH₃ | CH₂ | C(CH₃)₃ |
| 289 | CH₂(1-fluorocyclopropyl) | CH₃ | CH₂ | C(CH₃)₃ |
| 290 | CH₂CF(CH₃)₂ | CH₃ | CH₂ | C(CH₃)₃ |
| 291 | CH₂CF₂CH₃ | CH₃ | CH₂ | C(CH₃)₃ |
| 292 | CH₂CH₃ | CH₃ | CH₂ | C(CH₃)=CH₂ |
| 293 | C(CH₃)₃ | CH₃ | CH₂ | C(CH₃)=CH₂ |
| 294 | CH₂CF₃ | CH₃ | CH₂ | C(CH₃)=CH₂ |
| 295 | CH₂C(CH₃)=CH₂ | CH₃ | CH₂ | C(CH₃)=CH₂ |
| 296 | CH₂C(Cl)=CH₂ | CH₃ | CH₂ | C(CH₃)=CH₂ |
| 297 | CH₂C(F)=CH₂ | CH₃ | CH₂ | C(CH₃)=CH₂ |
| 298 | CH₂CH=OH₂ | CH₃ | CH₂ | C(CH₃)=CH₂ |
| 299 | CH₂cyclopropyl | CH₃ | CH₂ | C(CH₃)=CH₂ |
| 300 | CH₂(1-methylcyclopropyl) | CH₃ | CH₂ | C(CH₃)=CH₂ |
| 301 | CH₂(1-fluorocyclopropyl) | CH₃ | CH₂ | C(CH₃)=CH₂ |
| 302 | CH₂CF(CH₃)₂ | CH₃ | CH₂ | C(CH₃)=CH₂ |
| 303 | CH₂CF₂CH₃ | CH₃ | CH₂ | C(CH₃)=CH₂ |
| 304 | CH₂CH₃ | CH₃ | CH₂ | C(Cl)=CH₂ |
| 305 | CH(CH₃)₂ | CH₃ | CH₂ | C(Cl)=CH₂ |
| 306 | C(CH₃)₃ | CH₃ | CH₂ | C(Cl)=CH₂ |
| 307 | CH₂CF₃ | CH₃ | CH₂ | C(Cl)=CH₂ |
| 308 | CH₂C(Cl)=CH₂ | CH₃ | CH₂ | C(Cl)=CH₂ |
| 309 | CH₂C(F)=CH₂ | CH₃ | CH₂ | C(Cl)=CH₂ |
| 310 | CH₂CH=CH₂ | CH₃ | CH₂ | C(Cl)=CH₂ |
| 311 | CH₂cyclopropyl | CH₃ | CH₂ | C(Cl)=CH₂ |
| 312 | CH₂(1-methylcyclopropyl) | CH₃ | CH₂ | C(Cl)=CH₂ |
| 313 | CH₂(1-fluorocyclopropyl) | CH₃ | CH₂ | C(Cl)=CH₂ |
| 314 | CH₂CF(CH₃)₂ | CH₃ | CH₂ | C(Cl)=CH₂ |
| 315 | CH₂CF₂CH₃ | CH₃ | CH₂ | C(Cl)=CH₂ |
| 316 | CH₂CH₃ | CH₃ | CH₂ | C(CH₃)=CH(CH₃) |
| 317 | CH(CH₃)₂ | CH₃ | CH₂ | C(CH₃)=CH(CH₃) |
| 318 | C(CH₃)₃ | CH₃ | CH₂ | C(CH₃)=CH(CH₃) |
| 319 | CH₂CF₃ | CH₃ | CH₂ | C(CH₃)=CH(CH₃) |
| 320 | CH₂CH(CH₃)₂ | CH₃ | CH₂ | C(CH₃)=CH(CH₃) |
| 321 | CH₂C(CH₃)=CH₂ | CH₃ | CH₂ | C(CH₃)=CH(CH₃) |
| 322 | CH₂C(Cl)=CH₂ | CH₃ | CH₂ | C(CH₃)=CH(CH₃) |
| 323 | CH₂C(F)=CH₂ | CH₃ | CH₂ | C(CH₃)=CH(CH₃) |
| 324 | CH₂C(CH₃)₃ | CH₃ | CH₂ | C(CH₃)=CH(CH₃) |
| 325 | CH₂CH=CH₂ | CH₃ | CH₂ | C(CH₃)=CH(CH₃) |
| 326 | CH₂cyclopropyl | CH₃ | CH₂ | C(CH₃)=CH(CH₃) |
| 327 | CH₂(1-methylcyclopropyl) | CH₃ | CH₂ | C(CH₃)=CH(CH₃) |
| 328 | CH₂(1-fluorocyclopropyl) | CH₃ | CH₂ | C(CH₃)=CH(CH₃) |
| 329 | CH₂CF(CH₃)₂ | CH₃ | CH₂ | C(CH₃)=CH(CH₃) |
| 330 | CH₂CF₂CH₃ | CH₃ | CH₂ | C(CH₃)=CH(CH₃) |
| 331 | CH₂CH₃ | CH₃ | CH₂ | C(F)=C(CH₃)₂ |
| 332 | CH(CH₃)₂ | CH₃ | CH₂ | C(F)=C(CH₃)₂ |
| 333 | C(CH₃)₃ | CH₃ | CH₂ | C(F)=C(CH₃)₂ |
| 334 | CH₂CF₃ | CH₃ | CH₂ | C(F)=C(CH₃)₂ |
| 335 | CH₂CH(CH₃)₂ | CH₃ | CH₂ | C(F)=C(CH₃)₂ |
| 336 | CH₂C(CH₃)=CH₂ | CH₃ | CH₂ | C(F)=C(CH₃)₂ |
| 337 | CH₂C(Cl)=CH₂ | CH₃ | CH₂ | C(F)=C(CH₃)₂ |
| 338 | CH₂C(F)=CH₂ | CH₃ | CH₂ | C(F)=C(CH₃)₂ |
| 339 | CH₂C(CH₃)₃ | CH₃ | CH₂ | C(F)=C(CH₃)₂ |
| 340 | CH₂CH=CH₂ | CH₃ | CH₂ | C(F)=C(CH₃)₂ |
| 341 | CH₂cyclopropyl | CH₃ | CH₂ | C(F)=C(CH₃)₂ |
| 342 | CH₂(1-methylcyclopropyl) | CH₃ | CH₂ | C(F)=C(CH₃)₂ |
| 343 | CH₂(1-fluorocyclopropyl) | CH₃ | CH₂ | C(F)=C(CH₃)₂ |
| 344 | CH₂CF(CH₃)₂ | CH₃ | CH₂ | C(F)=C(CH₃)₂ |
| 345 | CH₂CF₂CH₃ | CH₃ | CH₂ | C(F)=C(CH₃)₂ |
| 346 | CH₂CH₃ | CH₃ | CH₂ | CH=C(CH₃)₂ |
| 347 | CH(CH₃)₂ | CH₃ | CH₂ | CH=C(CH₃)₂ |
| 348 | C(CH₃)₃ | CH₃ | CH₂ | CH=C(CH₃)₂ |
| 349 | CH₂CF₃ | CH₃ | CH₂ | CH=C(CH₃)₂ |
| 350 | CH₂CH(CH₃)₂ | CH₃ | CH₂ | CH=C(CH₃)₂ |
| 351 | CH₂C(CH₃)=CH₂ | CH₃ | CH₂ | CH=C(CH₃)₂ |
| 352 | CH₂C(Cl)=CH₂ | CH₃ | CH₂ | CH=C(CH₃)₂ |
| 353 | CH₂C(F)=CH₂ | CH₃ | CH₂ | CH=C(CH₃)₂ |
| 354 | CH₂C(CH₃)₃ | CH₃ | CH₂ | CH=C(CH₃)₂ |
| 355 | CH₂CH=CH₂ | CH₃ | CH₂ | CH=C(CH₃)₂ |
| 356 | CH₂cyclopropyl | CH₃ | CH₂ | CH=C(CH₃)₂ |
| 357 | CH₂(1-methylcyclopropyl) | CH₃ | CH₂ | CH=C(CH₃)₂ |
| 358 | CH₂(1-fluorocyclopropyl) | CH₃ | CH₂ | CH=C(CH₃)₂ |
| 359 | CH₂CF(CH₃)₂ | CH₃ | CH₂ | CH=C(CH₃)₂ |
| 360 | CH₂CF₂CH₃ | CH₃ | CH₂ | CH=C(CH₃)₂ |
| 361 | CH₂CH₃ | CH₃ | CH₂ | C(CH₃)=C(CH₃)₂ |
| 362 | CH(CH₃)₂ | CH₃ | CH₂ | C(CH₃)=C(CH₃)₂ |
| 363 | C(CH₃)₃ | CH₃ | CH₂ | C(CH₃)=C(CH₃)₂ |
| 364 | CH₂CF₃ | CH₃ | CH₂ | C(CH₃)=C(CH₃)₂ |
| 365 | CH₂CH(CH₃)₂ | CH₃ | CH₂ | C(CH₃)=C(CH₃)₂ |
| 366 | CH₂C(CH₃)=CH₂ | CH₃ | CH₂ | C(CH₃)=C(CH₃)₂ |
| 367 | CH₂C(Cl)=CH₂ | CH₃ | CH₂ | C(CH₃)=C(CH₃)₂ |
| 368 | CH₂C(F)=CH₂ | CH₃ | CH₂ | C(CH₃)=C(CH₃)₂ |
| 369 | CH₂C(CH₃)₃ | CH₃ | CH₂ | C(CH₃)=C(CH₃)₂ |
| 370 | CH₂CH=CH₂ | CH₃ | CH₂ | C(CH₃)=C(CH₃)₂ |
| 371 | CH₂cyclopropyl | CH₃ | CH₂ | C(CH₃)=C(CH₃)₂ |
| 372 | CH₂(1-methylcyclopropyl) | CH₃ | CH₂ | C(CH₃)=C(CH₃)₂ |
| 373 | CH₂(1-fluorocyclopropyl) | CH₃ | CH₂ | C(CH₃)=C(CH₃)₂ |
| 374 | CH₂CF(CH₃)₂ | CH₃ | CH₂ | C(CH₃)=C(CH₃)₂ |
| 375 | CH₂CF₂CH₃ | CH₃ | CH₂ | C(CH₃)=C(CH₃)₂ |
| 376 | CH₂CH₃ | CH₃ | CH₂ | CF₃ |
| 377 | CH(CH₃)₂ | CH₃ | CH₂ | CF₃ |
| 378 | C(CH₃)₃ | CH₃ | CH₂ | CF₃ |
| 379 | CH₂CF₃ | CH₃ | CH₂ | CF₃ |
| 380 | CH₂C(F)=CH₂ | CH₃ | CH₂ | CF₃ |
| 381 | CH₂CH=CH₂ | CH₃ | CH₂ | CF₃ |
| 382 | CH₂cyclopropyl | CH₃ | CH₂ | CF₃ |
| 383 | CH₂(1-methylcyclopropyl) | CH₃ | CH₂ | CF₃ |
| 384 | CH₂(1-fluorocyclopropyl) | CH₃ | CH₂ | CF₃ |
| 385 | CH₂CF(CH₃)₂ | CH₃ | CH₂ | CF₃ |
| 386 | CH₂CF₂CH₃ | CH₃ | CH₂ | CF₃ |
| 387 | CH₂CH₃ | CH₃ | CH₂ | cyclopropyl |
| 388 | CH(CH₃)₂ | CH₃ | CH₂ | cyclopropyl |
| 389 | C(CH₃)₃ | CH₃ | CH₂ | cyclopropyl |
| 390 | CH₂C(F)=CH₂ | CH₃ | CH₂ | cyclopropyl |
| 391 | CH₂CH=CH₂ | CH₃ | CH₂ | cyclopropyl |
| 392 | CH₂cyclopropyl | CH₃ | CH₂ | cyclopropyl |
| 393 | CH₂(1-methylcyclopropyl) | CH₃ | CH₂ | cyclopropyl |
| 394 | CH₂(1-fluorocyclopropyl) | CH₃ | CH₂ | cyclopropyl |

TABLE Z-continued

| Entry | $R_5$ | $R_6$ | A | $R_7$ |
|---|---|---|---|---|
| 395 | $CH_2CF(CH_3)_2$ | $CH_3$ | $CH_2$ | cyclopropyl |
| 396 | $CH_2CF_2CH_3$ | $CH_3$ | $CH_2$ | cyclopropyl |
| 397 | $CH_2CH_3$ | $CH_3$ | $CH_2$ | 1-methylcyclopropyl |
| 398 | $CH(CH_3)_2$ | $CH_3$ | $CH_2$ | 1-methylcyclopropyl |
| 399 | $C(CH_3)_3$ | $CH_3$ | $CH_2$ | 1-methylcyclopropyl |
| 400 | $CH_2C(F)=CH_2$ | $CH_3$ | $CH_2$ | 1-methylcyclopropyl |
| 401 | $CH_2CH=CH_2$ | $CH_3$ | $CH_2$ | 1-methylcyclopropyl |
| 402 | $CH_2$(1-methylcyclopropyl) | $CH_3$ | $CH_2$ | 1-methylcyclopropyl |
| 403 | $CH_2$(1-fluorocyclopropyl) | $CH_3$ | $CH_2$ | 1-methylcyclopropyl |
| 404 | $CH_2CF(CH_3)_2$ | $CH_3$ | $CH_2$ | 1-methylcyclopropyl |
| 405 | $CH_2CF_2CH_3$ | $CH_3$ | $CH_2$ | 1-methylcyclopropyl |
| 406 | $CH_3$ | $CH_3$ | $CH_2$ | cyclobutyl |
| 407 | $CH_2CH_3$ | $CH_3$ | $CH_2$ | cyclobutyl |
| 408 | $CH(CH_3)_2$ | $CH_3$ | $CH_2$ | cyclobutyl |
| 409 | $C(CH_3)_3$ | $CH_3$ | $CH_2$ | cyclobutyl |
| 410 | $CH_2CF_3$ | $CH_3$ | $CH_2$ | cyclobutyl |
| 411 | $CH_2CH(CH_3)_2$ | $CH_3$ | $CH_2$ | cyclobutyl |
| 412 | $CH_2C(CH_3)=CH_2$ | $CH_3$ | $CH_2$ | cyclobutyl |
| 413 | $CH_2C(Cl)=CH_2$ | $CH_3$ | $CH_2$ | cyclobutyl |
| 414 | $CH_2C(F)=CH_2$ | $CH_3$ | $CH_2$ | cyclobutyl |
| 415 | $CH_2C(CH_3)_3$ | $CH_3$ | $CH_2$ | cyclobutyl |
| 416 | $CH_2CH=CH_2$ | $CH_3$ | $CH_2$ | cyclobutyl |
| 417 | $CH_2$cyclopropyl | $CH_3$ | $CH_2$ | cyclobutyl |
| 418 | $CH_2$(1-methylcyclopropyl) | $CH_3$ | $CH_2$ | cyclobutyl |
| 419 | $CH_2$(1-fluorocyclopropyl) | $CH_3$ | $CH_2$ | cyclobutyl |
| 420 | $CH_2CF(CH_3)_2$ | $CH_3$ | $CH_2$ | cyclobutyl |
| 421 | $CH_2CF_2CH_3$ | $CH_3$ | $CH_2$ | cyclobutyl |
| 422 | $CH_3$ | $CH_3$ | $CH_2$ | cyclopentyl |
| 423 | $CH_2CH_3$ | $CH_3$ | $CH_2$ | cyclopentyl |
| 424 | $CH(CH_3)_2$ | $CH_3$ | $CH_2$ | cyclopentyl |
| 425 | $C(CH_3)_3$ | $CH_3$ | $CH_2$ | cyclopentyl |
| 426 | $CH_2CF_3$ | $CH_3$ | $CH_2$ | cyclopentyl |
| 427 | $CH_2CH(CH_3)_2$ | $CH_3$ | $CH_2$ | cyclopentyl |
| 428 | $CH_2C(CH_3)=CH_2$ | $CH_3$ | $CH_2$ | cyclopentyl |
| 429 | $CH_2C(Cl)=CH_2$ | $CH_3$ | $CH_2$ | cyclopentyl |
| 430 | $CH_2C(F)=CH_2$ | $CH_3$ | $CH_2$ | cyclopentyl |
| 431 | $CH_2C(CH_3)_3$ | $CH_3$ | $CH_2$ | cyclopentyl |
| 432 | $CH_2CH=CH_2$ | $CH_3$ | $CH_2$ | cyclopentyl |
| 433 | $CH_2$cyclopropyl | $CH_3$ | $CH_2$ | cyclopentyl |
| 434 | $CH_2$(1-methylcyclopropyl) | $CH_3$ | $CH_2$ | cyclopentyl |
| 435 | $CH_2$(1-fluorocyclopropyl) | $CH_3$ | $CH_2$ | cyclopentyl |
| 436 | $CH_2CF(CH_3)_2$ | $CH_3$ | $CH_2$ | cyclopentyl |
| 437 | $CH_2CF_2CH_3$ | $CH_3$ | $CH_2$ | cyclopentyl |
| 438 | $CH_3$ | $CH_3$ | $CH_2$ | cyclohexyl |
| 439 | $CH_2CH_3$ | $CH_3$ | $CH_2$ | cyclohexyl |
| 440 | $CH(CH_3)_2$ | $CH_3$ | $CH_2$ | cyclohexyl |
| 441 | $C(CH_3)_3$ | $CH_3$ | $CH_2$ | cyclohexyl |
| 442 | $CH_2CF_3$ | $CH_3$ | $CH_2$ | cyclohexyl |
| 443 | $CH_2CH(CH_3)_2$ | $CH_3$ | $CH_2$ | cyclohexyl |
| 444 | $CH_2C(CH_3)=CH_2$ | $CH_3$ | $CH_2$ | cyclohexyl |
| 445 | $CH_2C(Cl)=CH_2$ | $CH_3$ | $CH_2$ | cyclohexyl |
| 446 | $CH_2C(F)=CH_2$ | $CH_3$ | $CH_2$ | cyclohexyl |
| 447 | $CH_2C(CH_3)_3$ | $CH_3$ | $CH_2$ | cyclohexyl |
| 448 | $CH_2CH=CH_2$ | $CH_3$ | $CH_2$ | cyclohexyl |
| 449 | $CH_2$cyclopropyl | $CH_3$ | $CH_2$ | cyclohexyl |
| 450 | $CH_2$(1-methylcyclopropyl) | $CH_3$ | $CH_2$ | cyclohexyl |
| 451 | $CH_2$(1-fluorocyclopropyl) | $CH_3$ | $CH_2$ | cyclohexyl |
| 452 | $CH_2CF(CH_3)_2$ | $CH_3$ | $CH_2$ | cyclohexyl |
| 453 | $CH_2CF_2CH_3$ | $CH_3$ | $CH_2$ | cyclohexyl |
| 454 | $CH_3$ | $CH_3$ | $CH_2$ | $CH_2Ph$ |
| 455 | $CH_2CH_3$ | $CH_3$ | $CH_2$ | $CH_2Ph$ |
| 456 | $CH(CH_3)_2$ | $CH_3$ | $CH_2$ | $CH_2Ph$ |
| 457 | $C(CH_3)_3$ | $CH_3$ | $CH_2$ | $CH_2Ph$ |
| 458 | $CH_2CF_3$ | $CH_3$ | $CH_2$ | $CH_2Ph$ |
| 459 | $CH_2CH(CH_3)_2$ | $CH_3$ | $CH_2$ | $CH_2Ph$ |
| 460 | $CH_2C(CH_3)=CH_2$ | $CH_3$ | $CH_2$ | $CH_2Ph$ |
| 461 | $CH_2C(Cl)=CH_2$ | $CH_3$ | $CH_2$ | $CH_2Ph$ |
| 462 | $CH_2C(F)=CH_2$ | $CH_3$ | $CH_2$ | $CH_2Ph$ |
| 463 | $CH_2C(CH_3)_3$ | $CH_3$ | $CH_2$ | $CH_2Ph$ |
| 464 | $CH_2CH=CH_2$ | $CH_3$ | $CH_2$ | $CH_2Ph$ |
| 465 | $CH_2$cyclopropyl | $CH_3$ | $CH_2$ | $CH_2Ph$ |
| 466 | $CH_2$(1-methylcyclopropyl) | $CH_3$ | $CH_2$ | $CH_2Ph$ |
| 467 | $CH_2$(1-fluorocyclopropyl) | $CH_3$ | $CH_2$ | $CH_2Ph$ |
| 468 | $CH_2CF(CH_3)_2$ | $CH_3$ | $CH_2$ | $CH_2Ph$ |
| 469 | $CH_2CF_2CH_3$ | $CH_3$ | $CH_2$ | $CH_2Ph$ |
| 470 | $CH_3$ | $CH_3$ | $CH_2$ | $CH_2CH_2Ph$ |
| 471 | $CH_2CH_3$ | $CH_3$ | $CH_2$ | $CH_2CH_2Ph$ |
| 472 | $CH(CH_3)_2$ | $CH_3$ | $CH_2$ | $CH_2CH_2Ph$ |
| 473 | $C(CH_3)_3$ | $CH_3$ | $CH_2$ | $CH_2CH_2Ph$ |
| 474 | $CH_2CF_3$ | $CH_3$ | $CH_2$ | $CH_2CH_2Ph$ |
| 475 | $CH_2CH(CH_3)_2$ | $CH_3$ | $CH_2$ | $CH_2CH_2Ph$ |
| 476 | $CH_2C(CH_3)=CH_2$ | $CH_3$ | $CH_2$ | $CH_2CH_2Ph$ |
| 477 | $CH_2C(Cl)=CH_2$ | $CH_3$ | $CH_2$ | $CH_2CH_2Ph$ |
| 478 | $CH_2C(F)=CH_2$ | $CH_3$ | $CH_2$ | $CH_2CH_2Ph$ |
| 479 | $CH_2C(CH_3)_3$ | $CH_3$ | $CH_2$ | $CH_2CH_2Ph$ |
| 480 | $CH_2CH=CH_2$ | $CH_3$ | $CH_2$ | $CH_2CH_2Ph$ |
| 481 | $CH_2$cyclopropyl | $CH_3$ | $CH_2$ | $CH_2CH_2Ph$ |
| 482 | $CH_2$(1-methylcyclopropyl) | $CH_3$ | $CH_2$ | $CH_2CH_2Ph$ |
| 483 | $CH_2$(1-fluorocyclopropyl) | $CH_3$ | $CH_2$ | $CH_2CH_2Ph$ |
| 484 | $CH_2CF(CH_3)_2$ | $CH_3$ | $CH_2$ | $CH_2CH_2Ph$ |
| 485 | $CH_2CF_2CH_3$ | $CH_3$ | $CH_2$ | $CH_2CH_2Ph$ |
| 486 | $CH_2CH(CH_3)_2$ | $OCH_3$ | — | $CH_2C(CH_3)=CH_2$ |
| 487 | $CH_2CF_3$ | $OCH_3$ | — | $CH_2C(CH_3)=CH_2$ |
| 488 | $CH_2C(CH_3)=CH_2$ | $OCH_3$ | — | $CH_2C(CH_3)=CH_2$ |
| 489 | $CH_2$cyclopropyl | $OCH_3$ | — | $CH_2C(CH_3)=CH_2$ |
| 490 | $CH_2C(CH_3)_3$ | $OCH_3$ | — | $CH_2C(CH_3)=CH_2$ |
| 491 | $CH_2CH(CH_3)_2$ | $OCH_3$ | — | $CH_2CH(CH_3)_2$ |
| 492 | $CH_2CF_3$ | $OCH_3$ | — | $CH_2CH(CH_3)_2$ |
| 493 | $CH_2C(CH_3)=CH_2$ | $OCH_3$ | — | $CH_2CH(CH_3)_2$ |
| 494 | $CH_2$cyclopropyl | $OCH_3$ | — | $CH_2CH(CH_3)_2$ |
| 495 | $CH_2C(CH_3)_3$ | $OCH_3$ | — | $CH_2CH(CH_3)_2$ |
| 496 | $CH_2CH(CH_3)_2$ | $OCH_3$ | — | $CH_2C(CH_3)_3$ |
| 497 | $CH_2CF_3$ | $OCH_3$ | — | $CH_2C(CH_3)_3$ |
| 498 | $CH_2C(CH_3)=CH_2$ | $OCH_3$ | — | $CH_2C(CH_3)_3$ |
| 499 | $CH_2$cyclopropyl | $OCH_3$ | — | $CH_2C(CH_3)_3$ |
| 500 | $CH_2C(CH_3)_3$ | $OCH_3$ | — | $CH_2C(CH_3)_3$ |
| 501 | $CH_2CH(CH_3)_2$ | $OCH_3$ | — | $CH_2CF_3$ |
| 502 | $CH_2CF_3$ | $OCH_3$ | — | $CH_2CF_3$ |
| 503 | $CH_2C(CH_3)=CH_2$ | $OCH_3$ | — | $CH_2CF_3$ |
| 504 | $CH_2$cyclopropyl | $OCH_3$ | — | $CH_2CF_3$ |
| 505 | $CH_2C(CH_3)_3$ | $OCH_3$ | — | $CH_2CF_3$ |
| 506 | $CH_2CH(CH_3)_2$ | $OCH_3$ | — | $CH_2$cyclopropyl |
| 507 | $CH_2CF_3$ | $OCH_3$ | — | $CH_2$cyclopropyl |
| 508 | $CH_2C(CH_3)=CH_2$ | $OCH_3$ | — | $CH_2$cyclopropyl |
| 509 | $CH_2$cyclopropyl | $OCH_3$ | — | $CH_2$cyclopropyl |
| 510 | $CH_2C(CH_3)_3$ | $OCH_3$ | — | $CH_2$cyclopropyl |
| 511 | $CH_2CH(CH_3)_2$ | $CH_2OCH_3$ | — | $C(CH_3)=CH(CH_3)$ |
| 512 | $CH_2CF_3$ | $CH_2OCH_3$ | — | $C(CH_3)=CH(CH_3)$ |
| 513 | $CH_2C(CH_3)=CH_2$ | $CH_2OCH_3$ | — | $C(CH_3)=CH(CH_3)$ |
| 514 | $CH_2$cyclopropyl | $CH_2OCH_3$ | — | $C(CH_3)=CH(CH_3)$ |
| 515 | $CH_2C(CH_3)_3$ | $CH_2OCH_3$ | — | $C(CH_3)=CH(CH_3)$ |
| 516 | $CH_2CH(CH_3)_2$ | $CH_2OCH_3$ | — | $CH_2C(CH_3)=CH_2$ |
| 517 | $CH_2CF_3$ | $CH_2OCH_3$ | — | $CH_2C(CH_3)=CH_2$ |
| 518 | $CH_2C(CH_3)=CH_2$ | $CH_2OCH_3$ | — | $CH_2C(CH_3)=CH_2$ |
| 519 | $CH_2$cyclopropyl | $CH_2OCH_3$ | — | $CH_2C(CH_3)=CH_2$ |
| 520 | $CH_2C(CH_3)_3$ | $CH_2OCH_3$ | — | $CH_2C(CH_3)=CH_2$ |
| 521 | $CH_2CH(CH_3)_2$ | $CH_2OCH_3$ | — | $CH_2CH(CH_3)_2$ |
| 522 | $CH_2CF_3$ | $CH_2OCH_3$ | — | $CH_2CH(CH_3)_2$ |
| 523 | $CH_2C(CH_3)=CH_2$ | $CH_2OCH_3$ | — | $CH_2CH(CH_3)_2$ |
| 524 | $CH_2$cyclopropyl | $CH_2OCH_3$ | — | $CH_2CH(CH_3)_2$ |
| 525 | $CH_2C(CH_3)_3$ | $CH_2OCH_3$ | — | $CH_2CH(CH_3)_2$ |
| 526 | $CH_2CH(CH_3)_2$ | $CH_2OCH_3$ | — | $CH_2C(CH_3)_3$ |
| 527 | $CH_2CF_3$ | $CH_2OCH_3$ | — | $CH_2C(CH_3)_3$ |
| 528 | $CH_2C(CH_3)=CH_2$ | $CH_2OCH_3$ | — | $CH_2C(CH_3)_3$ |
| 529 | $CH_2$cyclopropyl | $CH_2OCH_3$ | — | $CH_2C(CH_3)_3$ |
| 530 | $CH_2C(CH_3)_3$ | $CH_2OCH_3$ | — | $CH_2C(CH_3)_3$ |
| 531 | $CH_2CH(CH_3)_2$ | $CH_2OCH_3$ | — | $CH_2CF_3$ |
| 532 | $CH_2CF_3$ | $CH_2OCH_3$ | — | $CH_2CF_3$ |
| 533 | $CH_2C(CH_3)=CH_2$ | $CH_2OCH_3$ | — | $CH_2CF_3$ |
| 534 | $CH_2$cyclopropyl | $CH_2OCH_3$ | — | $CH_2CF_3$ |
| 535 | $CH_2C(CH_3)_3$ | $CH_2OCH_3$ | — | $CH_2CF_3$ |
| 536 | $CH_2CH(CH_3)_2$ | $CH_2OCH_3$ | — | $CH_2$cyclopropyl |
| 537 | $CH_2CF_3$ | $CH_2OCH_3$ | — | $CH_2$cyclopropyl |
| 538 | $CH_2C(CH_3)=CH_2$ | $CH_2OCH_3$ | — | $CH_2$cyclopropyl |
| 539 | $CH_2$cyclopropyl | $CH_2OCH_3$ | — | $CH_2$cyclopropyl |
| 540 | $CH_2C(CH_3)_3$ | $CH_2OCH_3$ | — | $CH_2$cyclopropyl |
| 541 | $CH_2CH(CH_3)_2$ | $CH_2OCH_3$ | — | $C(CH_3)=CH(CH_3)$ |
| 542 | $CH_2CF_3$ | $CH_2OCH_3$ | — | $C(CH_3)=CH(CH_3)$ |
| 543 | $CH_2C(CH_3)=CH_2$ | $CH_2OCH_3$ | — | $C(CH_3)=CH(CH_3)$ |
| 544 | $CH_2$cyclopropyl | $CH_2OCH_3$ | — | $C(CH_3)=CH(CH_3)$ |
| 545 | $CH_2C(CH_3)_3$ | $CH_2OCH_3$ | — | $C(CH_3)=CH(CH_3)$ |

* In Table Z "—" means a direct bond.

Table A2 provides 545 compounds of formula (I-a) wherein $R_1$ is $CH_3$ and $R_2$, $R_3$ and $R_4$ are all H and wherein the values of $R_5$, $R_6$, A and $R_7$ are as defined in Table Z above.

Table A3 provides 545 compounds of formula (I-a) wherein $R_1$ is F and $R_2$, $R_3$ and $R_4$ are all H and wherein the values of $R_5$, $R_6$, A and $R_7$ are as defined in Table Z above.

Table A4 provides 545 compounds of formula (I-a) wherein $R_1$ is Cl and $R_2$, $R_3$ and $R_4$ are all H and wherein the values of $R_5$, $R_6$, A and $R_7$ are as defined in Table Z above.

Table A5 provides 545 compounds of formula (I-a) wherein $R_1$ is F, $R_2$ is F, $R_3$ and $R_4$ are both H and wherein the values of $R_5$, $R_6$, A and $R_7$ are as defined in Table Z above.

Table A6 provides 545 compounds of formula (I-a) wherein $R_1$ is F, $R_2$ is H, $R_3$ is $CH_3$ and $R_4$ is H and wherein the values of $R_5$, $R_6$, A and $R_7$ are as defined in Table Z above.

Table A7 provides 545 compounds of formula (I-a) wherein $R_1$ is F, $R_2$ is H, $R_3$ is H and $R_4$ is $CH_3$ and wherein the values of $R_5$, $R_6$, A and $R_7$ are as defined in Table Z above.

Table A8 provides 545 compounds of formula (I-b)

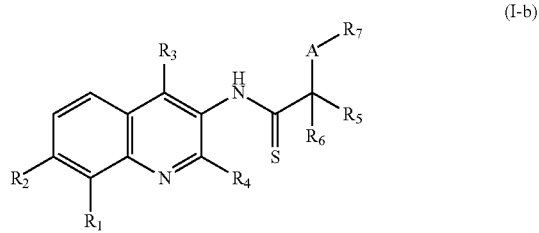

(I-b)

wherein $R_1$ is F, $R_2$, $R_3$ and $R_4$ are all H and wherein the values of $R_5$, $R_6$, A and $R_7$ are as defined in Table Z above.

Compounds of the present invention can be made as shown in the following schemes, in which, unless otherwise stated, the definition of each variable is as defined above for a compound of formula (I).

Among the various reported methods for preparing compounds of formula (I-a), wherein $R_1$, $R_2$, $R_3$, $R_4$, $R_5$, $R_6$, $R_7$ and A are as defined for compounds of formula (I), the most widely applied involve treatment of carboxylic acid (III), wherein $R_5$, $R_6$, $R_7$ and A are as defined for compounds of formula (I), with an activating agent like phosgene, thionyl chloride or oxalyl chloride or an amide coupling reagent like dicyclohexylcarbodiimide in an inert organic solvent like tetrahydrofuran (THF) or dimethylformamide (DMF) and reaction with an amine of formula (II), wherein $R_1$, $R_2$, $R_3$ and $R_4$ are as defined for compounds of formula (I), in the presence of a catalyst like dimethylaminopyridine as described in *Chem. Soc. Rev.*, 2009, 606-631 or *Tetrahedron* 2005, 10827-10852. This is shown in Scheme 1.

Scheme 1

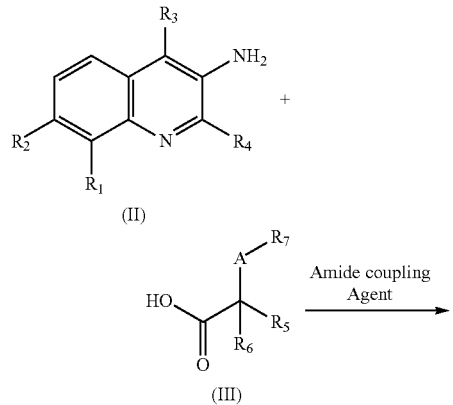

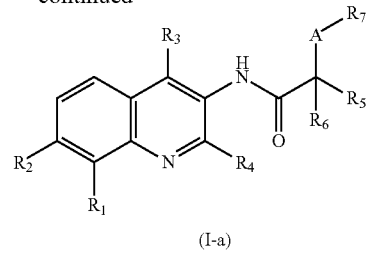

(I-a)

Compounds of formula (I-a), wherein $R_1$, $R_2$, $R_3$, $R_4$, $R_5$, $R_6$, $R_7$ and A are as defined for compounds of formula (I) can be prepared by the reaction of compounds of formula (II), wherein $R_1$, $R_2$, $R_3$ and $R_4$ are as defined for compounds of formula (I), and an ester of formula (IV) wherein $R_5$, $R_6$, $R_7$ and A are as defined for compounds of formula (I) and $R_{10}$ is $C_1$-$C_6$ alkyl or phenyl, with a Lewis acid such as trimethyl aluminium in an inert organic solvent like toluene under heating. This is shown in Scheme 2.

Scheme 2

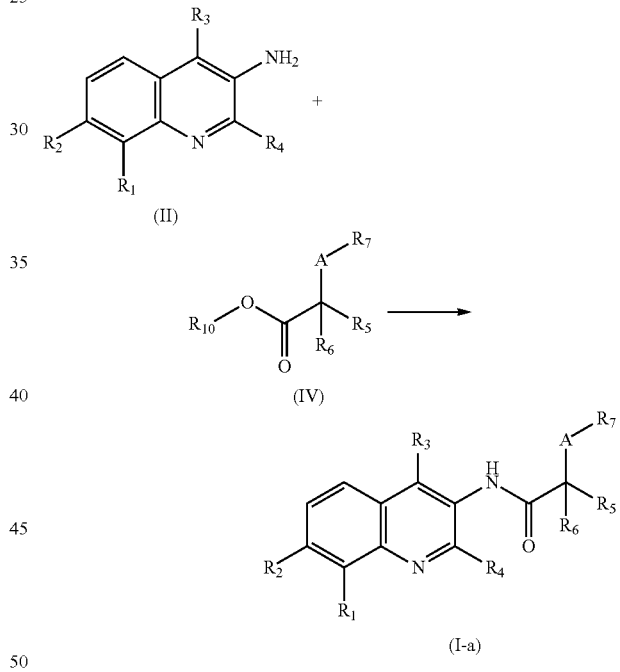

Alternatively, compounds of formula (I-a), wherein $R_1$, $R_2$, $R_3$, $R_4$, $R_5$, $R_6$, $R_7$ and A are as defined for compounds of formula (I), can be prepared by the coupling of compound (V), wherein $R_1$, $R_2$, $R_3$ and $R_4$ are as defined for compounds of formula (I) and Hal is halogen, preferably chloro, bromo or iodo, and compound (VI), wherein $R_5$, $R_6$, $R_7$ and A are as defined for compounds of formula (I), in the presence of a base such as cesium carbonate or sodium tertiary-butoxide in the presence of a transition metal catalyst such as a copper-based catalyst such as copper oxide, copper (I) acetylacetonate or copper (I) bromide-1,10-phenanthroline complex, a nickel catalyst such as Dichloro(1,3-bis(diphenylphosphino)propane)nickel or a palladium-based catalyst such as Chloro(2-dicyclohexylphosphino-2',4',6'-triisopropyl-1,1'-biphenyl)[2-(2'-amino-1,1'-biphenyl)]palladium (II), X-Phos aminobiphenyl palladium chloride precatalyst or [1,3-Bis(2,6-Diisopropylphenyl)imidazol-2-ylidene](3-chloropyridyl)palladium(II) dichloride in an aprotic solvent such as toluene or N,N-dimethylformamide at room temperature or while heating. This is shown in Scheme 3.

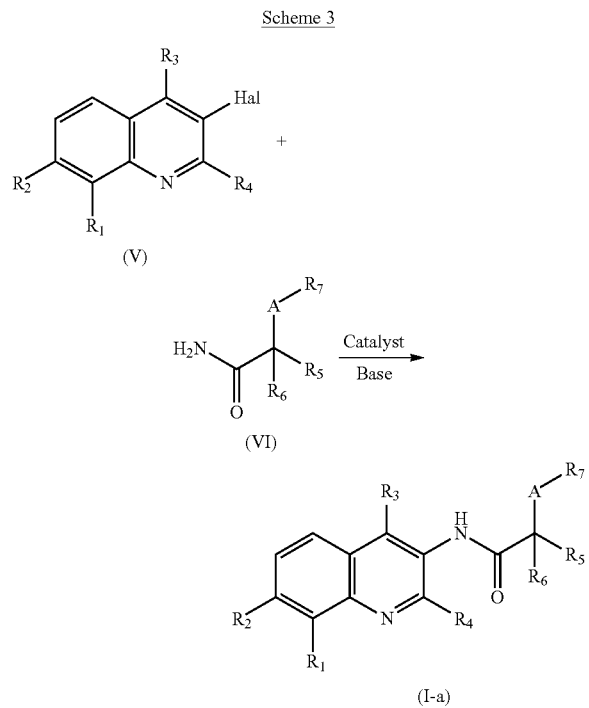

Compounds of formula (II), wherein $R_1$, $R_2$, $R_3$ and $R_4$ are as defined for compounds of formula (I) can be prepared by the coupling of compound (V), wherein $R_1$, $R_2$, $R_3$ and $R_4$ are as defined for compounds of formula (I) and Hal is halogen, preferably chloro, bromo or iodo, and ammonia, an ammonium salt (like ammonium hydroxide or ammonium acetate), in the presence of a base such as potassium phosphate, cesium carbonate or sodium tertiary-butoxide in the presence of a copper-based catalyst such as copper (I) acetylacetonate, copper oxide or copper (I) iodide in the presence of a ligand such as 1,10-phenanthroline or L-proline. Alternatively the reaction can be performed in the presence of a palladium or nickel based transition metal catalyst such as chloro(2-dicyclohexylphosphino-2',4',6'-triisopropyl-1,1'-biphenyl)[2-(2'-amino-1,1'-biphenyl)]palladium(II), X-Phos aminobiphenyl palladium chloride precatalyst or [1,3-Bis(2,6-Diisopropylphenyl)imidazol-2-ylidene](3-chloropyridyl) palladium(II) dichloride or Nickel dicyclooctadiene in combination with Josiphos SL-J003-1 as ligand. The reaction can be carried out in various aprotic solvent such as toluene, dioxane or N,N-dimethylformamide at room temperature or while heating. For instance the preparation of similar compounds has been described in *Organic Letters* 2016, 18(6), 1442-1445. This is shown in Scheme 4.

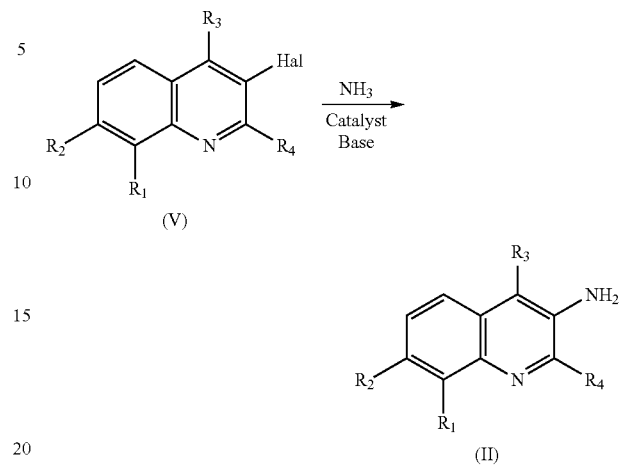

Alternatively compounds of formula (II) wherein $R_1$, $R_2$, $R_3$ and $R_4$ are as defined for compounds of formula (I), can be prepared by the coupling of compound (V), wherein $R_1$, $R_2$, $R_3$ and $R_4$ are as defined for compounds of formula (I) and Hal is halogen, preferably chloro, bromo or iodo, and a primary amine $R_{11}NH_2$ (VII) where $R_{11}$ is a protecting group such as benzyl or alkylcarbonyl, under transition metal catalysed conditions such as those described in Scheme 4, followed by deprotection of the group $R_{11}$, under various conditions such those described in *Greene's Protective Groups in Organic Synthesis* (Peter G. M. Wuts, Theodora W. Greene, John Wiley & Sons Ed.)

Compounds of formula (V), wherein $R_1$, $R_2$, $R_3$ and $R_4$ are as defined for compounds of formula (I) and Hal is halogen, preferably chloro, bromo or iodo can be prepared by treatment of compounds of formula (VIII), where $R_1$, $R_2$, $R_3$ and $R_4$ are as defined for compounds of formula (I), with a halogenating agent like N-iodosuccinimide, bromine or chlorine in an inert solvent such as acetonitrile or acetic acid at room temperature or while heating as described in WO 2005113539 or JP 2001322979. Alternatively, compounds of formula (V), wherein $R_1$, $R_2$, $R_3$ and $R_4$ are as defined for compounds of formula (I) and Hal is halogen, preferably chloro, bromo or iodo, can be prepared by treatment of propargylated anilines of formula (IX), wherein $R_1$, $R_2$, $R_3$ and $R_4$ are as defined for compounds of formula (I), with a halogenating agent like iodine or bromine in an inert solvent like acetonitrile and a base like sodium hydrogen carbonate at temperatures between 0° C. and 80° C. as described in Org. Lett. 2005, 763-766. This is shown in Scheme 5.

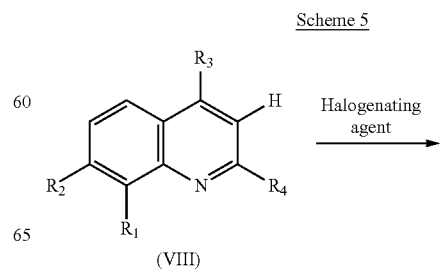

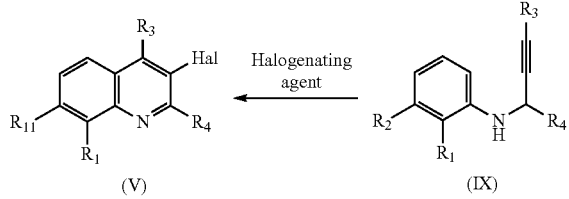

Compounds of formula (VIII) and compounds of formula (IX), wherein $R_1$, $R_2$, $R_3$ and $R_4$ are as defined for compounds of formula (I), can be prepared by using various synthesis techniques known to the person skilled in the art as described in *RSC Adv.* 2014, 4, 24463 or *March's Advanced Organic Chemistry*, Smith and March, 6th edition, Wiley, 2007.

Alternatively, compounds of formula (II) wherein $R_1$, $R_2$, $R_3$ and $R_4$ are as defined for compounds of formula (I) can be also prepared from carboxylic acids of formula (X) through an intermediary isocyanate of formula (XI) which can be hydrolyzed with aqueous acid or base at temperatures between 0° C. and 100° C. as shown in scheme 6.

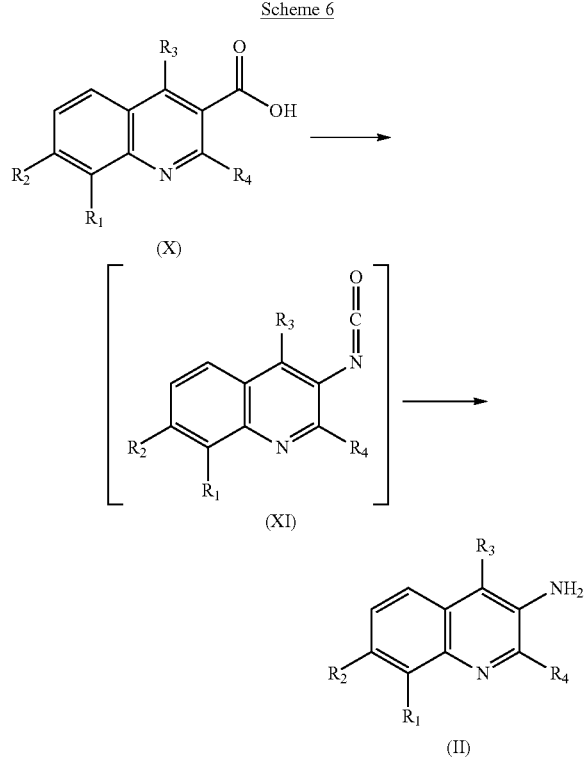

Among the various protocols reported for the transformation of acid (X) to isocyanate (XI), the following have found wide spread application:

1) Treatment of acid (X) with diphenylphosphoryl azide and an amine base like tributylamine in an inert organic solvent like toluene at temperatures between 50° C. and 120° C. to give isocyanate (XI) as described in *Aust. J. Chem.*, 1973, 1591-3.

2) Treatment of acid (X) with an activating agent like thionyl chloride or propylphosphonic anhydride in the presence of an azide source like sodium azide and an amine base like triethyl amine in an inert solvent like THF at temperatures between 20° C. and 100° C. as described in *Synthesis* 2011, 1477-1483.

3) Conversion of acid (X) to the corresponding hydroxamic acids which can then be treated with a dehydrating agent like para-toluenesulfonyl chloride and a base like triethylamine in an inert organic solvent like toluene at temperatures between 20° C. and 120° C.

4) Conversion of acid (X) to the corresponding primary carboxamide which can then be treated with an oxidizing agent such as diacetoxyiodobenzene and an acid such as trifluoroacetic acid or para-toluenesulfonic acid in a solvent like acetonitrile at temperatures between 0° C. and 100° C. as described in *J. Org. Chem.* 1984, 4212-4216.

5) Conversion of acid (X) to the corresponding primary carboxamide which can then be treated with an oxidizing agent such as bromine and a base such as sodium hydroxide in a solvent like water or methanol at temperatures between 0° C. and 100° C.

Carboxylic acids of formula (X) wherein $R_1$, $R_2$, $R_3$ and $R_4$ are as defined for compounds of formula (I) can be prepared by various methods as shown in Scheme 7 and many are commercially available.

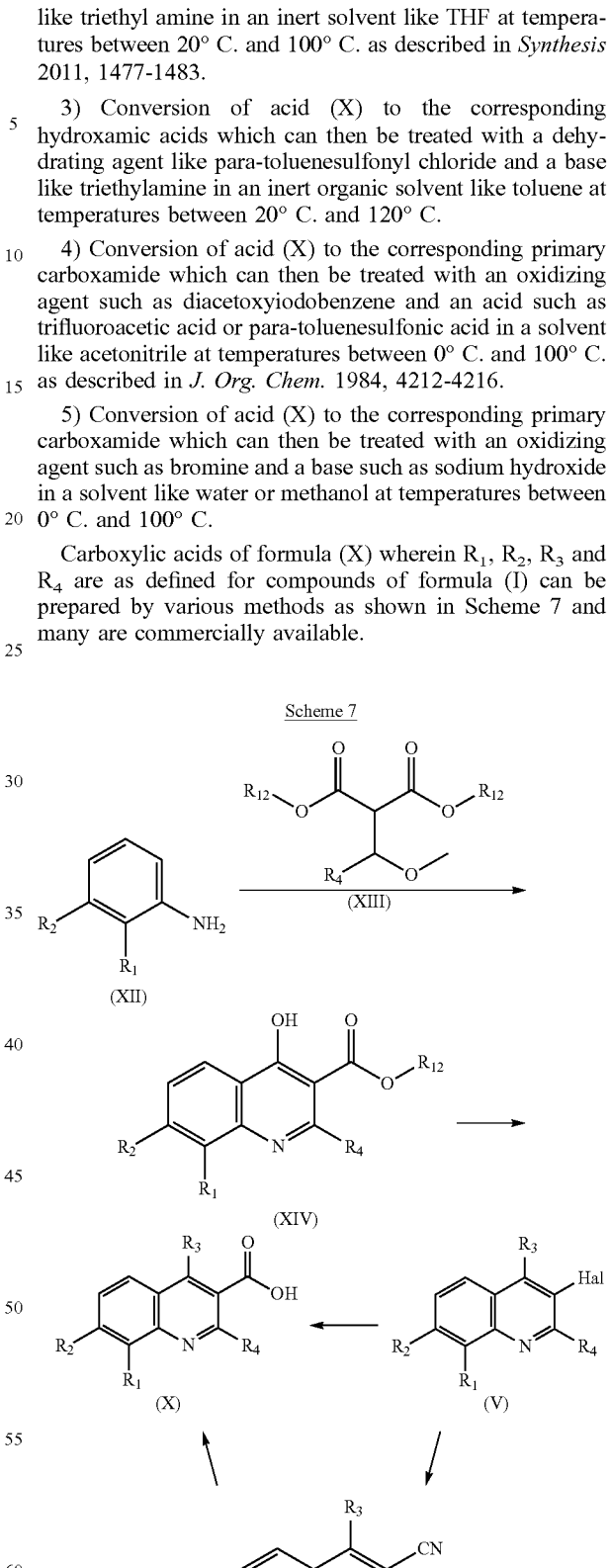

Among the many reported methods for their preparation, the following have been widely applied:

1) Transformation of anilines of formula (XII) to quinolones of formula (XIV) by reaction with a malonate derivative of formula (XIII), where in $R_{12}$ is C1-C6 alkyl and $R_4$ is as defined for compounds of formula (I), in an inert solvent like diphenyl ether at temperatures between 100° C. and 260° C. as described in US 20070015758, followed by well-known functional group interconversion which is generally known to a person skilled in the art and also described in WO 2007133637.

2) Transformation of compounds of formula (V) to organometallic intermediates by lithium-halogen exchange with an alkyl lithium reagent like s-butyl lithium or magnesium-halogen exchange with tri n-butyl magnesate in an ethereal solvent like THF at temperatures between −90° C. and +20° C. and subsequent reaction with $CO_2$.

3) Transformation of compounds of formula (V) in the presence of a carbon monoxide source, a base like triethylamine, water or an equivalent thereof and a suitably ligated transition metal catalyst containing for example palladium as described in J. Am. Chem. Soc. 2013, 2891-2894 (and references therein) or *Tetrahedron* 2003, 8629-8640.4) Hydrolysis of a compound of formula (XV) under basic or acidic aqueous conditions.

As shown in scheme 7, compounds of formula (XV) can be prepared from compounds of formula (V) by treatment with a cyanide source like zinc cyanide in the presence of a palladium, nickel or copper catalyst in an inert solvent like DMF at temperatures between 20° C. and 150° C. as described in J. Org. Chem. 2011, 665-668 or *Bull. Chem. Soc. Jpn.* 1993, 2776-8.

Among the various reported methods for preparing compounds of formula (VI), wherein $R_5$, $R_6$, $R_7$ and A are as defined for compounds of formula (I), the most widely applied involve treatment of carboxylic acid (III), wherein $R_5$, $R_6$, $R_7$ and A are as defined for compounds of formula (I), with an activating agent like phosgene, thionyl chloride or oxalyl chloride or an amide coupling reagent like dicyclohexylcarbodiimide in an inert organic solvent like tetrahydrofuran (THF) and reaction with ammonia or an ammonium salt such as ammonium chloride or ammonium hydroxide in the presence or absence of a catalyst like dimethylaminopyridine as described in *Chem. Soc. Rev.*, 2009, 606-631 or *Tetrahedron* 2005, 10827-10852. This is shown in Scheme 8.

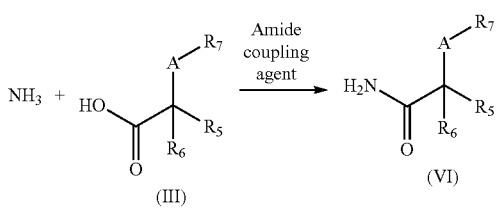

A person skilled in the art will appreciate that carboxylic acids of formula (III) can be prepared from the corresponding esters. Similarly a person skilled in the art will appreciate that the alpha position of these esters can be functionalized by deprotonation with a strong base like lithium diisopropylamine in an inert solvent like THF at temperatures between −78° C. and 20° C. followed by reaction with an electrophilic reagent like an alkyl iodide as described in *March's Advanced Organic Chemistry*, Smith and March, 6$^{th}$ edition, Wiley, 2007. This reaction can be repeated and the introduced alkyl, alkenyl and alkynyl groups can be further functionalized by halogenation, cyclopropanation, oxidation or reduction, cross coupling (eg Sonogashira coupling) to prepare acid derivatives from commercially available esters.

As shown in scheme 11, compounds of general formula (I-b), wherein wherein $R_1$, $R_2$, $R_3$, $R_4$, $R_5$, $R_6$, $R_7$ and A are as defined for compounds of formula (I), can be prepared from compounds of general formula (I-a), wherein $R_1$, $R_2$, $R_3$, $R_4$, $R_5$, $R_6$, $R_7$ and A are as defined for compounds of formula (I), by treatment with a deoxothionating agent like $P_4S_{10}$ or Lawesson reagent in an inert organic solvent like toluene at temperatures between 20° C. and 150° C.

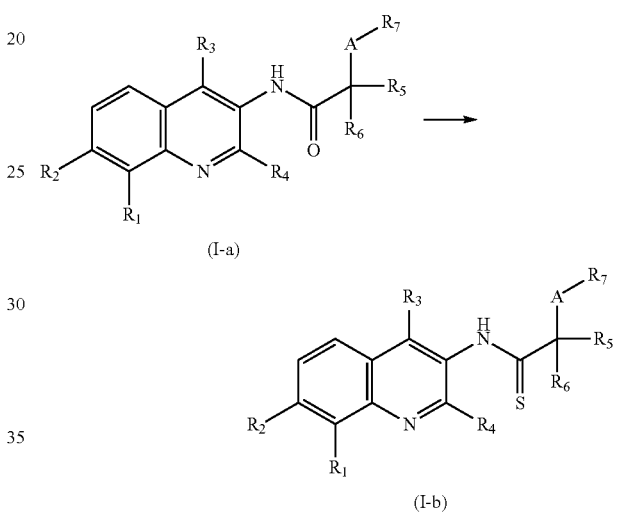

Alternatively, the compounds of formula (I-a) wherein $R_1$, $R_2$, $R_3$, $R_4$, $R_5$, $R_6$, $R_7$ and A are as defined for compounds of formula (I), can be obtained by transformation of another, closely related, compound of formula (I-a) using standard synthesis techniques known to the person skilled in the art. Non-exhaustive examples include oxidation reactions, reduction reactions, hydrolysis reactions, coupling reactions, aromatic nucleophilic or electrophilic substitution reactions, nucleophilic substitution reactions, nucleophilic addition reactions, olefination reactions, oxime formation, alkylation, cyclopropanation and halogenation reactions.

Certain intermediates described in the above schemes are novel and as such form a further aspect of the invention.

The compounds of formula (I) can be used in the agricultural sector and related fields of use e.g. as active ingredients for controlling plant pests or on non-living materials for control of spoilage microorganisms or organisms potentially harmful to man. The novel compounds are distinguished by excellent activity at low rates of application, by being well tolerated by plants and by being environmentally safe. They have very useful curative, preventive and systemic properties and may be used for protecting numerous cultivated plants. The compounds of formula (I) can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula (I) as fungicide. The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

It is also possible to use compounds of formula (I) as dressing agents for the treatment of plant propagation material, e.g., seed, such as fruits, tubers or grains, or plant cuttings (for example rice), for the protection against fungal infections as well as against phytopathogenic fungi occurring in the soil. The propagation material can be treated with a composition comprising a compound of formula (I) before planting: seed, for example, can be dressed before being sown. The compounds of formula (I) can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

Furthermore the compounds according to present invention can be used for controlling fungi in related areas, for example in the protection of technical materials, including wood and wood related technical products, in food storage, in hygiene management.

In addition, the invention could be used to protect non-living materials from fungal attack, e.g. lumber, wall boards and paint.

Compounds of formula (I) and fungicidal compositions containing them may be used to control plant diseases caused by a broad spectrum of fungal plant pathogens. They are effective in controlling a broad spectrum of plant diseases, such as foliar pathogens of ornamental, turf, vegetable, field, cereal, and fruit crops.

These fungi and fungal vectors of disease, as well as phytopathogenic bacteria and viruses, which may be controlled are for example:

*Absidia corymbifera*, *Alternaria* spp, *Aphanomyces* spp, *Ascochyta* spp, *Aspergillus* spp. including *A. flavus*, *A. fumigatus*, *A. nidulans*, *A. niger*, *A. terrus*, *Aureobasidium* spp. including *A. pullulans*, *Blastomyces dermatitidis*, *Blumeria graminis*, *Bremia lactucae*, *Botryosphaeria* spp. including *B. dothidea*, *B. obtusa*, *Botrytis* spp. including *B. cinerea*, *Candida* spp. including *C. albicans*, *C. glabrata*, *C. krusei*, *C. lusitaniae*, *C. parapsilosis*, *C. tropicalis*, *Cephaloascus fragrans*, *Ceratocystis* spp, *Cercospora* spp. including *C. arachidicola*, *Cercosporidium personatum*, *Cladosporium* spp, *Claviceps purpurea*, *Coccidioides immitis*, *Cochliobolus* spp, *Colletotrichum* spp. including *C. musae*, *Cryptococcus neoformans*, *Diaporthe* spp, *Didymella* spp, *Drechslera* spp, *Elsinoe* spp, *Epidermophyton* spp, *Erwinia amylovora*, *Erysiphe* spp. including *E. cichoracearum*, *Eutypa lata*, *Fusarium* spp. including *F. culmorum*, *F. graminearum*, *F. langsethiae*, *F. moniliforme*, *F. oxysporum*, *F. proliferatum*, *F. subglutinans*, *F. solani*, *Gaeumannomyces graminis*, *Gibberella fujikuroi*, *Gloeodes pomigena*, *Gloeosporium musarum*, *Glomerella cingulate*, *Guignardia bidwellii*, *Gymnosporangium juniperi-virginianae*, *Helminthosporium* spp, *Hemileia* spp, *Histoplasma* spp. including *H. capsulatum*, *Laetisaria fuciformis*, *Leptographium lindbergi*, *Leveillula taurica*, *Lophodermium seditiosum*, *Microdochium nivale*, *Microsporum* spp, *Monilinia* spp, *Mucor* spp, *Mycosphaerella* spp. including *M. graminicola*, *M. pomi*, *Oncobasidium theobromaeon*, *Ophiostoma piceae*, *Paracoccidioides* spp, *Penicillium* spp. including *P. digitatum*, *P. italicum*, *Petriellidium* spp, *Peronosclerospora* spp. Including *P. maydis*, *P. philippinensis* and *P. sorghi*, *Peronospora* spp, *Phaeosphaeria nodorum*, *Phakopsora pachyrhizi*, *Phellinus igniarus*, *Phialophora* spp, *Phoma* spp, *Phomopsis viticola*, *Phytophthora* spp. including *P. infestans*, Plasmopara spp. including *P. halstedii*, *P. viticola*, *Pleospora* spp., *Podosphaera* spp. including *P. leucotricha*, *Polymyxa graminis*, *Polymyxa betae*, *Pseudocercosporella herpotrichoides*, *Pseudomonas* spp, *Pseudoperonospora* spp. including *P. cubensis*, *P. humuli*, *Pseudopeziza tracheiphila*, *Puccinia* Spp. including *P. hordei*, *P. recondita*, *P. striiformis*, *P. triticina*, *Pyrenopeziza* spp, *Pyrenophora* spp, *Pyricularia* spp. including *P. oryzae*, *Pythium* spp. including *P. ultimum*, *Ramularia* spp, *Rhizoctonia* spp, *Rhizomucor pusillus*, *Rhizopus arrhizus*, *Rhynchosporium* spp, *Scedosporium* spp. including *S. apiospermum* and *S. prolificans*, *Schizothyrium pomi*,

*Sclerotinia* spp, *Sclerotium* spp, *Septoria* spp, including *S. nodorum*, *S. tritici*, *Sphaerotheca macularis*, *Sphaerotheca fusca* (*Sphaerotheca fuliginea*), *Sporothorix* spp, *Stagonospora nodorum*, *Stemphylium* spp., *Stereum hirsutum*, *Thanatephorus cucumeris*, *Thielaviopsis basicola*, *Tilletia* spp, *Trichoderma* spp. including *T. harzianum*, *T. pseudokoningii*, *T. viride*,

*Trichophyton* spp, *Typhula* spp, *Uncinula necator*, *Urocystis* spp, *Ustilago* spp, *Venturia* spp. including *V. inaequalis*, *Verticillium* spp, and *Xanthomonas* spp.

In particular, compounds of formula (I) and fungicidal compositions containing them may be used to control plant diseases caused by a broad spectrum of fungal plant pathogens in the Basidiomycete, Ascomycete, Oomycete and/or Deuteromycete, Blasocladiomycete, Chrytidiomycete, Glomeromycete and/or Mucoromycete classes.

These pathogens may include:

Oomycetes, including Phytophthora diseases such as those caused by *Phytophthora capsici*, *Phytophthora infestans*, *Phytophthora sojae*, *Phytophthora fragariae*, *Phytophthora nicotianae*, *Phytophthora cinnamomi*, *Phytophthora citricola*, *Phytophthora citrophthora* and *Phytophthora erythroseptica*; Pythium diseases such as those caused by *Pythium aphanidermatum*, *Pythium arrhenomanes*, *Pythium graminicola*, *Pythium irregulare* and *Pythium ultimum*; diseases caused by Peronosporales such as *Peronospora destructor*, *Peronospora parasitica*, *Plasmopara viticola*, *Plasmopara halstedii*, *Pseudoperonospora cubensis*, *Albugo candida*, *Sclerophthora macrospora* and *Bremia lactucae*; and others such as *Aphanomyces cochlioides*, *Labyrinthula zosterae*, *Peronosclerospora sorghi* and *Sclerospora graminicola*.

Ascomycetes, including blotch, spot, blast or blight diseases and/or rots for example those caused by Pleosporales such as *Stemphylium solani*, *Stagonospora tainanensis*, *Spilocaea oleaginea*, *Setosphaeria turcica*, *Pyrenochaeta lycoperisici*, *Pleospora herbarum*, *Phoma destructiva*, *Phaeosphaeria herpotrichoides*, *Phaeocryptocus gaeumannii*, *Ophiosphaerella graminicola*, *Ophiobolus graminis*, *Leptosphaeria maculans*, *Hendersonia creberrima*, *Helminthosporium triticirepentis*, *Setosphaeria turcica*, *Drechslera glycines*, *Didymella bryoniae*, *Cycloconium oleagineum*, *Corynespora cassiicola*, *Cochliobolus sativus*, *Bipolaris cactivora*, *Venturia inaequalis*, *Pyrenophora teres*, *Pyrenophora tritici-repentis*, *Alternaria alternata*, *Alternaria brassicicola*, *Alternaria solani* and *Alternaria tomatophila*, Capnodiales such as *Septoria tritici, Septoria nodorum, Septoria glycines, Cercospora arachidicola, Cercospora sojina, Cercospora zeae-maydis, Cercosporella capsellae* and *Cercosporella herpotrichoides, Cladosporium carpophilum, Cladosporium effusum, Passalora fulva, Cladosporium oxysporum, Dothistroma septosporum, Isariopsis clavispora, Mycosphaerella fijiensis, Mycosphaerella graminicola, Mycosphaerella koepkeii, Phaeoisariopsis bataticola, Pseudocercospora vitis, Pseudocercosporella herpotrichoides, Ramularia beticola, Ramularia collo-cygni,* Magnaporthales such as *Gaeumannomyces graminis, Magnaporthe grisea, Pyricularia oryzae,* Diaporthales such as *Anisogramma anomala, Apiognomonia errabunda, Cytospora platani, Diaporthe phaseolorum, Discula destructiva, Gnomonia fructicola, Greeneria uvicola, Melanconium juglandinum, Phomopsis viticola, Sirococcus clavigignenti-juglandacearum, Tubakia dryina, Dicarpella* spp., *Valsa ceratosperma,* and others such as *Actinothyrium graminis, Ascochyta pisi, Aspergillus flavus, Aspergillus fumigatus, Aspergillus nidulans, Asperisporium caricae, Blumeriella jaapii, Candida* spp., *Capnodium ramosum, Cephaloascus* spp., *Cephalosporium gramineum, Ceratocystis paradoxa, Chaetomium* spp., *Hymenoscyphus pseudoalbidus, Coccidioides* spp., *Cylindrosporium padi, Diplocarpon malae, Drepanopeziza campestris, Elsinoe ampelina, Epicoccum nigrum, Epidermophyton* spp., *Eutypa lata, Geotrichum candidum, Gibellina cerealis, Gloeocercospora sorghi, Gloeodes pomigena, Gloeosporium perennans; Gloeotinia temulenta, Griphospaeria corticola, Kabatiella lini, Leptographium microsporum, Leptosphaerulinia crassiasca, Lophodermium seditiosum, Marssonina graminicola, Microdochium nivale, Monilinia fructicola, Monographella albescens, Monosporascus cannonballus, Naemacyclus* spp., *Ophiostoma novo-ulmi, Paracoccidioides brasiliensis, Penicillium expansum, Pestalotia rhododendri, Petriellidium* spp., *Pezicula* spp., *Phialophora gregata, Phyllachora pomigena, Phymatotrichum omnivora, Physalospora abdita, Plectosporium tabacinum, Polyscytalum pustulans, Pseudopeziza medicaginis, Pyrenopeziza brassicae, Ramulispora sorghi, Rhabdocline pseudotsugae, Rhynchosporium secalis, Sacrocladium oryzae, Scedosporium* spp., *Schizothyrium pomi, Sclerotinia sclerotiorum, Sclerotinia minor; Sclerotium* spp., *Typhula ishikariensis, Seimatosporium mariae, Lepteutypa cupressi, Septocyta ruborum, Sphaceloma perseae, Sporonema phacidioides, Stigmina palmivora, Tapesia yallundae, Taphrina bullata, Thielviopsis basicola, Trichoseptoria fructigena, Zygophiala jamaicensis*; powdery mildew diseases for example those caused by Erysiphales such as *Blumeria graminis, Erysiphe polygoni, Uncinula necator, Sphaerotheca fuligena, Podosphaera leucotricha, Podospaera macularis Golovinomyces cichoracearum, Leveillula taurica, Microsphaera diffusa, Oidiopsis gossypii, Phyllactinia guttata and Oidium arachidis*; molds for example those caused by Botryosphaeriales such as *Dothiorella aromatica, Diplodia seriata, Guignardia bidwellii, Botrytis cinerea, Botryotinia allii, Botryotinia fabae, Fusicoccum amygdali, Lasiodiplodia theobromae, Macrophoma theicola, Macrophomina phaseolina, Phyllosticta cucurbitacearum*; anthracnoses for example those caused by Glommerelales such as *Colletotrichum gloeosporioides, Colletotrichum lagenarium, Colletotrichum gossypii, Glomerella cingulata,* and *Colletotrichum graminicola*; and wilts or blights for example those caused by Hypocreales such as *Acremonium strictum, Claviceps purpurea, Fusarium culmorum, Fusarium graminearum, Fusarium virguliforme, Fusarium oxysporum, Fusarium subglutinans, Fusarium oxysporum* f.sp. *cubense, Gerlachia nivale, Gibberella fujikuroi, Gibberella zeae, Gliocladium* spp., *Myrothecium verrucaria, Nectria ramulariae, Trichoderma viride, Trichothecium roseum,* and *Verticillium theobromae.*

Basidiomycetes, including smuts for example those caused by Ustilaginales such as *Ustilaginoidea virens, Ustilago nuda, Ustilago tritici, Ustilago zeae,* rusts for example those caused by Pucciniales such as *Cerotelium fici, Chrysomyxa arctostaphyli, Coleosporium ipomoeae, Hemileia vastatrix, Puccinia arachidis, Puccinia cacabata, Puccinia graminis, Puccinia recondita, Puccinia sorghi, Puccinia hordei, Puccinia striiformis* f.sp. *Hordei, Puccinia striiformis* f.sp. *Secalis, Pucciniastrum coryli,* or Uredinales such as *Cronartium ribicola, Gymnosporangium juniperi-viginianae, Melampsora medusae, Phakopsora pachyrhizi, Phragmidium mucronatum, Physopella ampelosidis, Tranzschelia discolor* and *Uromyces viciae-fabae*; and other rots and diseases such as those caused by *Cryptococcus* spp., *Exobasidium vexans, Marasmiellus inoderma, Mycena* spp., *Sphacelotheca reiliana, Typhula ishikariensis, Urocystis agropyri, Itersonilia perplexans, Corticium invisum, Laetisaria fuciformis, Waitea circinata, Rhizoctonia solani, Thanetephorus cucurmeris, Entyloma dahliae, Entylomella microspora, Neovossia moliniae* and *Tilletia caries.*

Blastocladiomycetes, such as *Physoderma maydis.*

Mucoromycetes, such as *Choanephora cucurbitarum; Mucor* spp.; *Rhizopus arrhizus,*

As well as diseases caused by other species and genera closely related to those listed above.

In addition to their fungicidal activity, the compounds and compositions comprising them may also have activity against bacteria such as *Erwinia amylovora, Erwinia caratovora, Xanthomonas campestris, Pseudomonas syringae, Strptomyces scabies* and other related species as well as certain protozoa.

Within the scope of present invention, target crops and/or useful plants to be protected typically comprise perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

The useful plants and/or target crops in accordance with the invention include conventional as well as genetically enhanced or engineered varieties such as, for example, insect resistant (e.g. Bt. and VIP varieties) as well as disease resistant, herbicide tolerant (e.g. glyphosate- and glufosinate-resistant maize varieties commercially available under the trade names RoundupReady® and LibertyLink®) and nematode tolerant varieties. By way of example, suitable genetically enhanced or engineered crop varieties include the Stoneville 5599BR cotton and Stoneville 4892BR cotton varieties.

The term "useful plants" and/or "target crops" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" and/or "target crops" is to be understood as including those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi. An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

The term "useful plants" and/or "target crops" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Toxins that can be expressed by transgenic plants include, for example, insecticidal proteins from *Bacillus cereus* or *Bacillus popilliae*; or insecticidal proteins from *Bacillus thuringiensis*, such as δ-endotoxins, e.g. CryIAb, CryIAc, CryIF, CryIFa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

Further, in the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO03/018810).

More examples of such toxins or transgenic plants capable of synthesising such toxins are disclosed, for example, in EP-A-0 374 753, WO93/07278, WO95/34656, EP-A-0 427 529, EP-A-451 878 and WO03/052073.

The processes for the preparation of such transgenic plants are generally known to the person skilled in the art and are described, for example, in the publications mentioned above. Cryl-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a CrylAb toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1 Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a CrylAb toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

Pesticidal agents referred to herein using their common name are known, for example, from "The Pesticide Manual", 15th Ed., British Crop Protection Council 2009.

The compounds of formula (I) may be used in unmodified form or, preferably, together with the adjuvants conventionally employed in the art of formulation. To this end they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g. for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

Suspension concentrates are aqueous formulations in which finely divided solid particles of the active compound are suspended. Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from 0.5% to 95% of the concentrate.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain from 5% to 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from 0.5% to 95% of the concentrate.

Granular formulations include both extrudates and relatively coarse particles and are usually applied without dilution to the area in which treatment is required. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations normally contain 5% to 25% of active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically 1 to 50 microns in diameter. The enclosed liquid typically constitutes 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre and preferably 1 to 2 millimetres in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Suitable agricultural adjuvants and carriers that are useful in formulating the compositions of the invention in the formulation types described above are well known to those skilled in the art.

Liquid carriers that can be employed include, for example, water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc., ethylene glycol, propylene glycol, glycerine and N-methyl-2-pyrrolidinone. Water is generally the carrier of choice for the dilution of concentrates.

Suitable solid carriers include, for example, talc, titanium dioxide, pyrophyllite clay, silica, attapulgite clay, kieselguhr, chalk, diatomaxeous earth, lime, calcium carbonate, bentonite clay, fuller's earth, cotton seed hulls, wheat flour, soybean flour, pumice, wood flour, walnut shell flour and lignin.

A broad range of surface-active agents are advantageously employed in both said liquid and solid compositions, especially those designed to be diluted with carrier before application. These agents, when used, normally comprise from 0.1% to 15% by weight of the formulation. They can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, anti-foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants and sticking agents.

In addition, further, other biocidally active ingredients or compositions may be combined with the compositions of the invention and used in the methods of the invention and applied simultaneously or sequentially with the compositions of the invention. When applied simultaneously, these further active ingredients may be formulated together with the compositions of the invention or mixed in, for example, the spray tank. These further biocidally active ingredients may be fungicides, herbicides, insecticides, bactericides, acaricides, nematicides and/or plant growth regulators.

In addition, the compositions of the invention may also be applied with one or more systemically acquired resistance inducers ("SAR" inducer). SAR inducers are known and described in, for example, U.S. Pat. No. 6,919,298 and include, for example, salicylates and the commercial SAR inducer acibenzolar-S-methyl.

The compounds of formula (I) are normally used in the form of compositions and can be applied to the crop area or plant to be treated, simultaneously or in succession with further compounds. These further compounds can be e.g. fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) may be used in the form of (fungicidal) compositions for controlling or protecting against phytopathogenic microorganisms, comprising as active ingredient at least one compound of formula (I) or of at least one preferred individual compound as above-defined, in free form or in agrochemically usable salt form, and at least one of the above-mentioned adjuvants.

The invention therefore provides a composition, preferably a fungicidal composition, comprising at least one compound formula (I) an agriculturally acceptable carrier and optionally an adjuvant. An agricultural acceptable carrier is for example a carrier that is suitable for agricultural use. Agricultural carriers are well known in the art. Preferably said composition may comprise at least one or more pesticidally active compounds, for example an additional fungicidal active ingredient in addition to the compound of formula (I).

The compound of formula (I) may be the sole active ingredient of a composition or it may be admixed with one or more additional active ingredients such as a pesticide, fungicide, synergist, herbicide or plant growth regulator where appropriate. An additional active ingredient may, in some cases, result in unexpected synergistic activities.

Examples of suitable additional active ingredients include the following: 1,2,4-thiadiazoles, 2,6-dinitroanilines, acyl-alanines, aliphatic nitrogenous compounds, amidines, aminopyrimidinols, anilides, anilino-pyrimidines, anthraquinones, antibiotics, aryl-phenylketones, benzamides, benzenesulfonamides, benzimidazoles, benzothiazoles, benzothiodiazoles, benzothiophenes, benzoylpyridines, benzthiadiazoles, benzylcarbamates, butylamines, carbamates, carboxamides, carpropamids, chloronitriles, cinnamic acid amides, copper containing compounds, cyanoacetamideoximes, cyanoacrylates, cyanoimidazoles, cyanomethylenethiazolidines, dicarbonitriles, dicarboxamides, dicarboximides, dimethylsulphamates, dinitrophenol carbonates, dinitrophenysl, dinitrophenyl crotonates, diphenyl phosphates, dithiino compounds, dithiocarbamates, dithioethers, dithiolanes, ethyl-amino-thiazole carboxamides, ethyl-phosphonates, furan carboxamides, glucopyranosyls, glucopyranoxyls, glutaronitriles, guanidines, herbicides/plant growth regulatosr, hexopyranosyl antibiotics, hydroxy(2-amino)pyrimidines, hydroxyanilides, hydroxyisoxazoles, imidazoles, imidazolinones, insecticides/plant growth regulators, isobenzofuranones, isoxazolidinyl-pyridines, isoxazolines, maleimides, mandelic acid amides, mectin derivatives, morpholines, norpholines, n-phenyl carbamates, organotin compounds, oxathiin carboxamides, oxazoles, oxazolidine-diones, phenols, phenoxy quinolines, phenyl-acetamides, phenylamides, phenylbenzamides, phenyl-oxo-ethyl-thiophenes amides, phenylpyrroles, phenylureas, phosphorothiolates, phosphorus acids, phthalamic acids, phthalimides, picolinamides, piperazines, piperidines, plant extracts, polyoxins, propionamides, pthalimides, pyrazole-4-carboxamides, pyrazolinones, pyridazinones, pyridines, pyridine carboxamides, pyridinyl-ethyl benzamides, pyrimdinamines, pyrimidines, pyrimidine-amines, pyrimidione-hydrazone, pyrrolidines, pyrrolquinoliones, quinazolinones, quinolines, quinoline derivatives, quinoline-7-carboxylic acids, quinoxalines, spiroketalamines, strobilurins, sulfamoyl triazoles, sulphamides, tetrazolyloximes, thiadiazines, thiadiazole carboxamides, thiazole carboxanides, thiocyanates, thiophene carboxamides, toluamides, triazines, triazobenthiazoles, triazoles, triazole-thiones, triazolo-pyrimidylamine, valinamide carbamates, ammonium methyl phosphonates, arsenic-containing compounds, benyimidazolylcarbamates, carbonitriles, carboxanilides, carboximidamides, carboxylic phenylamides, diphenyl pyridines, furanilides, hydrazine carboxamides, imidazoline acetates, isophthalates, isoxazolones, mercury salts, organomercury compounds, organophosphates, oxazolidinediones, pentylsulfonyl benzenes, phenyl benzamides, phosphonothionates, phosphorothioates, pyridyl carboxamides, pyridyl furfuryl ethers, pyridyl methyl ethers, SDHIs, thiadiazinanethiones, thiazolidines.

Examples of suitable additional active ingredients also include the following: 3-difluoromethyl-1-methyl-1H-pyrazole-4-carboxylic acid (9-dichloromethylene-1,2,3,4-tetrahydro-1,4-methano-naphthalen-5-yl)-amide, 3-difluoromethyl-1-methyl-1H-pyrazole-4-carboxylic acid methoxy-[1-methyl-2-(2,4,6-trichlorophenyl)-ethyl]-amide, 1-methyl-3-difluoromethyl-1H-pyrazole-4-carboxylic acid (2-dichloromethylene-3-ethyl-1-methyl-indan-4-yl)-amide (1072957-71-1), 1-methyl-3-difluoromethyl-1H-pyrazole-4-carboxylic acid (4'-methylsulfanyl-biphenyl-2-yl)-amide, 1-methyl-3-difluoromethyl-4H-pyrazole-4-carboxylic acid [2-(2,4-dichloro-phenyl)-2-methoxy-1-methyl-ethyl]-amide, (5-Chloro-2,4-dimethyl-pyridin-3-yl)-(2,3,4-trimethoxy-6-methyl-phenyl)-methanone, (5-Bromo-4-chloro-2-methoxy-pyridin-3-yl)-(2,3,4-trimethoxy-6-methyl-phenyl)-methanone, 2-{2-[(E)-3-(2,6-Dichloro-phenyl)-1-methyl-prop-2-en-(E)-ylideneaminooxymethyl]-phenyl}-2-[(Z)-methoxyimino]-N-methyl-acetamide, 3-[5-(4-Chloro-phenyl)-2,3-dimethyl-isoxazolidin-3-yl]-pyridine, (E)-N-methyl-2-[2-(2,5-dimethylphenoxymethyl) phenyl]-2-methoxy-iminoacetamide, 4-bromo-2-cyano-N, N-dimethyl-6-trifluoromethylbenzimidazole-1-sulphonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide, N-allyl-4,5,-dimethyl-2-trimethylsilylthiophene-3-carboxamide, N—(I-cyano-1,2-dimethylpropyl)-2-(2,4-dichlorophenoxy) propionamide, N-(2-methoxy-5-pyridyl)-cyclopropane carboxamide, (.+−.)-cis-1-(4-chlorophenyl)-2-(1H-1,2,4-triazol-1-yl)-cycloheptanol, 2-(1-tert-butyl)-1-(2-chlorophenyl)-3-(1,2,4-triazol-1-yl)-propan-2-ol, 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one, methyl (E)-2-[2-[6-(2-cyanophenoxy) pyrimidin-4-yloxy]phenyl]3-methoxyacrylate, methyl (E)-2-[2-[6-(2-thioamidophenoxy)pyrimidin-4-yloxy]phenyl]-3-methoxyacrylate, methyl (E)-2-[2-[6-(2-fluorophenoxy) pyrimidin-4-yloxy]phenyl]-3-methoxyacrylate, methyl (E)-2-[2-[6-(2,6-difluorophenoxy)pyrimidin-4-yloxy]phenyl]-3-methoxyacrylate, methyl (E)-2-[2-[3-(pyrimidin-2-yloxy) phenoxy]phenyl]-3-methoxyacrylate, methyl (E)-2-[2-[3-(5-methylpyrimidin-2-yloxy)-phenoxy]phenyl]-3-methoxyacrylate, methyl (E)-2-[2-[3-(phenyl-sulphonyloxy)phenoxy]phenyl-3-methoxyacrylate, methyl (E)-2-[2-[3-(4-nitrophenoxy)phenoxy]phenyl]-3-methoxyacrylate, methyl (E)-2-[2-phenoxyphenyl]-3-methoxyacrylate, methyl (E)-2-[2-(3,5-dimethyl-benzoyl)pyrrol-1-yl]-3-methoxyacrylate, methyl (E)-2-[2-(3-methoxyphenoxy) phenyl]-3-methoxyacrylate, methyl (E)-2[2-(2-phenylethen-1-yl)-phenyl]-3-methoxyacrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl (E)-2-(2-[3-(alpha-hydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxy-phenoxy)phenyl]3-methoxyacrylate, methyl (E)-2-[2-(3-isopropyloxyphenoxy)

phenyl]-3-methoxyacrylate, methyl (E)-2-[2-[3-(2-fluorophenoxy)phenoxy]phenyl]-3-methoxyacrylate, methyl (E)-2-[2-(3-ethoxyphenoxy)phenoxy]phenyl]-3-methoxyacrylate, methyl (E)-2-[2-(4-tert-butyl-pyridin-2-yloxy)phenyl]-3-methoxyacrylate, methyl (E)-2-[2-[3-(3-cyanophenoxy)phenoxy]phenyl]-3-methoxyacrylate, methyl (E)-2-[2-[(3-methyl-pyridin-2-yloxymethyl)phenyl]-3-methoxyacrylate, methyl (E)-2-[2-[6-(2-methyl-phenoxy)pyrimidin-4-yloxy]phenyl]-3-methoxyacrylate, methyl (E)-2-[2-(5-bromo-pyridin-2-yloxymethyl)phenyl]-3-methoxyacrylate, methyl (E)-2-[2-(3-(3-iodopyridin-2-yloxy)phenoxy)phenyl]-3-methoxyacrylate, methyl (E)-2-[2-[6-(2-chloropyridin-3-yloxy)pyrimidin-4-yloxy]phenyl]-3-methoxyacrylate, methyl (E),(E)-2-[2-(5,6-dimethylpyrazin-2-ylmethyloximinomethyl)phenyl]-3-methoxyacrylate, methyl (E)-2-{2-[6-(6-methylpyridin-2-yloxy)pyrimidin-4-yloxy]phenyl}-3-methoxy-acrylate, methyl (E),(E)-2-{2-(3-methoxyphenyl)methyloximinomethyl]-phenyl}-3-methoxyacrylate, methyl (E)-2-{2-(6-(2-azidophenoxy)-pyrimidin-4-yloxy]phenyl}-3-methoxyacrylate, methyl (E),(E)-2-{2-[6-phenylpyrimidin-4-yl)-methyloximinomethyl]phenyl}-3-methoxyacrylate, methyl (E),(E)-2-{2-[(4-chlorophenyl)-methyloximinomethyl]-phenyl}-3-methoxyacrylate, methyl (E)-2-{2-[6-(2-n-propylphenoxy)-1,3,5-triazin-4-yloxy]phenyl}-3-methoxyacrylate, methyl (E),(E)-2-{2-[(3-nitrophenyl)methyloximinomethyl]phenyl}-3-methoxyacrylate, 3-chloro-7-(2-aza-2,7,7-trimethyl-oct-3-en-5-ine), 2,6-dichloro-N-(4-trifluoromethylbenzyl)-benzamide, 3-iodo-2-propinyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate; phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol, 5-hydroxy-2 (5H)-furanone; 4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, acibenzolar, acypetacs, alanycarb, albendazole, aldimorph, allicin, allyl alcohol, ametoctradin, amisulbrom, amobam, ampropylfos, anilazine, asomate, aureofungin, azaconazole, azafendin, azithiram, azoxystrobin, barium polysulfide, benalaxyl, benalaxyl-M, benodanil, benomyl, benquinox, bentaluron, benthiavalicarb, benthiazole, benzalkonium chloride, benzamacril, benzamorf, benzohydroxamic acid, benzovindiflupyr, berberine, bethoxazin, biloxazol, binapacryl, biphenyl, bitertanol, bithionol, bixafen, blasticidin-S, boscalid, bromothalonil, bromuconazole, bupirimate, buthiobate, butylamine calcium polysulfide, captafol, captan, carbamorph, carbendazim, carbendazim chlrhydrate, carboxin, carpropamid, carvone, CGA41396, CGA41397, chinomethionate, chitosan, chlobenthiazone, chloraniformethan, chloranil, chlorfenazole, chloroneb, chloropicrin, chlorothalonil, chlorozolinate, chlozolinate, climbazole, clotrimazole, clozylacon, copper containing compounds such as copper acetate, copper carbonate, copper hydroxide, copper naphthenate, copper oleate, copper oxychloride, copper oxyquinolate, copper silicate, copper sulphate, copper tallate, copper zinc chromate and Bordeaux mixture, cresol, cufraneb, cuprobam, cuprous oxide, cyazofamid, cyclafuramid, cycloheximide, cyflufenamid, cymoxanil, cypendazole, cyproconazole, cyprodinil, dazomet, debacarb, decafentin, dehydroacetic acid, di-2-pyridyl disulphide 1,1'-dioxide, dichlofluanid, diclomezine, dichlone, dicloran, dichlorophen, dichlozoline, diclobutrazol, diclocymet, diethofencarb, difenoconazole, difenzoquat, diflumetorim, O-di-iso-propyl-S-benzyl thiophosphate, dimefluazole, dimetachlone, dimetconazole, dimethomorph, dimethirimol, diniconazole, diniconazole-M, dinobuton, dinocap, dinocton, dinopenton, dinosulfon, dinoterbon, diphenylamine, dipyrithione, disulfiram, ditalimfos, dithianon, dithioether, dodecyl dimethyl ammonium chloride, dodemorph, dodicin, dodine, doguadine, drazoxolon, edifenphos, enestroburin, epoxiconazole, etaconazole, etem, ethaboxam, ethirimol, ethoxyquin, ethilicin, ethyl (Z)—N-benzyl-N([methyl (methyl-thioethylideneamino-oxycarbonyl) amino]thio)-ß-alaninate, etridiazole, famoxadone, fenamidone, fenaminosulf, fenapanil, fenarimol, fenbuconazole, fenfuram, fenhexamid, fenitropan, fenoxanil, fenpiclonil, fenpicoxamid, fenpropidin, fenpropimorph, fenpyrazamine, fentin acetate, fentin hydroxide, ferbam, ferimzone, fluazinam, fludioxonil, flumetover, flumorph, flupicolide, fluopyram, fluoroimide, flutrimazole, fluoxastrobin, fluquinconazole, flusilazole, flusulfamide, flutanil, flutolanil, flutriafol, fluxapyroxad, folpet, formaldehyde, fosetyl, fuberidazole, furalaxyl, furametpyr, furcarbanil, furconazole, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hydroxyisoxazole, hymexazole, imazalil, imazalil sulphate, imibenconazole, iminoctadine, iminoctadine triacetate, inezin, iodocarb, ipconazole, ipfentrifluconazole, iprobenfos, iprodione, iprovalicarb, isopropanylbutyl carbamate, isoprothiolane, isopyrazam, isotianil, isovaledione, izopamfos, kasugamycin, kresoxim-methyl, LY186054, LY211795, LY248908, mancozeb, mandipropamid, maneb, mebenil, mecarbinzid, mefenoxam, mefentrifluconazole, mepanipyrim, mepronil, mercuric chloride, mercurous chloride, meptyldinocap, metalaxyl, metalaxyl-M, metam, metazoxolon, metconazole, methasulfocarb, methfuroxam, methyl bromide, methyl iodide, methyl isothiocyanate, metiram, metiram-zinc, metominostrobin, metrafenone, metsulfovax, milneb, moroxydine, myclobutanil, myclozolin, nabam, natamycin, neoasozin, nickel dimethyldithiocarbamate, nitrostyrene, nitrothal-isopropyl, nuarimol, octhilinone, ofurace, organomercury compounds, orysastrobin, osthol, oxadixyl, oxasulfuron, oxathiapiprolin, oxine-copper, oxolinic acid, oxpoconazole, oxycarboxin, parinol, pefurazoate, penconazole, pencycuron, penflufen, pentachlorophenol, penthiopyrad, phenamacril, phenazin oxide, phosdiphen, phosetyl-AI, phosphorus acids, phthalide, picoxystrobin, piperalin, polycarbamate, polyoxin D, polyoxrim, polyram, probenazole, prochloraz, procymidone, propamidine, propamocarb, propiconazole, propineb, propionic acid, proquinazid, prothiocarb, prothioconazole, pydiflumetofen, pyracarbolid, pyraclostrobin, pyrametrostrobin, pyraoxystrobin, pyrazophos, pyribencarb, pyridinitril, pyrifenox, pyrimethanil, pyriofenone, pyroquilon, pyroxychlor, pyroxyfur, pyrrolnitrin, quaternary ammonium compounds, quinacetol, quinazamid, quinconazole, quinomethionate, quinoxyfen, quintozene, rabenzazole, santonin, sedaxane, silthiofam, simeconazole, sipconazole, sodium pentachlorophenate, spiroxamine, streptomycin, sulphur, sultropen, tebuconazole, tebfloquin, tecloftalam, tecnazene, tecoram, tetraconazole, thiabendazole, thiadifluor, thicyofen, thifluzamide, 2-(thiocyanomethylthio) benzothiazole, thiophanate-methyl, thioquinox, thiram, tiadinil, timibenconazole, tioxymid, tolclofos-methyl, tolylfluanid, triadimefon, triadimenol, triamiphos, triarimol, triazbutil, triazoxide, tricyclazole, tridemorph, trifloxystrobin, triflumazole, triforine, triflumizole, triticonazole, uniconazole, urbacide, validamycin, valifenalate, vapam, vinclozolin, zarilamid, zineb, ziram, and zoxamide.

The compounds of the invention may also be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. Nos. 5,478,855, 4,639,771 and DE-19520936.

The compounds of the invention may be used in combination with derivatives and analogues of the general class of dioxomorpholine antiparasitic agents as described in WO 96/15121 and also with anthelmintic active cyclic depsipeptides such as those described in WO 96/11945, WO 93/19053, WO 93/25543, EP 0 626 375, EP 0 382 173, WO 94/19334, EP 0 382 173, and EP 0 503 538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO 95/19363 or WO 04/72086, particularly the compounds disclosed therein.

Other examples of such biologically active compounds that the compounds of the invention may be used in combination with include but are not restricted to the following: Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195,RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Biological agents: *Bacillus thuringiensis* ssp *aizawai, kurstaki, Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

The following mixtures of the compounds of Formula (I) with active ingredients are preferred. The abbreviation "TX" means one compound selected from the group consisting of the compounds as represented in Tables A1 to A8 (above) or Table E (below):

an adjuvant selected from the group of substances consisting of petroleum oils (alternative name) (628)+TX, an acaricide selected from the group of substances consisting of 1,1-bis(4-chloro-phenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, broflanilide [1207727-04-5]+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin 1 (696)+TX, cinerin 11 (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S(1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin 1 (696)+TX, pyrethrin 11 (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, *Bacillus subtilis* var. *amyloliquefaciens* Strain FZB24 (available from Novozymes Biologicals Inc., 5400 Corporate Circle, Salem, Va. 24153, U.S.A. and known under the trade name Taegro®)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (I U PAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec- 9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure B$_1$ (alternative name) (839)+TX, trimedlure B$_2$ (alternative name) (839)+TX, trimedlure C (alternative name) (839) and trunc-call (alternative name) [CCN]+TX, an insect repellent selected from the group of substances consisting of 2-(octylthio)-ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquinbutyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin 1 (696)+TX, pyrethrin 11 (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, bencloth-iaz [CCN]+TX, benomyl (62)+TX, butylpyridaben (alternative name)+TX, cadusa thiazolidines fos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)-ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of ametoctradin [865318-97-4]+TX, amisulbrom [348635-87-0]+TX, azaconazole [60207-31-0]+TX, benzovindiflupyr [1072957-71-1]+TX, bitertanol [70585-36-3]+TX, bixafen [581809-46-3]+TX, bromuconazole [116255-48-2]+TX, coumoxystrobin [850881-70-8]+TX, cyproconazole [94361-06-5]+TX, difenoconazole [119446-68-3]+TX, diniconazole [83657-24-3]+TX, enoxastrobin [238410-11-2]+TX, epoxiconazole [106325-08-0]+TX, fenbuconazole [114369-43-6]+TX, fenpyrazamine [473798-59-3]+TX, fluquinconazole [136426-54-5]+TX, flusilazole [85509-19-9]+TX, flutriafol [76674-21-0]+TX, fluxapyroxad [907204-31-3]+TX, fluopyram [658066-35-4]+TX, fenaminstrobin [366815-39-6]+TX, isofetamid [875915-78-9]+TX, hexaconazole [79983-71-4]+TX, imazalil [35554-44-0]+TX, imibenconazole [86598-92-7]+TX, ipconazole [125225-28-7]+TX, ipfentrifluconazole [1417782-08-1]+TX, isotianil [224049-04-1]+TX, mandestrobin [173662-97-0](can be prepared according to the procedures described in WO 2010/093059)+TX, mefentrifluconazole [1417782-03-6]+TX, metconazole [125116-23-6]+TX, myclobutanil [88671-89-0]+TX, paclobutrazol [76738-62-0]+TX, pefurazoate [101903-30-4]+TX, penflufen [494793-67-8]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidin [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, fluindapyr [1383809-87-7]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, flutianil [958647-10-4]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3][112-65-2](free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1,93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, pyraoxystrobin [862588-11-2]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxinecopper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, picarbutrazox [500207-04-5]+TX, polyoxins [11113-80-7]+TX, probenazole [27605-76-1]+TX, propamocarb [25606-41-1]+TX, proquinazid [189278-12-4]+TX, pydiflumetofen [1228284-64-7]+TX, pyrametostrobin [915410-70-7]+TX, pyroquilon [57369-32-1]+TX, pyriofenone [688046-61-9]+TX, pyribencarb [799247-52-2]+TX, pyrisoxazole [847749-37-5]+TX, quinoxyfen [124495-18-7]+TX, quintozene [82-68-8]+TX, sulfur [7704-34-9]+TX, Timorex Gold™ (plant extract containing tea tree oil from the Stockton Group)+TX, tebufloquin [376645-78-2]+TX, tiadinil [223580-51-6]+TX, triazoxide [72459-58-6]+TX, tolprocarb [911499-62-2]+TX, triclopyricarb [902760-40-1]+TX, tricyclazole [41814-78-2]+TX, triforine [26644-46-2]+TX, validamycin [37248-47-8]+TX, valifenalate [283159-90-0]+TX, zoxamide (RH7281) [156052-68-5]+TX, mandipropamid [374726-62-2]+TX, isopyrazam [881685-58-1]+TX, phenamacril+TX, sedaxane [874967-67-6]+TX, trinexapac-ethyl [95266-40-3]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a, 12b-decahydro-6,12-dihydroxy-4,6a, 12b-trimethyl-11-oxo-9-(3-pyridinyl)-2H, 11 Hnaphtho[2,1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide [926914-55-8]+TX, or a biologically active compound selected from the group consisting of N-[(5-chloro-2-isopropyl-phenyl)methyl]-N-cyclopropyl-3-(difluoromethyl)-5-fluoro-1-methyl-pyrazole-4-carboxamide (can be prepared according to the procedures described in WO 2010/130767)+TX, 2,6-Dimethyl-1H,5H-[1,4]dithiino[2,3-c:5,6-c']dipyrrole-1,3,5,7(2H,6H)-tetrone (can be prepared according to the procedures described in WO 2011/138281)+TX, 6-ethyl-5,7-dioxo-pyrrolo[4,5][1,4]dithiino[1,2-c]isothiazole-3-carbonitrile+TX, 4-(2-bromo-4-fluoro-phenyl)-N-(2-chloro-6-fluoro-phenyl)-2,5-dimethyl-pyrazol-3-amine (can be prepared according to the procedures described in WO 2012/031061)+TX, 3-(difluoromethyl)-N-(7-fluoro-1,1,3-trimethyl-indan-4-yl)-1-methyl-pyrazole-4-carboxamide (can be prepared according to the procedures described in WO 2012/084812)+TX, CAS 850881-30-0+TX, 3-(3,4-dichloro-1,2-thiazol-5-yl-methoxy)-1,2-benzothiazole 1,1-dioxide (can be prepared according to the procedures described in WO 2007/129454)+TX, 2-[2-[(2,5-dimethylphenoxy)methyl]phenyl]-2-methoxy-N-methyl-acetamide+TX, 3-(4,4-difluoro-3,4-dihydro-3,3-dimethylisoquinolin-1-yl)quinolone (can be prepared according to the procedures described in WO 2005/070917)+TX, 2-[2-fluoro-6-[(8-fluoro-2-methyl-3-quinolyl)oxy]phenyl]propan-2-ol (can be prepared according to the procedures described in WO 2011/081174)+TX, 2-[2-[(7,8-difluoro-2-methyl-3-quinolyl)oxy]-6-fluoro-phenyl]propan-2-ol (can be prepared according to the procedures described in WO 2011/081174)+TX, oxathiapiprolin+TX [1003318-67-9], tert-butyl N-[6-[[[(1-methyltetrazol-5-yl)-phenyl-methylene]amino]oxymethyl]-2-pyridyl] carbamate+TX, N-[2-(3,4-difluorophenyl)phenyl]-3-(trifluoromethyl)pyrazine-2-carboxamide (can be prepared according to the procedures described in WO 2007/072999)+TX, 3-(difluoromethyl)-1-methyl-N-[(3R)-1,1,3-trimethylindan-4-yl]pyrazole-4-carboxamide (can be prepared according to the procedures described in WO 2014/013842)+TX, 2,2,2-trifluoroethyl N-[2-methyl-1-[[(4-methylbenzoyl)amino]methyl]propyl]carbamate+TX, (2RS)-2-[4-(4-chlorophenoxy)-α,α,α-trifluoro-o-tolyl]-1-(1H-1,2,4-triazol-1-yl)propan-2-ol+TX, (2RS)-2-[4-(4-chlorophenoxy)-α,α,α-trifluoro-o-tolyl]-3-methyl-1-(1H-1,2,4-triazol-1-yl)butan-2-ol+TX, 2-(difluoromethyl)-N-[(3R)-3-ethyl-1,1-dimethyl-indan-4-yl]pyridine-3-carboxamide+TX, 2-(difluoromethyl)-N-[3-ethyl-1,1-dimethyl-indan-4-yl]pyridine-3-carboxamide+TX, N'-(2,5-dimethyl-4-phenoxy-phenyl)-N-ethyl-N-methyl-formamidine+TX, N'-[4-(4,5-dichlorothiazol-2-yl)oxy-2,5-dimethyl-phenyl]-N-ethyl-N-methyl-formamidine (can be prepared according to the procedures described in WO 2007/031513)+TX, [2-[3-[2-[1-[2-[3,5-bis(difluoromethyl)pyrazol-1-yl]acetyl]-4-piperidyl]thiazol-4-yl]-4,5-dihydroisoxazol-5-yl]-3-chloro-phenyl]methanesulfonate (can be prepared according to the procedures described in WO 2012/025557)+TX, but-3-ynyl N-[6-[[[(Z)-[(1-methyltetrazol-5-yl)-phenyl-methylene]amino]oxymethyl]-2-pyridyl] carbamate (can be prepared according to the procedures described in WO 2010/000841)+TX, 2-[[3-(2-chlorophenyl)-2-(2,4-difluorophenyl)oxiran-2-yl]methyl]-4H-1,2,4-triazole-3-thione (can be prepared according to the procedures described in WO 2010/146031)+TX, methyl N-[[5-[4-(2,4-dimethylphenyl)triazol-2-yl]-2-methyl-phenyl]methyl]carbamate+TX, 3-chloro-6-methyl-5-phenyl-4-(2,4,6-trifluorophenyl)pyridazine (can be prepared according to the procedures described in WO 2005/121104)+TX, 2-[2-chloro-4-(4-chlorophenoxy)phenyl]-1-(1,2,4-triazol-1-yl)propan-2-ol (can be prepared according to the procedures described in WO 2013/024082)+TX, 3-chloro-4-(2,6-difluorophenyl)-6-methyl-5-phenyl-pyridazine (can be prepared according to the procedures described in WO 2012/020774)+TX, 4-(2,6-difluorophenyl)-6-methyl-5-phenyl-pyridazine-3-carbonitrile (can be prepared according to the procedures described in WO 2012/020774)+TX, (R)-3-(difluoromethyl)-1-methyl-N-[1,1,3-trimethylindan-4-yl]pyrazole-4-carboxamide (can be prepared according to the procedures described in WO 2011/162397)+TX, 3-(difluoromethyl)-N-(7-fluoro-1,1,3-trimethyl-indan-4-yl)-1-methyl-pyrazole-4-carboxamide (can be prepared according to the procedures described in WO 2012/084812)+TX, 1-[2-[[1-(4-chlorophenyl)pyrazol-3-yl]oxymethyl]-3-methyl-phenyl]-4-methyl-tetrazol-5-one (can be prepared according to the procedures described in WO 2013/

162072)+TX, 1-methyl-4-[3-methyl-2-[[2-methyl-4-(3,4,5-trimethylpyrazol-1-yl)phenoxy]methyl]phenyl]tetrazol-5-one (can be prepared according to the procedures described in WO 2014/051165)+TX, (Z,2E)-5-[1-(4-chlorophenyl)pyrazol-3-yl]oxy-2-methoxyimino-N,3-dimethyl-pent-3-enamide+TX, (4-phenoxyphenyl)methyl 2-amino-6-methyl-pyridine-3-carboxylate+TX, N-(5-chloro-2-isopropylbenzyl)-N-cyclopropyl-3-(difluoromethyl)-5-fluoro-1-methylpyrazole-4-carboxamide [1255734-28-1] (can be prepared according to the procedures described in WO 2010/130767)+TX, 3-(difluoromethyl)-N—[(R)-2,3-dihydro-1,1,3-trimethyl-1H-inden-4-yl]-1-methylpyrazole-4-carboxamide [1352994-67-2]+TX, N'-(2,5-dimethyl-4-phenoxy-phenyl)-N-ethyl-N-methyl-formamidine+TX, N'-[4-(4,5-dichloro-thiazol-2-yloxy)-2,5-dimethyl-phenyl]-N-ethyl-N-methyl-formamidine+TX, N'-(2,5-dimethyl-4-phenoxy-phenyl)-N-ethyl-N-methyl-formamidine+TX, N'-[4-(4,5-dichloro-thiazol-2-yloxy)-2,5-dimethyl-phenyl]-N-ethyl-N-methyl-formamidine+TX,

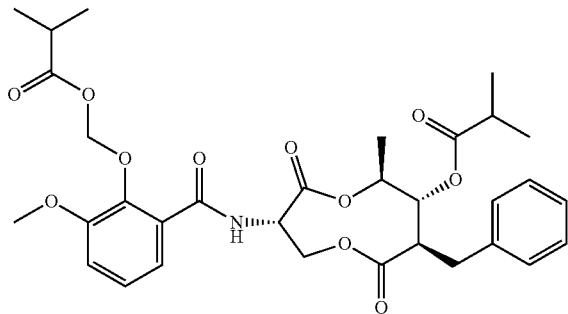 [SMILES: COc1cccc(C(=O)N[C@H]2COC(=O)[C@H](Cc3ccccc3)[C@@H](OC(=O)C(C)C)[C@H](C)OC2=O)c1OCOC(=O)C(C)C]

(fenpicoxamid [517875-34-2](as described in WO 2003/035617))+TX, (1 S)-2,2-bis(4-fluorophenyl)-1-methylethyl N-{[3-(acetyloxy)-4-methoxy-2-pyridyl]carbonyl}-L-alaninate [1961312-55-9](as described in WO 2016/122802)+TX, 2-(difluoromethyl)-N-(1,1,3-trimethylindan-4-yl)pyridine-3-carboxamide+TX, 2-(difluoromethyl)-N-(3-ethyl-1,1-dimethyl-indan-4-yl)pyridine-3-carboxamide+TX, 2-(difluoromethyl)-N-(1,1-dimethyl-3-propyl-indan-4-yl)pyridine-3-carboxamide+TX, 2-(difluoromethyl)-N-(3-isobutyl-1,1-dimethyl-indan-4-yl)pyridine-3-carboxamide+TX, 2-(difluoromethyl)-N-[(3R)-1,1,3-trimethylindan-4-yl]pyridine-3-carboxamide+TX, 2-(difluoromethyl)-N-[(3R)-3-ethyl-1,1-dimethyl-indan-4-yl]pyridine-3-carboxamide+TX, and 2-(difluoromethyl)-N-[(3R)-1,1-dimethyl-3-propyl-indan-4-yl]pyridine-3-carboxamide+TX, wherein each of these carboxamide compounds can be prepared according to the procedures described in WO 2014/095675 and/or WO 2016/139189.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

The active ingredient mixture of the compounds of formula (I) selected from one compound as represented in Tables A1 to A8 (above) or Table E (below) is preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound as represented in Tables A1 to A8 (above) or Table E (below), and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying a compound as represented in Tables A1 to A8 (above) or Table E (below) and the active ingredient(s) as described above, is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds (I) for the preparation of these compositions are also a subject of the invention.

Another aspect of the invention is related to the use of a compound of Formula (I) or of a preferred individual compound as defined herein, of a composition comprising at least one compound of Formula (I) or at least one preferred individual compound as above-defined, or of a fungicidal or insecticidal mixture comprising at least one compound of Formula (I) or at least one preferred individual compound as above-defined, in admixture with other fungicides or insecticides as described above, for controlling or preventing infestation of plants, e.g. useful plants such as crop plants, propagation material thereof, e.g. seeds, harvested crops, e.g. harvested food crops, or non-living materials by insects or by phytopathogenic microorganisms, preferably fungal organisms.

A further aspect of invention is related to a method of controlling or preventing an infestation of plants, e.g. useful plants such as crop plants, propagation material thereof, e.g. seeds, harvested crops, e.g. harvested food crops, or of non-living materials by phytopathogenic or spoilage microorganisms or organisms potentially harmful to man, especially fungal organisms, which comprises the application of a compound of formula (I) or of a preferred individual compound as above-defined as active ingredient to the plants, to parts of the plants or to the locus thereof, to the propagation material thereof, or to any part of the non-living materials.

Controlling or preventing means reducing infestation by insects or by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, or insects which comprises the application of a compound of formula (I), or an agrochemical composition which contains at least one of said compounds, is foliar application. The frequency of application and the rate of application will depend on the risk of infestation by the corresponding pathogen or insect. However, the compounds of formula (I) can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula (I) may also be applied to seeds (coating) by impregnating the seeds or tubers either with a liquid formulation of the fungicide or coating them with a solid formulation.

A formulation, e.g. a composition containing the compound of formula (I), and, if desired, a solid or liquid adjuvant or monomers for encapsulating the compound of formula (I), may be prepared in a known manner, typically by intimately mixing and/or grinding the compound with extenders, for example solvents, solid carriers and, optionally, surface active compounds (surfactants).

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is preferably 1 g to 2000 g of active ingredient per hectare, more preferably 10 to 1000 g/ha, most preferably 10 to 600 g/ha. When used as seed drenching agent, convenient dosages are from 10 mg to 1 g of active substance per kg of seeds.

When the combinations of the present invention are used for treating seed, rates of 0.001 to 50 g of a compound of formula (I) per kg of seed, preferably from 0.01 to 10 g per kg of seed are generally sufficient.

Suitably, a composition comprising a compound of formula (I) according to the present invention is applied either preventative, meaning prior to disease development or curative, meaning after disease development.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the ondensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) together with component (B) and (C), and optionally other active agents, particularly microbiocides or conservants or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

Whereas it is preferred to formulate commercial products as concentrates, the end user will normally use dilute formulations.

EXAMPLES

The Examples which follow serve to illustrate the invention. Certain compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm or 0.2 ppm.

Throughout this description, temperatures are given in degrees Celsius and "m.p." means melting point. LC/MS means Liquid Chromatography Mass Spectroscopy and the description of the apparatus and the methods are:

Method G:

Spectra were recorded on a Mass Spectrometer from Waters (SQD, SQDII Single quadrupole mass spectrometer) equipped with an electrospray source (Polarity: positive and negative ions), Capillary: 3.00 kV, Cone range: 30 V, Extractor: 2.00 V, Source Temperature: 150° C., Desolvation Temperature: 350° C., Cone Gas Flow: 50 l/h, Desolvation Gas Flow: 650 l/h, Mass range: 100 to 900 Da) and an Acquity UPLC from Waters: Binary pump, heated column compartment, diode-array detector and ELSD detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 1.2 min; Flow (ml/min) 0.85

Method H:

Spectra were recorded on a Mass Spectrometer from Waters (SQD, SQDII Single quadrupole mass spectrometer) equipped with an electrospray source (Polarity: positive and negative ions), Capillary: 3.00 kV, Cone range: 30V, Extractor: 2.00 V, Source Temperature: 150° C., Desolvation Temperature: 350° C., Cone Gas Flow: 50 l/h, Desolvation Gas Flow: 650 l/h, Mass range: 100 to 900 Da) and an Acquity UPLC from Waters: Binary pump, heated column compartment, diode-array detector and ELSD detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 2.7 min; Flow (ml/min) 0.85

Method I:

Spectra were recorded on a Mass Spectrometer (ACQUITY UPLC) from Waters (SQD, SQDII or ZQ Single quadrupole mass spectrometer) equipped with an electrospray source (Polarity: positive or negative ions, Capillary (kV) 3.5, Cone (V) 30.00, Extractor (V) 3.00, Source Temperature (° C.) 150, Desolvation Temperature (° C.) 400, Cone Gas Flow (L/Hr) 60, Desolvation Gas Flow (L/Hr) 700, Mass range: 140 to 800 Da) and an Acquity UPLC from Waters: Binary pump, heated column compartment and diode-array detector. Solvent degasser, binary pump, heated column compartment and diode-array detector. Column: Waters ACQUITY UPLC HSS T3; Column length: 30 mm; Internal diameter of column: 2.1 mm; Particle Size: 1.8 micron; Temperature: 60° C., DAD Wavelength range (nm): 210 to 400. Solvent Gradient A: Water/Methanol 9:1,0.1% formic acid and Solvent B: Acetonitrile, 0.1% formic acid

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Formulation Examples

Wettable Powders

| | a) | b) | c) |
|---|---|---|---|
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

Powders for Dry Seed Treatment

| | a) | b) | c) |
|---|---|---|---|
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The active ingredient is thoroughly mixed with the adjuvants and the mixture is thoroughly ground in a suitable mill, affording powders that can be used directly for seed treatment.

Emulsifiable Concentrate

| | |
|---|---|
| active ingredient [compound of formula (I)] | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

Dusts

| | a) | b) | c) |
|---|---|---|---|
| Active ingredient [compound of formula (I)] | 5% | 6% | 4% |
| talcum | 95% | — | — |

-continued

|  | a) | b) | c) |
|---|---|---|---|
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

Extruder Granules

| Active ingredient [compound of formula (I)] | 15% |
|---|---|
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

Coated Granules

| Active ingredient [compound of formula (I)] | 8% |
|---|---|
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

Suspension Concentrate

| active ingredient [compound of formula (I)] | 40% |
|---|---|
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| active ingredient [compound of formula (I)] | 40% |
|---|---|
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula (I) are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

Preparation Examples

Example 1: 4,4,4-trifluoro-N-(8-fluoro-3-quinolyl)-2-methyl-2-[(1-methylcyclopropyl)methyl]butanamide Step 1: Ethyl 2,4-dimethyl-2-(2,2,2-trifluoroethyl)pent-4-enoate To a cooled (−70° C.) solution of lithium diisopropylamide (2 M, 30.6 mmol) in tetrahydrofuran (50 mL) was added a solution of ethyl 4-methyl-2-(2,2,2-trifluoroethyl)pent-4-enoate (20.4 mmol, 6.09 g) in tetrahydrofuran (60 mL) dropwise, and the mixture was stirred at −70° C. for 30 min. Then, iodomethane (26.5 mmol, 3.80 g) was added dropwise at −70° C., and the mixture was stirred at −70° C. for an additional 1 h. The reaction mixture was carefully poured into 100 ml of saturated aqueous solution of ammonium chloride. The aqueous phase was extracted with ethyl acetate and the combined organic extracts were dried over sodium sulfate, filtered and concentrated under reduced pressure. The residue was purified by flash chromatography (cyclohexane/ethyl acetate gradient) to give ethyl 2,4-dimethyl-2-(2,2,2-trifluoroethyl)pent-4-enoate as a yellow oil:

$^1$H NMR (400 MHz, CHLOROFORM-d) δ ppm 1.30 (t, J=6.97 Hz, 3H) 1.33 (d, J=1.10 Hz, 3H) 1.71 (s, 3H) 2.16-2.33 (m, 2H) 2.46-2.53 (m, 1H) 2.69-2.85 (m, 1H) 4.08-4.26 (m, 2H) 4.69-4.76 (m, 1H) 4.89-4.96 (m, 1H)

Step 2: Ethyl 4,4,4-trifluoro-2-methyl-2-[(1-methylcyclopropyl)methyl]butanoate

To a cooled (0° C.) solution of diethylzinc (79.5 mmol, 79.5 mL) in dichloromethane (63.6 mL) was added 2,2,2-trifluoroacetic acid (47.7 mmol, 3.71 mL) dropwise, and the mixture was stirred at 0° C. for 30 min (white suspension). Then, diiodomethane (47.7 mmol, 3.88 mL) was added dropwise at 0° C., and the mixture was stirred at 0° C. for 30 min. To finish, ethyl 2,4-dimethyl-2-(2,2,2-trifluoroethyl)pent-4-enoate (2.06 mmol, 0.49 g) in dichloromethane (1 mL) was added dropwise at 0° C. and the reaction mixture was stirred at room temperature for additional 5 h. The reaction mixture was carefully poured into 50 ml of saturated aqueous solution of ammonium chloride. The aqueous phase was extracted with ethyl acetate and the combined organic extracts were dried over sodium sulfate, filtered and concentrated under reduced pressure to give ethyl 4,4,4-trifluoro-2-methyl-2-[(1-methylcyclopropyl)methyl]butanoate as a yellow oil: ¹H NMR (400 MHz, CHLOROFORM-d) δ ppm 0.17-0.40 (m, 4H) 1.00 (s, 3H) 1.31 (m, 4H) 1.41 (d, J=1.10 Hz, 3H) 1.93-2.02 (m, 1H) 2.14-2.30 (m, 1H) 2.67-2.84 (m, 1H) 4.10-4.24 (m, 2H)

Step 3: 4,4,4-trifluoro-2-methyl-2-[(1-methylcyclopropyl) methyl]butanoic acid

A suspension of ethyl 4,4,4-trifluoro-2-methyl-2-[(1-methylcyclopropyl)methyl]butanoate (1.70 mmol, 430 mg), Sodium hydroxide (6.8 mmol, 0.27 g), ethanol (6.9 mL) and 1,4-dioxane (6.9 mL) was stirred at 80° C. for 4 h. The reaction mixture was poured into 20 ml of water. The aqueous phase was washed with dichloromethane, acidified with aqueous hydrochloric acid 2 M (pH 1-2) before being extracted with dichloromethane. The combined organics extracts were dried over sodium sulfate, filtered and concentrated under reduced pressure to 4,4,4-trifluoro-2-methyl-2-[(1-methylcyclopropyl)methyl]butanoic acid as a dark orange oil:

¹H NMR (400 MHz, CHLOROFORM-d) δ ppm 0.14-0.46 (m, 4H) 1.07 (s, 3H) 1.37-1.48 (m, 4H) 1.88-2.02 (m, 1H) 2.19-2.38 (m, 1H) 2.68-2.90 (m, 1H)

Step 4: 4,4,4-trifluoro-N-(8-fluoro-3-quinolyl)-2-methyl-2-[(1-methylcyclopropyl)methyl]butanamide To a solution of 4,4,4-trifluoro-2-methyl-2-[(1-methylcyclopropyl)methyl]butanoic acid (1.31 mmol, 293 mg), N,N-dimethylformamide (1 drop) in dichloromethane (5.24 mL) at room temperature was added oxalyl chloride (2.62 mmol, 0.2311 mL) dropwise (gas evolution) and the mixture was stirred for 30 min. The reaction mixture was concentrated under reduced pressure and diluted with dichloromethane (5.24 mL). This mixture was added dropwise at room temperature to a solution of 8-fluoroquinolin-3-amine (1.31 mmol, 0.21263 g), N,N-dimethylpyridin-4-amine (0.07 mmol, 0.008 g) and pyridine (2.62 mL). The mixture was stirred at room temperature for 3 h (red/dark orange suspension). The reaction mixture was poured into 20 ml of saturated aqueous solution of sodium hydrogen carbonate. The aqueous phase was extracted with dichloromethane and the combined organic extracts were dried over sodium sulfate, filtered and concentrated under reduced pressure. The residue was purified by flash chromatography (cyclohexane/ethyl acetate gradient) to give 4,4,4-trifluoro-N-(8-fluoro-3-quinolyl)-2-methyl-2-[(1-methylcyclopropyl) methyl]butanamide as a pale yellow solid: mp=60-70° C., LC-MS (Method G) UV Detection: 220 nm, Rt=1.04 min; MS: (M+1)=369;

¹H NMR (400 MHz, CHLOROFORM-d) δ ppm 0.16-0.55 (m, 4H) 1.07 (s, 3H) 1.17-1.28 (m, 1H) 1.70-1.74 (m, 3H) 2.14-2.30 (m, 1H) 2.30-2.42 (m, 1H) 2.87-3.10 (m, 1H) 7.3-7.35 (m, 1H) 7.45-7.55 (m, 1H) 7.65 (d, 1H) 7.72-7.96 (m, 1H) 8.81 (s, 2H)

TABLE E

Physical data of compounds of formula (I)

| Entry | STRUCTURE | RT (min) | [M + H] (measured) | Method | MP °C. |
|---|---|---|---|---|---|
| E1 | 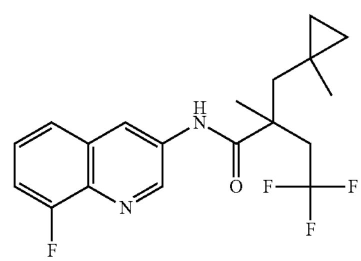 [SMILES: CC1(CC(C)(CC(F)(F)F)C(=O)Nc2cnc3c(F)cccc3c2)CC1] | 1.04 | 369 | G | 60-70 |
| E2 | 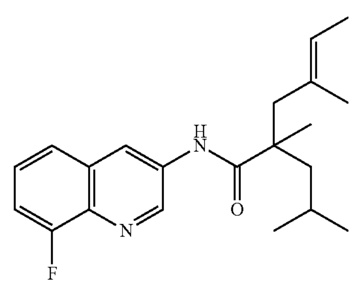 [SMILES: C/C=C(\C)CC(C)(CC(C)C)C(=O)Nc1cnc2c(F)cccc2c1] | 1.19 | 344 | G | 135-137 |
| E3 | 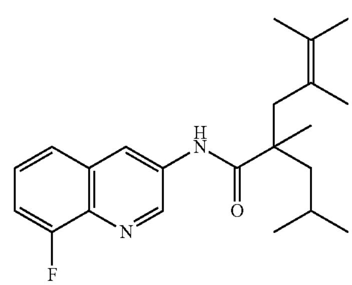 [SMILES: CC(C)=C(C)CC(C)(CC(C)C)C(=O)Nc1cnc2c(F)cccc2c1] | 1.24 | 358 | G | |

TABLE E-continued

Physical data of compounds of formula (I)

| Entry | STRUCTURE | RT (min) | [M + H] (measured) | Method | MP °C. |
|---|---|---|---|---|---|
| E4 | 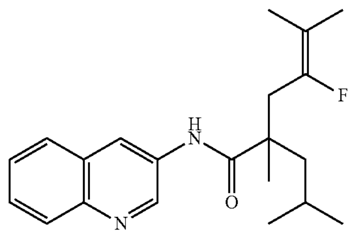 [SMILES: CC(C)=C(F)CC(C)(CC(C)C)C(=O)Nc1cnc2ccccc2c1] | 1.15 | 343 | G | |
| E5 | 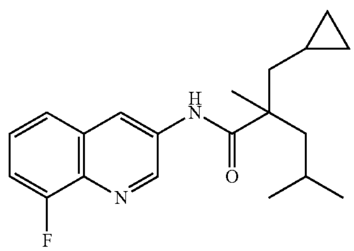 [SMILES: CC(C)CC(C)(CC1CC1)C(=O)Nc1cnc2c(F)cccc2c1] | 1.14 | 329 | G | |
| E6 | 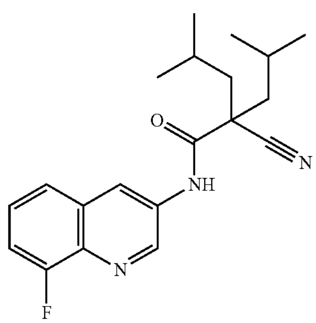 [SMILES: CC(C)CC(C#N)(CC(C)C)C(=O)Nc1cnc2c(F)cccc2c1] | 1.09 | 342 | G | |
| E7 | 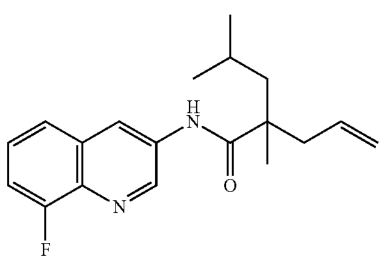 [SMILES: C=CCC(C)(CC(C)C)C(=O)Nc1cnc2c(F)cccc2c1] | 1.12 | 315 | G | |
| E8 | 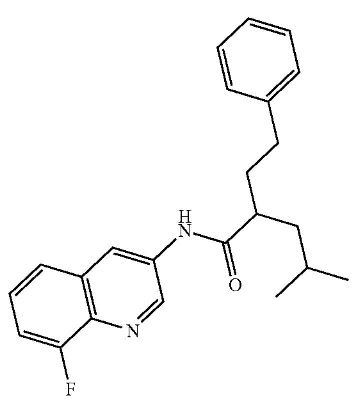 [SMILES: CC(C)CC(CCc1ccccc1)C(=O)Nc1cnc2c(F)cccc2c1] | 1.94 | 363 | H | |

TABLE E-continued

Physical data of compounds of formula (I)

| Entry | STRUCTURE | RT (min) | [M + H] (measured) | Method | MP °C. |
|---|---|---|---|---|---|
| E9 | 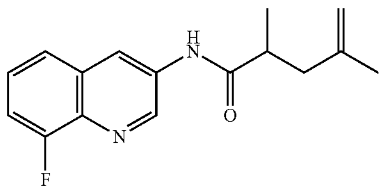 [SMILES: C=C(C)CC(C)C(=O)Nc1cnc2c(F)cccc2c1] | 0.95 | 273 | G | |
| E10 | 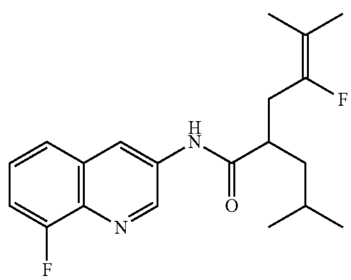 [SMILES: CC(C)=C(F)CC(CC(C)C)C(=O)Nc1cnc2c(F)cccc2c1] | 1.15 | 347 | G | 103-105 |
| E11 | 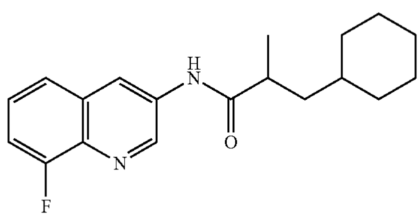 [SMILES: CC(CC1CCCCC1)C(=O)Nc1cnc2c(F)cccc2c1] | 1.13 | 315 | G | 179-181 |
| E12 | 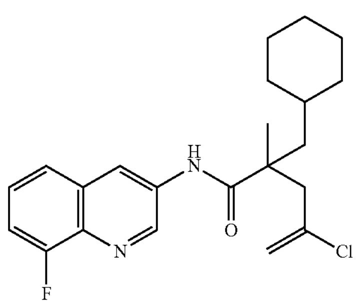 [SMILES: C=C(Cl)CC(C)(CC1CCCCC1)C(=O)Nc1cnc2c(F)cccc2c1] | 1.24 | 389 | G | |
| E13 | 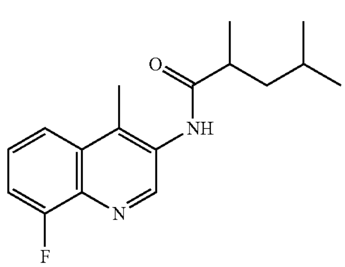 [SMILES: Cc1c(NC(=O)C(C)CC(C)C)cnc2c(F)cccc12] | 0.93 | 289 | G | |

TABLE E-continued

Physical data of compounds of formula (I)

| Entry | STRUCTURE | RT (min) | [M + H] (measured) | Method | MP °C. |
|---|---|---|---|---|---|
| E14 | ![structure with quinoline, 8-F, NH-C(=O)-CH(CH3)-CH2-CF3] | | | | |

Biological Examples

*Botryotinia fuckeliana* (*Botrytis cinerea*)/liquid culture (Gray mould)

Conidia of the fungus from cryogenic storage are directly mixed into nutrient broth (Vogels broth). After placing a (DMSO) solution of test compound into a microtiter plate (96-well format), the nutrient broth containing the fungal spores is added. The test plates are incubated at 24° C. and the inhibition of growth is determined photometrically 3-4 days after application.

The following compounds gave at least 80% control of *Botryotinia fuckeliana* at 20 ppm when compared to untreated control under the same conditions, which showed extensive disease development:

E1, E2, E3, E4, E5, E6, E7, E8, E9, E10, E11, E12, E13, E14

*Glomerella lagenarium* (*Colletotrichum lagenarium*)/liquid culture (Anthracnose)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is measured photometrically 3-4 days after application.

The following compounds gave at least 80% control of *Glomerella* lagenarium at 20 ppm when compared to untreated control under the same conditions, which showed extensive disease development:

E1, E2, E3, E4, E5, E6, E7, E8, E9, E10, E11, E12, E13, E14

*Fusarium culmorum*/liquid culture (Head blight)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 3-4 days after application.

The following compounds gave at least 80% control of *Fusarium culmorum* at 20 ppm when compared to untreated control under the same conditions, which showed extensive disease development:

E1, E2, E3, E4, E5, E6, E7, E8, E9, E10, E11, E12, E13, E14

*Fusarium culmorum*/wheat/spikelet preventative (Head blight)

Wheat spikelets cv. Monsun are placed on agar in multiwell plates (24-well format) and sprayed with the formulated test compound diluted in water. The spikelets are inoculated with a spore suspension of the fungus 1 day after application. The inoculated spikelets are incubated at 20° C. and 60% rh under a light regime of 72 h semi darkness followed by 12 h light/12 h darkness in a climate chamber and the activity of a compound is assessed as percent disease control compared to untreated when an appropriate level of disease damage appears on untreated check spikelets (6-8 days after application).

The following compounds gave at least 80% control of *Fusarium culmorum* at 200 ppm when compared to untreated control under the same conditions, which showed extensive disease development:

E7

*Gaeumannomyces graminis*/liquid culture (Take-all of cereals)

Mycelial fragments of the fungus from cryogenic storage were directly mixed into nutrient broth (PDB potato dextrose broth). After placing a (DMSO) solution of test compound into a microtiter plate (96-well format), the nutrient broth containing the fungal spores iss added. The test plates are incubated at 24° C. and the inhibition of growth is determined photometrically 4-5 days after application.

The following compounds gave at least 80% control of *Gaeumannomyces graminis* at 20 ppm when compared to untreated control under the same conditions, which showed extensive disease development:

E7, E9

*Monographella nivalis* (*Microdochium nivale*)/liquid culture (foot rot cereals)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

The following compounds gave at least 80% control of *Monographella nivalis* at 20 ppm when compared to untreated control under the same conditions, which showed extensive disease development:
E1, E5, E8, E9, E11, E12

*Magnaporthe grisea* (*Pyricularia oryzae*)/liquid culture (Rice Blast)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 3-4 days after application.

The following compounds gave at least 80% control of *Magnaporthe grisea* at 20 ppm when compared to untreated control under the same conditions, which showed extensive disease development:

E1, E2, E3, E4, E5, E6, E7, E8, E10, E11, E12

*Magnaporthe grisea* (*Pyricularia oryzae*)/rice/leaf disc preventative (Rice Blast)

Rice leaf segments cv. Ballila are placed on agar in a multiwell plate (24-well format) and sprayed with the formulated test compound diluted in water. The leaf segments are inoculated with a spore suspension of the fungus 2 days after application. The inoculated leaf segments are incubated at 22° C. and 80% rh under a light regime of 24 h darkness followed by 12 h light/12 h darkness in a climate cabinet and the activity of a compound is assessed as percent disease control compared to untreated when an appropriate level of disease damage appears in untreated check leaf segments (5-7 days after application).

The following compounds gave at least 80% control of *Magnaporthe grisea* at 200 ppm when compared to untreated control under the same conditions, which showed extensive disease development:

E1, E12

*Sclerotinia sclerotiorum*/liquid culture (cottony rot)

Mycelia fragments of a newly grown liquid culture of the fungus are directly mixed into nutrient broth (Vogels broth). After placing a (DMSO) solution of test compound into a microtiter plate (96-well format) the nutrient broth containing the fungal material is added. The test plates are incubated at 24° C. and the inhibition of growth is determined photometrically 3-4 days after application.

The following compounds gave at least 80% control of *Sclerotinia sclerotiorum* at 20 ppm when compared to untreated control under the same conditions, which showed extensive disease development:

E5, E7, E13

What is claimed is:

1. A compound of formula (I)

(I)

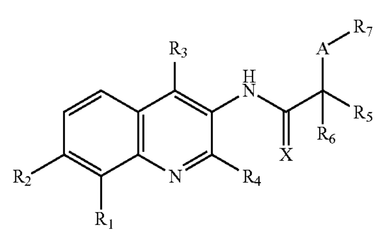

wherein

X is O or S;

$R_1$ is hydrogen, halogen, methyl or cyano;

$R_2$ is hydrogen, methyl or halogen;

$R_3$ and $R_4$ are each independently selected from hydrogen, halogen and methyl;

$R_5$ is $C_1$-$C_5$ alkyl, $C_2$-$C_5$ alkenyl, $C_1$-$C_4$ alkoxy, $C_3$-$C_5$ cycloalkyl($C_1$-$C_2$)alkyl or $C_3$-$C_6$ cycloalkyl, wherein the alkyl, alkenyl and cycloalkyl groups may be optionally substituted with 1 to 3 substituents independently selected from halogen, cyano, $C_1$-$C_3$ alkyl, $C_1$-$C_3$ haloalkyl, $C_1$-$C_3$ alkoxy and $C_1$-$C_3$ alkylthio;

$R_6$ is hydrogen, fluoro, cyano or $C_1$-$C_4$ alkyl, wherein the alkyl may be optionally substituted with 1 to 3 substituents independently selected from halogen and $C_1$-$C_3$ alkoxy;

A is a direct bond or $CR_8R_9$;

$R_7$ is $CF_3$, $C_2$-$C_5$ alkyl, $C_3$-$C_7$ cycloalkyl, $C_2$-$C_5$ alkenyl, $C_4$-$C_7$ cycloalkenyl, wherein the alkyl, cycloalkyl, alkenyl and cycloalkenyl may be optionally substituted with one or more substituents independently selected from halogen, cyano, $C_1$-$C_3$ alkyl, $C_1$-$C_3$ haloalkyl, $C_1$-$C_3$ alkoxy, $C_1$-$C_3$ alkylthio, $C_1$-$C_3$ haloalkoxy, $C_1$-$C_3$ haloalkylthio, $C_3$-$C_7$ cycloalkyl and phenyl which may be optionally substituted with 1 to 3 substituents independently selected from halogen, cyano, $C_1$-$C_3$ alkyl, $C_1$-$C_3$ haloalkyl, $C_1$-$C_3$ alkoxy, $C_1$-$C_3$ alkylthio, $C_1$-$C_3$ haloalkoxy, $C_1$-$C_3$ haloalkylthio and $C_3$-$C_5$ cycloalkyl; and $R_8$ and $R_9$ are each independently selected from hydrogen, fluoro and methyl;

or a salt, enantiomer or N-oxide thereof, provided the compound is not 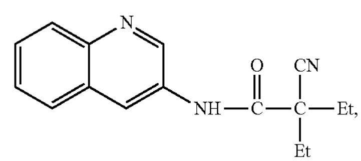 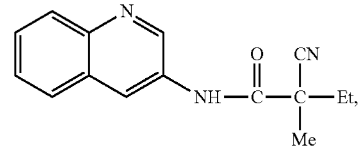 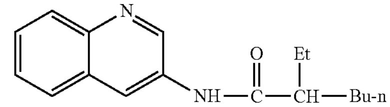 or

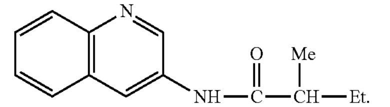

2. The compound, or a salt, enantiomer or N-oxide thereof, according to claim 1 wherein $R_1$ is hydrogen, fluoro, chloro, methyl or cyano.

3. The compound, or a salt, enantiomer or N-oxide thereof, according to claim 1 wherein $R_2$ is hydrogen, methyl, chloro or fluoro.

4. The compound, or a salt, enantiomer or N-oxide thereof, according to claim 1 wherein $R_3$ and $R_4$ are each independently selected from hydrogen and methyl.

5. The compound, or a salt, enantiomer or N-oxide thereof, according to claim 1 wherein $R_5$ is $C_1$-$C_5$ alkyl, $C_2$-$C_4$ alkenyl, $C_3$-$C_5$ cycloalkyl-$CH_2$— or $C_3$-$C_5$ cycloalkyl, wherein the alkyl, alkenyl and cycloalkyl groups may be optionally substituted with 1 to 3 substituents independently selected from fluoro, chloro and $C_1$-$C_3$ alkyl.

6. The compound, or a salt, enantiomer or N-oxide thereof, according to claim 1 wherein $R_6$, is hydrogen, fluoro, or $C_1$-$C_3$ alkyl, wherein the alkyl may be optionally substituted with a methoxy group.

7. The compound, or a salt, enantiomer or N-oxide thereof, according to claim 1 wherein $R_7$ is $CF_3$, $C_2$-$C_5$ alkyl, $C_3$-$C_7$ cycloalkyl, $C_2$-$C_5$ alkenyl, $C_4$-$C_7$ cycloalkenyl, wherein the alkyl, cycloalkyl, alkenyl and cycloalkenyl may be optionally substituted with one or more substituents independently selected from fluoro, chloro, cyano, $C_1$-$C_3$ alkyl, $C_1$-$C_3$ haloalkyl, $C_3$-$C_4$ cycloalkyl and phenyl which may be optionally substituted with 1 to 3 substituents independently selected from fluoro, chloro, methyl and trifluoromethyl.

8. The compound, or a salt, enantiomer or N-oxide thereof, according to claim 1 wherein A is a direct bond or $CH_2$.

9. The compound according to claim 1 wherein X is O or S; $R_1$ is hydrogen, fluoro, chloro or methyl; $R_2$ is hydrogen, chloro or fluoro; $R_3$ is methyl and $R_4$ is hydrogen; or $R_3$ is hydrogen and $R_4$ is methyl; or $R_3$ is hydrogen and $R_4$ is hydrogen; $R_5$ is $C_1$-$C_5$ alkyl, $C_2$-$C_4$ alkenyl, $C_3$-$C_4$ cycloalkyl-$CH_2$— or $C_3$-$C_5$ cycloalkyl, wherein the alkyl, alkenyl and cycloalkyl groups may be optionally substituted with 1 to 3 substituents independently selected from fluoro, chloro and methyl; $R_6$ is hydrogen or methyl, wherein the methyl may be optionally substituted with a methoxy group; A is a direct bond or $CH_2$; $R_7$ is $CF_3$, $C_2$-$C_4$ alkyl, $C_3$-$C_6$ cycloalkyl, $C_2$-$C_4$ alkenyl, $C_4$-$C_6$ cycloalkenyl, wherein the alkyl, cycloalkyl, alkenyl and cycloalkenyl may be optionally substituted with 1 to 3 substituents independently selected from fluoro, chloro, methyl, trifluoromethyl and cyclopropyl and/or one phenyl; or a salt, enantiomer or N-oxide thereof.

10. The compound, or a salt, enantiomer or N-oxide thereof, according to claim 1 wherein A is $CH_2$.

11. The compound according to claim 1 wherein X is O or S; $R_1$ is fluoro, chloro or methyl; $R_2$ is hydrogen or fluoro; $R_3$ and $R_4$ are both hydrogen; $R_5$ is trifluoroethyl, ethyl, isopropyl, iso-butyl, tert-butyl, neo-pentyl, $C_2$-$C_4$ alkenyl or cyclopropyl-$CH_2$—, wherein the ethyl, isopropyl, iso-butyl, alkenyl and cyclopropyl groups may be optionally substituted with 1 to 3 substituents independently selected from fluoro and chloro and/or one methyl group; $R_6$, is methyl; A is $CH_2$; $R_7$ is $CF_3$, ethyl, isopropyl, tert-butyl, $C_2$-alkenyl, cyclopropyl, cyclobutyl, cyclopentyl, cyclohexyl, cyclopentenyl or cyclohexenyl, wherein the ethyl, isopropyl, alkenyl cyclopropyl, cyclobutyl, cyclopentyl, cyclohexyl, cyclopentenyl and cyclohexenyl may be optionally substituted with 1 to 3 substituents independently selected from fluoro and chloro and/or one or two methyl groups; or a salt, enantiomer or N-oxide thereof.

12. The compound, or a salt, enantiomer or N-oxide thereof, according to claim 1 wherein X is O.

13. A compound, wherein the compound is selected from the group consisting of:

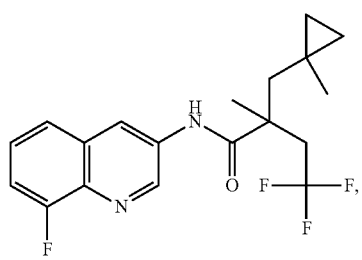

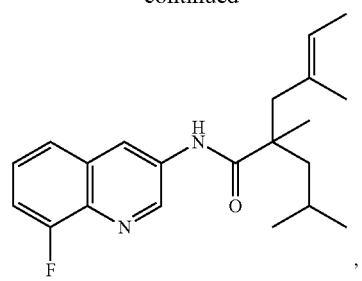

,

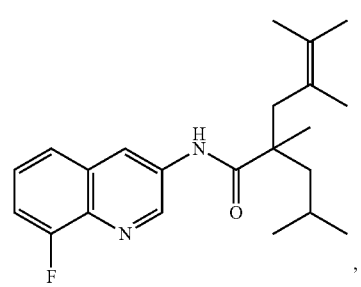

,

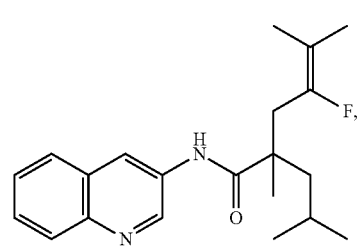

,

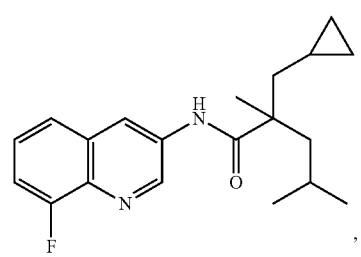

,

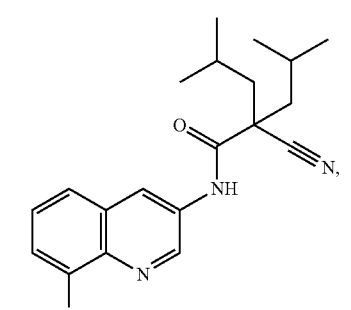

,

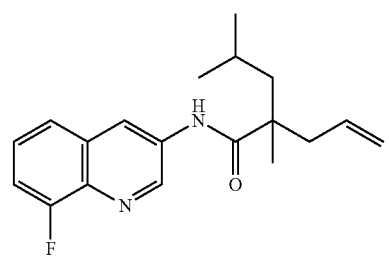

,

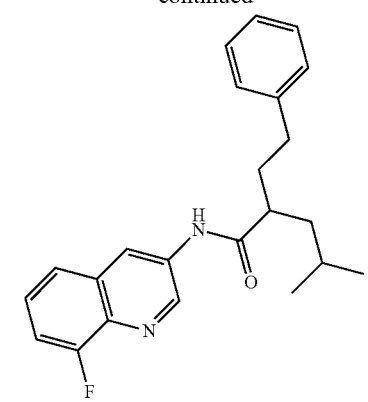

,

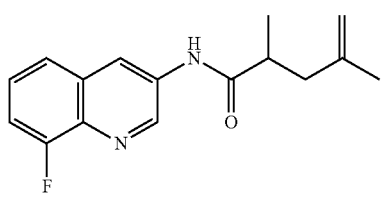

,

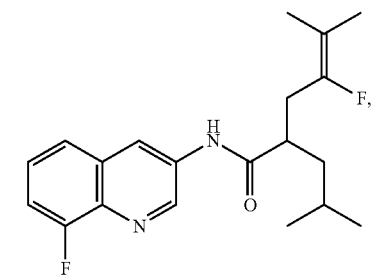

,

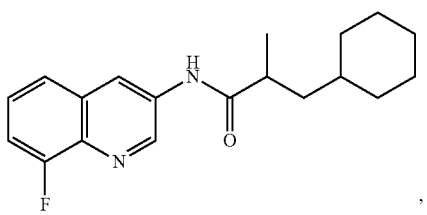

,

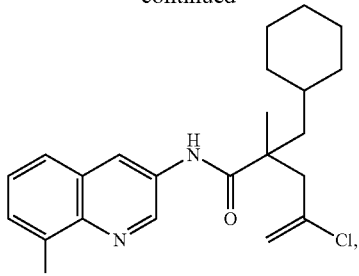

,

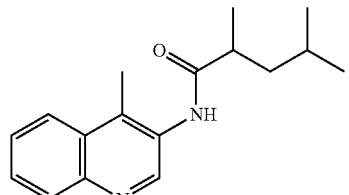

, and

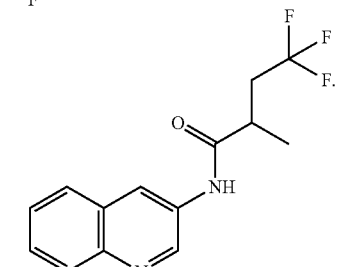

.

14. A composition comprising a fungicidally effective amount of a compound of formula (I) as defined in claim 1.

15. The composition according to claim 14, wherein the composition further comprises at least one additional active ingredient and/or a diluent.

16. A method of combating, preventing or controlling phytopathogenic fungi which comprises applying to phytopathogenic fungi, to the locus of phytopathogenic fungi, or to a plant susceptible to attack by phytopathogenic fungi, or to propagation material thereof, a fungicidally effective amount of a compound of formula (I) as defined in claim 1 or a composition comprising a fungicidally effective amount of a compound of formula (I) as defined in claim 1.

\* \* \* \* \*